US011760983B2

(12) United States Patent
Largaespada et al.

(10) Patent No.: US 11,760,983 B2
(45) **Date of Patent: *Sep. 19, 2023**

(54) ENHANCED HAT FAMILY TRANSPOSON-MEDIATED GENE TRANSFER AND ASSOCIATED COMPOSITIONS, SYSTEMS, AND METHODS

(71) Applicant: B-Mogen Biotechnologies, Inc., Minneapolis, MN (US)

(72) Inventors: David Largaespada, Minneapolis, MN (US); Branden Moriarity, Minneapolis, MN (US); Beau Webber, Minneapolis, MN (US); Neil Otto, Minneapolis, MN (US); Sandeep Kumar, Minneapolis, MN (US); Leah Hogdal, Minneapolis, MN (US)

(73) Assignee: B-Mogen Biotechnologies, Inc., Minneapolis, MN (US)

( * ) Notice: Subject to any disclaimer, the term of this patent is extended or adjusted under 35 U.S.C. 154(b) by 99 days.

This patent is subject to a terminal disclaimer.

(21) Appl. No.: 17/254,162

(22) PCT Filed: Jun. 21, 2019

(86) PCT No.: PCT/US2019/038410

§ 371 (c)(1),
(2) Date: Dec. 18, 2020

(87) PCT Pub. No.: WO2019/246486

PCT Pub. Date: Dec. 26, 2019

(65) Prior Publication Data

US 2021/0277366 A1 Sep. 9, 2021

Related U.S. Application Data

(60) Provisional application No. 62/688,278, filed on Jun. 21, 2018.

(51) Int. Cl.
*C12N 9/12* (2006.01)
*C12N 15/90* (2006.01)

(52) U.S. Cl.
CPC .......... *C12N 9/1241* (2013.01); *C12N 15/90* (2013.01)

(58) Field of Classification Search
None
See application file for complete search history.

(56) References Cited

U.S. PATENT DOCUMENTS

| | | | |
|---|---|---|---|
| 7,064,246 | B2 | 6/2006 | Macrae et al. |
| 7,067,644 | B2 | 6/2006 | Goryshin et al. |
| 7,262,056 | B2 | 8/2007 | Wooddell et al. |
| 7,462,758 | B2 | 12/2008 | Biesgen et al. |
| 8,071,364 | B2 | 12/2011 | Cooper et al. |
| 8,124,404 | B2 | 2/2012 | Alphey et al. |
| 8,236,294 | B2 | 8/2012 | Cooper et al. |
| 8,420,386 | B2 | 4/2013 | Ivics et al. |
| 8,470,973 | B2 | 6/2013 | Bonas et al. |
| 8,524,979 | B2 | 9/2013 | Charng et al. |
| 9,175,295 | B2 | 11/2015 | Kaminaka et al. |
| 9,534,234 | B2 | 1/2017 | Minshull et al. |
| 9,944,953 | B2 | 4/2018 | Zou et al. |
| 10,227,574 | B2 | 3/2019 | Largaespada et al. |
| 2006/0252140 | A1 | 11/2006 | Yant |
| 2010/0287633 | A1 | 11/2010 | Ostergag et al. |
| 2011/0117072 | A1 | 5/2011 | Izsvak et al. |
| 2013/0287748 | A1 | 10/2013 | June et al. |
| 2014/0227237 | A1 | 8/2014 | June et al. |
| 2015/0067900 | A1 | 3/2015 | Duchateau et al. |
| 2015/0152406 | A1 | 6/2015 | Grawunder et al. |
| 2015/0291977 | A1 | 10/2015 | Minshull et al. |
| 2015/0361451 | A1 | 12/2015 | Le Fourn et al. |
| 2017/0107541 | A1 | 4/2017 | Ostertag et al. |
| 2017/0216456 | A1 | 8/2017 | Alexander et al. |
| 2017/0224798 | A1 | 8/2017 | Cooper et al. |
| 2017/0298390 | A1 | 10/2017 | Qin et al. |
| 2017/0306378 | A1 | 10/2017 | Kawakami et al. |
| 2017/0355957 | A1 | 12/2017 | Biondi et al. |
| 2018/0080051 | A1 | 3/2018 | Sheikh et al. |
| 2018/0087050 | A1 | 3/2018 | Zheng et al. |
| 2018/0112235 | A1 | 4/2018 | Li et al. |
| 2018/0187185 | A1 | 7/2018 | Ostertag et al. |
| 2018/0201976 | A1 | 7/2018 | Kavanagh et al. |
| 2018/0216087 | A1 | 8/2018 | Largaespada et al. |
| 2018/0245055 | A1 | 8/2018 | Largaespada et al. |
| 2018/0265890 | A1 | 9/2018 | Qian et al. |
| 2018/0327726 | A1 | 11/2018 | Largaespada et al. |
| 2020/0339965 | A1 | 10/2020 | Largaespada et al. |

FOREIGN PATENT DOCUMENTS

| | | | |
|---|---|---|---|
| EP | 1594972 | B1 | 2/2011 |
| EP | 2692865 | B1 | 12/2014 |
| EP | 2825190 | B1 | 11/2016 |

(Continued)

OTHER PUBLICATIONS

Ammar, et al. Retargeting transposon insertions by the adeno-associated virus Rep protein. Nucleic Acids Res. Aug. 2012; 40(14):6693-6712.

Arensburger, et al. Phylogenetic and Functional Characterization of the hAT Transposon Superfamily. Genetics. May 2011; 188(1): 45-57.

Baus J. et al., "Hyperactive Transposase Mutants of the Sleeping Beauty Transposon." Molecular Therapy, Sep. 8, 2005, vol. 12, No. 6, pp. 1148-1156.

Hickman, et al. Structural basis of hAT transposon end recognition by Hermes, an octameric DNA transposase from *Musca domestica*. Cell. Jul. 17, 2014;158(2):353-367.

Kettlun et al., "Manipulating piggyBac Transposon Chromosomal Integration Site Selection in Human Cells." Molecular Therapy, Sep. 2011, 19(9): 1636-1644.

(Continued)

*Primary Examiner* — Richard G Hutson
(74) *Attorney, Agent, or Firm* — Peter J. Schlueter; Casimir Jones, S.C.

(57) ABSTRACT

This disclosure provides various TcBuster transposases and transposons, systems, and methods of use.

23 Claims, 18 Drawing Sheets

Specification includes a Sequence Listing.

(56) References Cited

FOREIGN PATENT DOCUMENTS

| | | | |
|---|---|---|---|
| WO | WO 2017046259 | A1 | 3/2017 |
| WO | WO 2017050884 | A1 | 3/2017 |
| WO | WO 2017061615 | A1 | 4/2017 |
| WO | WO 2017101749 | | 6/2017 |
| WO | WO 2017123758 | A1 | 7/2017 |
| WO | WO 2017147383 | A1 | 8/2017 |
| WO | WO 2017147538 | A1 | 8/2017 |
| WO | WO 2017158019 | A1 | 9/2017 |
| WO | WO 2017171631 | A1 | 10/2017 |
| WO | WO 2017192924 | A1 | 11/2017 |
| WO | WO 2017219933 | A1 | 12/2017 |
| WO | WO 2017219934 | A1 | 12/2017 |
| WO | WO 2017219936 | A1 | 12/2017 |
| WO | WO 2017219937 | A1 | 12/2017 |
| WO | WO 2018015936 | A2 | 1/2018 |
| WO | WO 2018031683 | A1 | 2/2018 |
| WO | WO 2018042776 | A1 | 3/2018 |
| WO | WO 2018057779 | A1 | 3/2018 |
| WO | WO 2018064681 | A1 | 4/2018 |
| WO | WO 2018102612 | A1 | 6/2018 |
| WO | WO 2018112415 | A1 | 6/2018 |
| WO | WO 2018132494 | A1 | 7/2018 |
| WO | WO 2018140644 | A1 | 8/2018 |

OTHER PUBLICATIONS

Kim, et al. Engineering and Application of Zinc Finger Proteins and TALEs for Biomedical Research. Mol Cells. Aug. 31, 2017; 40(8): 533-541.

Li, et al. A resurrected mammalian hAT transposable element and a closely related insect element are highly active in human cell culture. Proc Natl Acad Sci USA. Feb. 5, 2013; 110(6): E478-E487.

Moore, et al. Transcription Activator-like Effectors: A Toolkit for Synthetic Biology. ACS Synth Biol. Oct. 17, 2014; 3(10): 708-716.

NCBI, Genbank accession No. ABF20545.1 Dec. 31, 2007. 1 Page.

PCT/US2017/066829 International Search Report & Written Opinion dated Apr. 9, 2018.

Search Report dated Sep. 11, 2020, Singapore Application No. 11201905485V, 3 pages.

TcBuster 5'inverted repeat—[Retrieved on Sep. 9, 2019] Retrieved from the internet <https://www.ncbi.nim.nih.gov/nuccore/DQ481197.1/> Deposited in 2007. 2 pages.

Voigt, et al., "Sleeping Beauty transpose structure allows rational design of hyperactive variants for genetic engineering." Nature Communications Mar. 30, 2016, 7(1), 8 pages.

Voigt, et al., Retargeting Sleeping Beauty Transposon Insertions by Engineered Zinc Finger DNA-binding Domains. Mol Ther. Oct. 2012; 20(10): 1852-1862.

Woodard et al., "Mutation the DDE catlytic triad in TcBuster transposase disrupts function and localization." Molecular Therapy May 2014, vol. 22, Supplement 1, S128-S129.

Woodard, et al. Comparative Analysis of the Recently Discovered hAT Transposon TcBuster in Human Cells. PLoS One. 2012; 7(11): e42666. 10 pages.

Woodard, et al. Temporal self-regulation of transposition through host-independent transposase rodlet formation.Nucleic Acids Res. Jan. 9, 2017; 45(1): 353-366.

Written Opinion dated Sep. 18, 2020, Singapore Application No. 11201905485V, 8 pages.

Yant et al. Mutational analysis of the N-terminal DNA-binding domain of sleeping beauty transposase: critical residues for DNA binding and hyperactivity in mammalian cells. Mol Cell Biol. Oct. 2004;24(20):9239-47.

Yusa et al., "A hyperactive piggyBac transposase for mammalian applications." PNAS Jan. 25, 2011, 108(4): 1531-1536.

Zayed et al., Development of Hyperactive Sleeping Beauty Transposon Vectors by Mutational Analysis. Mol Ther, 9.2 (Feb. 2004): 292-304.

Internatinal Search Report and Written Opninion for PCT/US2019/038410. dated Dec. 3, 2019. 7 pages.

```
IRDR-R-Seq1  gatatcaagcttatcgataccgtcgacctcgagatttctgaacgattctaggttaggatcaaacaaaatacaatttattttaaaactgtaagttaactta 100
IRDR-R-Seq2  ga------gc----caattcag----catc-atatttctgaacgattctaggttaggatcaaacaaaatacaatttattttaaaactgtaagttaactta 85

IRDR-R-Seq1  cctttgcttgtctaaaccaaaaacaacaacaaaactacgaccacaagtacagttacatattttgaaaattaaggttaagtgcagtgtaagtcaactatg 200
IRDR-R-Seq2  cctttgcttgtctaaacctaaaacaacaacaaaactacgaccacaagtacagttacatattttgaaaattaaggttaagtgcagtgtaagtcaactatg 185

IRDR-R-Seq1  cgaatggataacatgtttcaacatgaaactccgattgacgcatgtgcattctgaagagcggcgcggccgacgtctctcgaattgaagcaatgactcgcgg 300
IRDR-R-Seq2  cgaatggataacatgtttcaacatgaaactccgattgacgcatgtgcattctgaagagcggcgcggccgacgtctctcgaattgaagcaatgactcgcgg 285

IRDR-R-Seq1  aaccccgaaagcctttgggtggaaccctagggttccgcggaacacaggttgaagaacactg 361
IRDR-R-Seq2  aaccccgaaagcctttgggtggaaccctagggttccgcggaacacaggttgaagaacactg 346
```

FIG. 2 (Cont.)

TcBuster

MMLNWLKSGKLESQSQEQSSCYLENSNCLPPTLDSTDIIGEENKAGTTS
RKKRKYDEDYLNFGFTWTGDKDEPNGLCVICEQVVNNSSLNPAKLKRHL
DTKHPTLKGKSEYFKRKCNELNQKKHTFERYVRDDNKNLLKASYLVSLRI
AKQGEAYTIAEKLIKPCTKDLTTCVFGEKFASKVDLVPLSDTTISRRIEDM
SYFCEAVLVNRLKNAKCGFTLQMDESTDVAGLAILLVFVRYIHESSFEE
DMLFCKALPTQTTGEEIFNLLNAYFEKHSIPWNLCYHICTDGAKAMV
GVIKGVIARIKKLVPDIKASHCCLHRHALAVKRIPNALHEVLNDAVKMINFIK
SRPLNARVFALLCDDLGSLHKNLLLHTEVRWLSRGKVLTRFWELRDEIRI
FFNEREFAGKLNDTSWLQNLAYIADIFSYLNEVNLSLQGPNSTIFKVNSRI
NSIKSKLKLWEECITKNNTECFANLNDFLETSNTALDPNLKSNILEHLNGLK
NTFLEYFPPTCNNISWVENPFNECGNVDTLPIKEREQLIDIRTDTTLKSSF
VPDGIGPFWIKLMDEFPEISKRAVKELMPFVTTYLCEKSFSVYVATKTK
YRNRLDAEDDMRLQLTTIHPDIDNLCNNKQAQKSH

MMLNWLKSGKLESQSQEQSSCYLENSNCLPPTLDSTDIIGEENKAGTTS
RKKRKYDEDYLNFGFTWTGDKDEPNGlcviceqvvnnsslnpaklkrhlDTKHPTL
KGKSEYFKRKCNELNQKKHTFERYVRDDNKNLLKASYLVSLRIAKQGE
**AYTIAEKLIKPCTKDLTTCVFGEKFASKVDLVPLS*A*TTISRRIEDMSYFCE**
AVLVNRLKNAKCGFTLQMDESTDVAGLAILLVFVRYIHESSFEEDMLFCK
ALPTQTTGEEIFNLLNAYFEKHSIPWNLCYHICTDGAKAMVGVIKGVIARIK
KLVPDI*KASHCCLHRHALAVKRIPNALHEVLNDAVKMINFIKSRPLNARVFA*
*LLCDDLGSLHKNLLLHTETRWLSRGKVLTRFWELRDEIRIFFNEREFAGK*
*LNDTSWLQNLAYIADIFSYLNEVNLSLQGPNSTIFKVNSRINSIKSKLKLWE*
*ECITKNNTKCFANLNDFLETSNTALDPNLKSNILEHLNGLKNTFLEYFPPT*
*CNNISWVENPFNECGNVDTLPIKEREQLIDIR*TDTTLKSSFVPDGIGPFWIK
LMDEFPEISKRAVKELMPFVTTYLCEKSFSVYVATKTKYRNRLDAEDDMR
LQLTTIHPDIDNLCNNKQAQKSH

MMLNWLKSGKLESQSQEQSSCYLENSNCLPPTLDSTDIIGEENKAGTTS
RKKRKYDEDYLNFGFTWTGDKDEPNGlcviceqvvnnsslnpaklkrhlDTKHPTL
KGKSEYFKRKCNELNQKKHTFERYVRDDNKNLLKASYLVSLRIAKQGE
**AYTIAEKLIKPCTKDLTTCVFGEKFASKVDLVPLS*A*TTISRRIEDMSYFCE**
AVLVNRLKNAKCGFTLQMDESTDVAGLAILLVFVRYIHESSFEEDMLFCK
ALPTQTTGEEIFNLLNAYFEKHSIPWNLCYHICTDGAKAMVGVIKGVIARIK
KLVPDI*KASHCCLHRHALAVKRIPNALHEVLNDAVKMINFIKSRPLNARVFA*
*LLCDDLGSLHKNLLLHTETRWLSRGKVLTRFWELRDEIRIFFNEREFAGK*
*LNDTSWLQNLAYIADIFSYLNEVNLSLQGPNSTIFKVNSRINS*F*KSKLKLW*
*EECITKNNTKCFANLNDFLETSNTALDPNLKSNILEHLNGLKNTFLEYFPP*
*TCNNISWVENPFNECGNVDTLPIKEREQLIDIR*TDTTLKSSFVPDGIGPFWI
KLMDEFPEISKRAVKELMPFVTTYLCEKSFSVYVATKTKYRNRLDAEDDM
RLQLTTIHPDIDNLCNNKQAQKSH

MMLNWLKSGKLESQSQEQSSCYLENSNCLPPTLDSTDIIGEENKAGTTS
RKKRKYDEDYLNFGFTWTGDKDEPNGlcviceqvvSnsslnpaklkrhlDTKHPT
LKGKSEYFKRKCNELNQKKHTFERYVRDDNKNLLKASYLVSLRIAKQGE
**AYTIAEKLIKPCTKDLTTCVFGEKFASKVDLVPLS*A*TTISRRIEDMSYFCE**
AVLVNRLKNAKCGFTLQMDESTDVAGLAILLVFVRYIHESSFEEDMLFCK
ALPTQTTGEEIFNLLNAYFEKHSIPWNLCYHICTDGAKAMVGVIKGVIARIK
KLVPDI*KASHCCLHRHALAVKRIPNALHEVLNDAVKMINFIKSRPLNARVFA*
*LLCDDLGSLHKNLLLHTETRWLSRGKVLTRFWELRDEIRIFFNEREFAGK*
*LNDTSWLQNLAYIADIFSYLNEVNLSLQGPNSTIFKVNSRINSIKSKLKLWE*
*ECITKNNTKCFANLNDFLETSNTALDPNLKSNILEHLNGLKNTFLEYFPPT*
*CNNISWVENPFNECGNVDTLPIKEREQLIDIR*TDTTLKSSFVPDGIGPFWIK
LMDEFPEISKRAVKELMPFVTTYLCEKSFSVYVATKTKYRNRLDAEDDMR
LQLTTIHPDIDNLCNNKQAQKSH

MMLNWLKSGKLESQSQEQSSCYLENSNCLPPTLDSTDIIGEENKAGTTS
RKKRKYDEDYLNFGFTWTGDKDEPNGlcviceqvvnnsslnpaklkrhlDTKHPTL
KGKSEYFKRKCNELNQKKHTFERYVRDDNKNLLKASYLVSLRIAKQGE
AYTIAEKLIKPCTKDLTTCVFGEKFASKVDLVPLSATTISRRIEDMSYFCE
AVLVNRLKNAKCGFTLQMDESTDVAGLAILLVFVRYIHESSFEEDMLFCK
ALPTQTTGEEIFNLLNAYFEKHSIPWNLCYHICTDGAKAMVGVIKGVIARIK
KLVPDI*KASHCCLHRHALAVKRIPNALHEVLNDAVKMINFIKSRPLNARVF*
K*LLCDDLGSLHKNLLLHTETRWLSRGKVLTRFWELRDEIRIFFNEREFA*
*GKLNDTSWLQNLAYIADIFSYLNEVNLSLQGPNSTIFKVNSRINSIKSKLKL*
*WEECITKNNTKCFANLNDFLETSNTALDPNLKSNILEHLNGLKNTFLEYF*
*PPTCNNISWVENPFNECGNVDTLPIKEREQLIDIRTDTTLKSSFVPDGIGPF*
WIKLMDEFPEISKRAVKELMPFVTTYLCEKSFSVYVATKTKYRNRLDAED
DMRLQLTTIHPDIDNLCNNKQAQKSH

MMLNWLKSGKLESQSQEQSSCYLENSNCLPPTLDSTDIIGEENKAGTTS
RKKRKYDEDYLNFGFTWTGDKDEPNGlcviceqvvnnsslnpaklkrhIDTKHPTL
KGKSEYFKRKCNELNQKKHTFERYVRDDNKNLLKASYLVSLRIAKQGE
**AYTIAEKLIKPCTKDLTTCVFGEKFASKVDLVPLS*A*TTISRRIEDMSYFCE**
AVLVNRLKNAKCGFTLQMDESTDVAGLAILLVFVRYIHESSFEEDMLFCK
ALPTQTTGEEIFNLLNAYFEKHSIPWNLCYHICTDGAKAMVGVIKGVIARIK
KLVPDI*KASHCCLHRHALAVKRIPNALHEVLNDAVKMINFIKSRPLNARVFA*
*LLCDDLGSLHKNLLLHTETRWLSRGKVLTRFWELRDEIRIFFNEREFAGK*
*LNDTSWLQNLAYIADIFSYLNEVNLSLQGPNSTIFKVNSRINSIKSKLKLWE*
*ECITKNNTKCFANLNDFLETSNTALDPNLKSNILEHLNGLKNTFLEYFPPT*
*CNNISWVENPFNECGNVDTLPIKEREQLIDIR*TDTTLKSSFVPDGIGPFWIK
LMDEFPEISEKRAVKLLMPFVTTYLCEKSFSVYVATKTKYRNRLDAEDDM
RLQLTTIHPDIDNLCNNKQAQKSH

FIG. 16

SEQUENCE LISTING

<160> NUMBER OF SEQ ID NOS: 220

<210> SEQ ID NO 1
<211> LENGTH: 636
<212> TYPE: PRT
<213> ORGANISM: Tribolium castaneum

<400> SEQUENCE: 1

```
Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Asp Thr Thr Ile
            180                 185                 190

Ser Arg Arg Ile Glu Asp Met Ser Tyr Phe Cys Glu Ala Val Leu Val
        195                 200                 205

Asn Arg Leu Lys Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350

Asn Ala Arg Val Phe Ala Leu Leu Cys Asp Asp Leu Gly Ser Leu His
        355                 360                 365

Lys Asn Leu Leu Leu His Thr Glu Val Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
```

-continued

```
                405                 410                 415

Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445

Ile Asn Ser Ile Lys Ser Lys Leu Lys Leu Trp Glu Glu Cys Ile Thr
    450                 455                 460

Lys Asn Asn Thr Glu Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
        515                 520                 525

Asp Thr Leu Pro Ile Lys Glu Arg Glu Gln Leu Ile Asp Ile Arg Thr
    530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Lys Arg Ala Val
                565                 570                 575

Lys Glu Leu Met Pro Phe Val Thr Thr Tyr Leu Cys Glu Lys Ser Phe
            580                 585                 590

Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635
```

<210> SEQ ID NO 2
<211> LENGTH: 1911
<212> TYPE: DNA
<213> ORGANISM: Tribolium castaneum

<400> SEQUENCE: 2

```
atgatgttga attggctgaa aagtggaaag cttgaaagtc aatcacagga acagagttcc      60

tgctaccttg agaactctaa ctgcctgcca ccaacgctcg attctacaga tattatcggt     120

gaagagaaca aagctggtac cacctctcgc aagaagcgga aatatgacga ggactatctg     180

aacttcggtt ttacatggac tggcgacaag gatgagccca acggactttg tgtgatttgc     240

gagcaggtag tcaacaattc ctcacttaac ccggccaaac tgaaacgcca tttggacaca     300

aagcatccga cgcttaaagg caagagcgaa tacttcaaaa gaaaatgtaa cgagctcaat     360

caaaagaagc atacttttga gcgatacgta agggacgata acaagaacct cctgaaagct     420

tcttatctcg tcagtttgag aatagctaaa cagggcgagg catataccat agcggagaag     480

ttgatcaagc cttgcaccaa ggatctgaca acttgcgtat ttggagaaaa attcgcgagc     540

aaagttgatc tcgtcccccct gtccgacacg actatttcaa ggcgaatcga agacatgagt     600

tacttctgtg aagccgtgct ggtgaacagg ttgaaaaatg ctaaatgtgg gtttacgctg     660

cagatggacg agtcaacaga tgttgccggt cttgcaatcc tgcttgtgtt tgttaggtac     720

atacatgaaa gctcttttga ggaggatatg ttgttctgca aagcacttcc cactcagacg     780

acaggggagg agattttcaa tcttctcaat gcctatttcg aaaagcactc catcccatgg     840
```

-continued aatctgtgtt accacatttg cacagacggt gccaaggcaa tggtaggagt tattaaagga 900
gtcatagcga gaataaaaaa actcgtccct gatataaaag ctagccactg ttgcctgcat 960
cgccacgctt tggctgtaaa gcgaataccg aatgcattgc acgaggtgct caatgacgct 1020
gttaaaatga tcaacttcat caagtctcgg ccgttgaatg cgcgcgtctt cgctttgctg 1080
tgtgacgatt tggggagcct gcataaaaat cttcttcttc ataccgaagt gaggtggctg 1140
tctagaggaa aggtgctgac ccgattttgg gaactgagag atgaaattag aattttcttc 1200
aacgaaaggg aatttgccgg gaaattgaac gacaccagtt ggttgcaaaa tttggcatat 1260
atagctgaca tattcagtta tctgaatgaa gttaatcttt ccctgcaagg gccgaatagc 1320
acaatcttca aggtaaatag ccgcattaac agtattaaat caaagttgaa gttgtgggaa 1380
gagtgtataa cgaaaaataa cactgagtgt tttgcgaacc tcaacgattt tttggaaact 1440
tcaaacactg cgttggatcc aaacctgaag tctaatattt tggaacatct caacggtctt 1500
aagaacacct ttctggagta ttttccacct acgtgtaata atatctcctg ggtggagaat 1560
cctttcaatg aatgcggtaa cgtcgataca ctcccaataa aagagaggga acaattgatt 1620
gacatacgga ctgatacgac attgaaatct tcattcgtgc ctgatggtat aggaccattc 1680
tggatcaaac tgatggacga atttccagaa attagcaaac gagctgtcaa agagctcatg 1740
ccatttgtaa ccacttacct ctgtgagaaa tcattttccg tctatgtagc cacaaaaaca 1800
aaatatcgaa atagacttga tgctgaagac gatatgcgac tccaacttac tactatccat 1860
ccagacattg acaacctttg taacaacaag caggctcaga aatcccactg a 1911

<210> SEQ ID NO 3
<211> LENGTH: 458
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
cagtgttctt caacctttgc catccggcgg aaccctttgt cgagatattt tttttatgg 60 aacccttcat ttagtaatac acccagatga gattttaggg acagctgcgt tgacttgtta 120
cgaacaaggt gagcccgtgc tttggtctag ccaagggcat ggtaaagact atattcgcgg 180
cgttgtgaca atttaccgaa caactccgcg gccgggaagc cgatctcggc ttgaacgaat 240
tgttaggtgg cggtacttgg gtcgatatca aagtgcatca cttcttcccg tatgcccaac 300
tttgtataga gagccactgc gggatcgtca ccgtaatctg cttgcacgta gatcacataa 360
gcaccaagcg cgttggcctc atgcttgagg agattgatga gcgcggtggc aatgccctgc 420
ctccggtgct cgccggagac tgcgagatca tagatata 458

<210> SEQ ID NO 4
<211> LENGTH: 361
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
gatatcaagc ttatcgatac cgtcgacctc gagatttctg aacgattcta ggttaggatc 60
aaacaaaata caatttattt taaaactgta agttaactta cctttgcttg tctaaaccaa 120

```
aaacaacaac aaaactacga ccacaagtac agttacatat ttttgaaaat taaggttaag    180

tgcagtgtaa gtcaactatg cgaatggata acatgtttca acatgaaact ccgattgacg    240

catgtgcatt ctgaagagcg gcgcggccga cgtctctcga attgaagcaa tgactcgcgg    300

aaccccgaaa gcctttgggt ggaaccctag ggttccgcgg aacacaggtt gaagaacact    360

g                                                                    361


<210> SEQ ID NO 5
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

cctgcaggag tgttcttcaa cctttgccat ccggcggaac cctttgtcga gatatttttt     60

tttatggaac ccttcattta gtaatacacc cagatgagat tttagggaca gctgcgttga    120

cttgttacga acaaggtgag cccgtgcttt ggtaataaaa actctaaata agatttaaat    180

ttgcatttat ttaaacaaac tttaaacaaa aagataaata ttccaaataa aataatatat    240

aaaataaaaa ataaaaatta atgacttttt tgcgcttgct tattattgca caaattatca    300

atatcgggat ggatcgttgt ttttt                                          325


<210> SEQ ID NO 6
<211> LENGTH: 346
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

gagccaattc agcatcatat ttctgaacga ttctaggtta ggatcaaaca aaatacaatt     60

tattttaaaa ctgtaagtta acttaccttt gcttgtctaa acctaaaaca acaacaaaac    120

tacgaccaca agtacagtta catatttttg aaaattaagg ttaagtgcag tgtaagtcaa    180

ctatgcgaat ggataacatg tttcaacatg aaactccgat tgacgcatgt gcattctgaa    240

gagcggcgcg gccgacgtct ctcgaattga agcaatgact cgcggaaccc cgaaagcctt    300

tgggtggaac cctagggttc cgcggaacac aggttgaaga acactg                   346


<210> SEQ ID NO 7
<211> LENGTH: 7143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360
```

-continued

```
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagctatca acaagtttgt acaaaaaagc tgaacgagaa acgtaaaatg atataaatat    960
caatatatta aattagattt tgcataaaaa acagactaca taatactgta aaacacaaca   1020
tatccagtca ctatggcggc cgcattaggc accccaggct ttacacttta tgcttccggc   1080
tcgtataatg tgtggatttt gagttaggat ccggcgagat tttcaggagc taaggaagct   1140
aaaatggaga aaaaaatcac tggatatacc accgttgata tatcccaatg gcatcgtaaa   1200
gaacattttg aggcatttca gtcagttgct caatgtacct ataaccagac cgttcagctg   1260
gatattacgg cctttttaaa gaccgtaaag aaaaataagc acaagtttta tccggccttt   1320
attcacattc ttgcccgcct gatgaatgct catccggaat tccgtatggc aatgaaagac   1380
ggtgagctgg tgatatggga tagtgttcac ccttgttaca ccgttttcca tgagcaaact   1440
gaaacgtttt catcgctctg gagtgaatac cacgacgatt tccggcagtt tctacacata   1500
tattcgcaag atgtggcgtg ttacggtgaa aacctggcct atttccctaa agggtttatt   1560
gagaatatgt ttttcgtctc agccaatccc tgggtgagtt tcaccagttt tgatttaaac   1620
gtggccaata tggacaactt cttcgccccc gttttcacca tgggcaaata ttatacgcaa   1680
ggcgacaagg tgctgatgcc gctggcgatt caggttcatc atgccgtctg tgatggcttc   1740
catgtcggca gaatgcttaa tgaattacaa cagtactgcg atgagtggca gggcggggcg   1800
taaagatctg gatccggctt actaaaagcc agataacagt atgcgtattt gcgcgctgat   1860
ttttgcggta taagaatata tactgatatg tatacccgaa gtatgtcaaa aagaggtgtg   1920
ctatgaagca gcgtattaca gtgacagttg acagcgacag ctatcagttg ctcaaggcat   1980
atatgatgtc aatatctccg gtctggtaag cacaaccatg cagaatgaag cccgtcgtct   2040
gcgtgccgaa cgctggaaag cggaaaatca ggaagggatg gctgaggtcg cccggtttat   2100
tgaaatgaac ggctcttttg ctgacgagaa cagggactgg tgaaatgcag tttaaggttt   2160
acacctataa aagagagagc cgttatcgtc tgtttgtgga tgtacagagt gatattattg   2220
acacgcccgg gcgacggatg gtgatccccc tggccagtgc acgtctgctg tcagataaag   2280
tctcccgtga actttacccg gtggtgcata tcggggatga aagctggcgc atgatgacca   2340
ccgatatggc cagtgtgccg gtctccgtta tcggggaaga agtggctgat ctcagccacc   2400
gcgaaaatga catcaaaaac gccattaacc tgatgttctg gggaatataa atgtcaggct   2460
ccgttataca cagccagtct gcaggtcgac catagtgact ggatatgttg tgttttacag   2520
tattatgtag tctgtttttt atgcaaaatc taatttaata tattgatatt tatatcattt   2580
tacgtttctc gttcagcttt cttgtacaaa gtggttgatc tagagggccc gcggttcgaa   2640
ggtaagccta tccctaaccc tctcctcggt ctcgattcta cgcgtaccgg tcatcatcac   2700
catcaccatt gagtttaaac ccgctgatca gcctcgactg tgccttctag ttgccagcca   2760
```

```
tctgttgttt gcccctcccc cgtgccttcc ttgaccctgg aaggtgccac tcccactgtc   2820
ctttcctaat aaaatgagga aattgcatcg cattgtctga gtaggtgtca ttctattctg   2880
gggggtgggg tggggcagga cagcaagggg gaggattggg aagacaatag caggcatgct   2940
ggggatgcgg tgggctctat ggcttctgag gcggaaagaa ccagctgggg ctctaggggg   3000
tatccccacg cgccctgtag cggcgcatta agcgcggcgg gtgtggtggt tacgcgcagc   3060
gtgaccgcta cacttgccag cgccctagcg cccgctcctt tcgctttctt cccttccttt   3120
ctcgccacgt tcgccggctt tccccgtcaa gctctaaatc gggggctccc tttagggttc   3180
cgatttagtg ctttacggca cctcgacccc aaaaaacttg attagggtga tggttcacgt   3240
agtgggccat cgccctgata gacggttttt cgccctttga cgttggagtc cacgttcttt   3300
aatagtggac tcttgttcca aactggaaca acactcaacc ctatctcggt ctattctttt   3360
gatttataag ggattttgcc gatttcggcc tattggttaa aaaatgagct gatttaacaa   3420
aaatttaacg cgaattaatt ctgtggaatg tgtgtcagtt agggtgtgga aagtccccag   3480
gctccccagc aggcagaagt atgcaaagca tgcatctcaa ttagtcagca accaggtgtg   3540
gaaagtcccc aggctcccca gcaggcagaa gtatgcaaag catgcatctc aattagtcag   3600
caaccatagt cccgccccta actccgccca tcccgcccct aactccgccc agttccgccc   3660
attctccgcc ccatggctga ctaatttttt ttatttatgc agaggccgag gccgcctctg   3720
cctctgagct attccagaag tagtgaggag gcttttttgg aggcctaggc ttttgcaaaa   3780
agctcccggg agcttgtata tccattttcg gatctgatca agagacagga tgaggatcgt   3840
ttcgcatgat tgaacaagat ggattgcacg caggttctcc ggccgcttgg gtggagaggc   3900
tattcggcta tgactgggca caacagacaa tcggctgctc tgatgccgcc gtgttccggc   3960
tgtcagcgca ggggcgcccg gttctttttg tcaagaccga cctgtccggt gccctgaatg   4020
aactgcagga cgaggcagcg cggctatcgt ggctggccac gacgggcgtt ccttgcgcag   4080
ctgtgctcga cgttgtcact gaagcgggaa gggactggct gctattgggc gaagtgccgg   4140
ggcaggatct cctgtcatct caccttgctc ctgccgagaa agtatccatc atggctgatg   4200
caatgcggcg gctgcatacg cttgatccgg ctacctgccc attcgaccac caagcgaaac   4260
atcgcatcga gcgagcacgt actcggatgg aagccggtct tgtcgatcag gatgatctgg   4320
acgaagagca tcaggggctc gcgccagccg aactgttcgc caggctcaag gcgcgcatgc   4380
ccgacggcga ggatctcgtc gtgacccatg gcgatgcctg cttgccgaat atcatggtgg   4440
aaaatggccg cttttctgga ttcatcgact gtggccggct gggtgtggcg gaccgctatc   4500
aggacatagc gttggctacc cgtgatattg ctgaagagct tggcggcgaa tgggctgacc   4560
gcttcctcgt gctttacggt atcgccgctc ccgattcgca gcgcatcgcc ttctatcgcc   4620
ttcttgacga gttcttctga gcgggactct ggggttcgcg aaatgaccga ccaagcgacg   4680
cccaacctgc catcacgaga tttcgattcc accgccgcct tctatgaaag gttgggcttc   4740
ggaatcgttt tccgggacgc cggctggatg atcctccagc gcggggatct catgctggag   4800
ttcttcgccc accccaactt gtttattgca gcttataatg gttacaaata aagcaatagc   4860
atcacaaatt tcacaaataa agcatttttt tcactgcatt ctagttgtgg tttgtccaaa   4920
ctcatcaatg tatcttatca tgtctgtata ccgtcgacct ctagctagag cttggcgtaa   4980
tcatggtcat agctgtttcc tgtgtgaaat tgttatccgc tcacaattcc acacaacata   5040
cgagccggaa gcataaagtg taaagcctgg ggtgcctaat gagtgagcta actcacatta   5100
```

-continued

```
attgcgttgc gctcactgcc cgctttccag tcgggaaacc tgtcgtgcca gctgcattaa   5160

tgaatcggcc aacgcgcggg gagaggcggt ttgcgtattg ggcgctcttc cgcttcctcg   5220

ctcactgact cgctgcgctc ggtcgttcgg ctgcggcgag cggtatcagc tcactcaaag   5280

gcggtaatac ggttatccac agaatcaggg gataacgcag gaaagaacat gtgagcaaaa   5340

ggccagcaaa aggccaggaa ccgtaaaaag gccgcgttgc tggcgttttt ccataggctc   5400

cgcccccctg acgagcatca caaaaatcga cgctcaagtc agaggtggcg aaacccgaca   5460

ggactataaa gataccaggc gtttccccct ggaagctccc tcgtgcgctc tcctgttccg   5520

accctgccgc ttaccggata cctgtccgcc tttctccctt cgggaagcgt ggcgctttct   5580

catagctcac gctgtaggta tctcagttcg gtgtaggtcg ttcgctccaa gctgggctgt   5640

gtgcacgaac cccccgttca gcccgaccgc tgcgccttat ccggtaacta tcgtcttgag   5700

tccaacccgg taagacacga cttatcgcca ctggcagcag ccactggtaa caggattagc   5760

agagcgaggt atgtaggcgg tgctacagag ttcttgaagt ggtggcctaa ctacggctac   5820

actagaagaa cagtatttgg tatctgcgct ctgctgaagc cagttacctt cggaaaaaga   5880

gttggtagct cttgatccgg caaacaaacc accgctggta gcggtggttt ttttgtttgc   5940

aagcagcaga ttacgcgcag aaaaaaagga tctcaagaag atcctttgat cttttctacg   6000

gggtctgacg ctcagtggaa cgaaaactca cgttaaggga ttttggtcat gagattatca   6060

aaaaggatct tcacctagat ccttttaaat taaaaatgaa gttttaaatc aatctaaagt   6120

atatatgagt aaacttggtc tgacagttac caatgcttaa tcagtgaggc acctatctca   6180

gcgatctgtc tatttcgttc atccatagtt gcctgactcc ccgtcgtgta gataactacg   6240

atacgggagg gcttaccatc tggccccagt gctgcaatga taccgcgaga cccacgctca   6300

ccggctccag atttatcagc aataaaccag ccagccggaa gggccgagcg cagaagtggt   6360

cctgcaactt tatccgcctc catccagtct attaattgtt gccgggaagc tagagtaagt   6420

agttcgccag ttaatagttt gcgcaacgtt gttgccattg ctacaggcat cgtggtgtca   6480

cgctcgtcgt ttggtatggc ttcattcagc tccggttccc aacgatcaag gcgagttaca   6540

tgatccccca tgttgtgcaa aaaagcggtt agctccttcg gtcctccgat cgttgtcaga   6600

agtaagttgg ccgcagtgtt atcactcatg gttatggcag cactgcataa ttctcttact   6660

gtcatgccat ccgtaagatg cttttctgtg actggtgagt actcaaccaa gtcattctga   6720

gaatagtgta tgcggcgacc gagttgctct tgcccggcgt caatacggga taataccgcg   6780

ccacatagca gaactttaaa agtgctcatc attggaaaac gttcttcggg gcgaaaactc   6840

tcaaggatct taccgctgtt gagatccagt tcgatgtaac ccactcgtgc acccaactga   6900

tcttcagcat cttttacttt caccagcgtt tctgggtgag caaaaacagg aaggcaaaat   6960

gccgcaaaaa agggaataag ggcgacacgg aaatgttgaa tactcatact cttccttttt   7020

caatattatt gaagcattta tcagggttat tgtctcatga gcggatacat atttgaatgt   7080

atttagaaaa ataaacaaat aggggttccg cgcacatttc cccgaaaagt gccacctgac   7140

gtc                                                                 7143
```

<210> SEQ ID NO 8
<211> LENGTH: 2844
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
atgctcgaga tggatccctc cgacgcttcg ccggccgcgc aggtggatct acgcacgctc 60
ggctacagtc agcagcagca agagaagatc aaaccgaagg tgcgttcgac agtggcgcag 120
caccacgagg cactggtggg ccatgggttt acacacgcgc acatcgttgc gctcagccaa 180
cacccggcag cgttagggac cgtcgctgtc acgtatcagc acataatcac ggcgttgcca 240
gaggcgacac acgaagacat cgttggcgtc ggcaaacagt ggtccggcgc acgcgccctg 300
gaggccttgt tgactgatgc tggtgagctt agaggacctc ctttgcaact tgatacaggc 360
cagcttctga aaatcgccaa gaggggtggg gtcaccgcgg tcgaggccgt acacgcctgg 420
agaaatgcac tgaccggggc tcctcttaac ctgaccccag accaggtagt cgcaatcgcg 480
tcaaacggag gggaaagca agccctggaa accgtgcaaa ggttgttgcc ggtcctttgt 540
caagaccacg gccttacacc ggagcaagtc gtggccattg catcccacga cggtggcaaa 600
caggctcttg agacggttca gagacttctc ccagttctct gtcaagccca cgggctgact 660
cccgatcaag ttgtagcgat tgcgtcgcat gacggaggga aacaagcatt ggagactgtc 720
caacggctcc ttcccgtgtt gtgtcaagcc cacggtttga cgcctgcaca agtggtcgcc 780
atcgcctcca atattggcgg taagcaggcg ctggaaacag tacagcgcct gctgcctgta 840
ctgtgccagg atcatggact gacggccaag ctggccgggg gcgcccccgc cgtgggcggg 900
ggccccaagg ccgccgataa attcgccgcc accatgatgt tgaattggct gaaaagtgga 960
aagcttgaaa gtcaatcaca ggaacagagt tcctgctacc ttgagaactc taactgcctg 1020
ccaccaacgc tcgattctac agatattatc ggtgaagaga acaaagctgg taccacctct 1080
cgcaagaagc ggaaatatga cgaggactat ctgaacttcg gttttacatg gactggcgac 1140
aaggatgagc ccaacggact ttgtgtgatt tgcgagcagg tagtcaacaa ttcctcactt 1200
aacccggcca aactgaaacg ccatttggac acaaagcatc cgacgcttaa aggcaagagc 1260
gaatacttca aaagaaaatg taacgagctc aatcaaaaga agcatacttt tgagcgatac 1320
gtaagggacg ataacaagaa cctcctgaaa gcttcttatc tcgtcagttt gagaatagct 1380
aaacagggcg aggcatatac catagcggag aagttgatca agccttgcac caaggatctg 1440
acaacttgcg tatttggaga aaaattcgcg agcaaagttg atctcgtccc cctgtccgac 1500
acgactattt caaggcgaat cgaagacatg agttacttct gtgaagccgt gctggtgaac 1560
aggttgaaaa atgctaaatg tgggtttacg ctgcagatgg acgagtcaac agatgttgcc 1620
ggtcttgcaa tcctgcttgt gtttgttagg tacatacatg aaagctcttt tgaggaggat 1680
atgttgttct gcaaagcact tcccactcag acgacagggg aggagatttt caatcttctc 1740
aatgcctatt tcgaaaagca ctccatccca tggaatctgt gttaccacat ttgcacagac 1800
ggtgccaagg caatggtagg agttattaaa ggagtcatag cgagaataaa aaaactcgtc 1860
cctgatataa aagctagcca ctgttgcctg catcgccacg ctttggctgt aaagcgaata 1920
ccgaatgcat tgcacgaggt gctcaatgac gctgttaaaa tgatcaactt catcaagtct 1980
cggccgttga atgcgcgcgt cttcgctttg ctgtgtgacg atttggggag cctgcataaa 2040
aatcttcttc ttcataccga agtgaggtgg ctgtctagag gaaaggtgct gacccgattt 2100
tgggaactga gagatgaaat tagaattttc ttcaacgaaa gggaatttgc cgggaaattg 2160
aacgacacca gttggttgca aaatttggca tatatagctg acatattcag ttatctgaat 2220
gaagttaatc tttccctgca agggccgaat agcacaatct tcaaggtaaa tagccgcatt 2280
aacagtatta aatcaaagtt gaagttgtgg gaagagtgta taacgaaaaa taacactgag 2340

```
tgttttgcga acctcaacga ttttttggaa acttcaaaca ctgcgttgga tccaaacctg   2400

aagtctaata ttttggaaca tctcaacggt cttaagaaca cctttctgga gtattttcca   2460

cctacgtgta ataatatctc ctgggtggag aatcctttca atgaatgcgg taacgtcgat   2520

acactcccaa taaaagagag ggaacaattg attgacatac ggactgatac gacattgaaa   2580

tcttcattcg tgcctgatgg tataggacca ttctggatca aactgatgga cgaatttcca   2640

gaaattagca aacgagctgt caaagagctc atgccatttg taaccactta cctctgtgag   2700

aaatcatttt ccgtctatgt agccacaaaa acaaaatatc gaaatagact tgatgctgaa   2760

gacgatatgc gactccaact tactactatc catccagaca ttgacaacct ttgtaacaac   2820

aagcaggctc agaaatccca ctga                                          2844
```

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

```
Gly Gly Ser Gly Gly Ser Gly Gly Ser Gly Gly Ser Gly Thr Ser
1               5                   10                  15
```

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 10

```
ggaggtagtg gcggtagtgg gggctccggt gggagcggca cctca                     45
```

<210> SEQ ID NO 11
<211> LENGTH: 863
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
atgctcgaga tggatccctc cgacgcttcg ccggccgcgc aggtggatct acgcacgctc     60

ggctacagtc agcagcagca agagaagatc aaaccgaagg tgcgttcgac agtggcgcag    120

caccacgagg cactggtggg ccatgggttt acacacgcgc acatcgttgc gctcagccaa    180

cacccggcag cgttagggac cgtcgctgtc acgtatcagc acataatcac ggcgttgcca    240

gaggcgacac acgaagacat cgttggcgtc ggcaaacagt ggtccggcgc acgcgccctg    300

gaggccttgt tgactgatgc tggtgagctt agaggacctc ctttgcaact tgatacaggc    360

cagcttctga aaatcgccaa gaggggtggg gtcaccgcgg tcgaggccgt acacgcctgg    420

agaaatgcac tgaccggggc tcctcttaac ctgaccccag accaggtagt cgcaatcgcg    480

tcaaacggag gggaaagca agccctggaa accgtgcaaa ggttgttgcc ggtcctttgt    540

caagaccacg gccttacacc ggagcaagtc gtggccattg catcccacga cggtggcaaa    600

caggctcttg agacggttca gagacttctc ccagttctct gtcaagccca cgggctgact    660
```

-continued

```
cccgatcaag ttgtagcgat tgcgtcgcat gacggaggga aacaagcatt ggagactgtc    720

caacggctcc ttcccgtgtt gtgtcaagcc cacggtttga cgcctgcaca agtggtcgcc    780

atcgcctcca atattggcgg taagcaggcg ctggaaacag tacagcgcct gctgcctgta    840

ctgtgccagg atcatggact gac                                            863
```

```
<210> SEQ ID NO 12
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

ggccaagctg gccgggggcg cccccgccgt gggcgggggc cccaaggccg ccgataaatt     60

cgccgccacc                                                            70
```

```
<210> SEQ ID NO 13
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Ala Thr Thr Ile
            180                 185                 190

Ser Arg Arg Ile Glu Asp Met Ser Tyr Phe Cys Glu Ala Val Leu Val
        195                 200                 205

Asn Arg Leu Lys Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240
```

-continued

```
Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350

Asn Ala Arg Val Phe Ala Leu Leu Cys Asp Asp Leu Gly Ser Leu His
        355                 360                 365

Lys Asn Leu Leu Leu His Thr Glu Thr Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
                405                 410                 415

Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445

Ile Asn Ser Ile Lys Ser Lys Leu Lys Leu Trp Glu Glu Cys Ile Thr
    450                 455                 460

Lys Asn Asn Thr Lys Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
        515                 520                 525

Asp Thr Leu Pro Ile Lys Glu Arg Glu Gln Leu Ile Asp Ile Arg Thr
    530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Glu Arg Ala Val
                565                 570                 575

Lys Leu Leu Met Pro Phe Val Thr Thr Tyr Leu Cys Glu Lys Ser Phe
            580                 585                 590

Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635
```

<210> SEQ ID NO 14
<211> LENGTH: 22
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 14

gatttgcgag gaggtagtca ac                                             22


<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

acacaaagtc cgttgggc                                                  18


<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16

cgcgtcttcg aattgctgtg tgac                                           24


<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

cgcattcaac ggccgaga                                                  18


<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

gcgcgtcttc agtttgctgt gtgacg                                         26


<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

gcattcaacg gccgagac                                                  18


<210> SEQ ID NO 20
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 20

gcgcgtcttc aagttgctgt gtgacg                                          26


<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

gcattcaacg gccgagac                                                   18


<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

caaggtaaat gagcgcatta acagtattaa atc                                  33


<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23

aagattgtgc tattcggc                                                   18


<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

cattaacagt tttaaatcaa agttgaag                                        28


<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

cggctattta ccttgaag                                                   18


<210> SEQ ID NO 26
<211> LENGTH: 23
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 26
catcccatgg gaactgtgtt acc 23

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gagtgctttt cgaaatagg 19

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cggtcttgca cagctgcttg tgtttg 26

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcaacatctg ttgactcg 18

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtattttcca gatacgtgta ataatatctc ctg 33

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tccagaaagg tgttcttaag 20

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
gtattttcca aatacgtgta ataatatctc c 31

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
tccagaaagg tgttcttaag 20

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ctcctgggtg cggaatcctt tcaatg 26

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
atattattac acgtaggtgg 20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
gaaattagca cacgagctgt c 21

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
tggaaattcg tccatcag 18

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
gcaggtagtc agcaattcct cac 23

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
tcgcaaatca cacaaagtc 19

<210> SEQ ID NO 40
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
taaaggcaag gacgaatact tcaaaagaaa atgtaac 37

<210> SEQ ID NO 41
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
taaaggcaag gacgaatact tcaaaagaaa atgtaac 37

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ggacgataac gagaacctcc tga 23

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
cttacgtatc gctcaaaagt atg 23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
acgccatttg gcaacaaagc atc 23

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 45
ttcagtttgg ccgggtta 18

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 46
atacgtaagg gcagataaca agaacc 26

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 47
cgctcaaaag tatgcttc 18

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 48
taccatagcg gcgaagttga tcaag 25

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 49
tatgcctcgc cctgttta 18

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 50
ccccctgtcc gcaacgacta tttc                                    24

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
acgagatcaa ctttgctc                                           18

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgagtcaaca gcagttgccg gtc                                     23

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tccatctgca gcgtaaac                                           18

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gtacatacat gcaagctctt ttg                                     23

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctaacaaaca caagcagg                                           18

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tcataccgaa acgaggtggc tgtc 24

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 57
agaagaagat ttttatgcag g 21

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 58
gatggacgag tggacagatg ttgc 24

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
tgcagcgtaa acccacat 18

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
gggcgaggca tttaccatag cgg 23

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61
tgtttagcta ttctcaaact gacgagataa g 31

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
atacgtaagg gcagataaca agaacc 26

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 63
cgctcaaaag tatgcttc 18

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
taccatagcg gcgaagttga tcaag 25

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 65
tatgcctcgc cctgttta 18

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
ccccctgtcc gcaacgacta tttc 24

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
acgagatcaa ctttgctc 18

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
cgagtcaaca gcagttgccg gtc 23

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
tccatctgca gcgtaaac 18

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
gtacatacat gcaagctctt ttg 23

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
ctaacaaaca caagcagg 18

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
tcataccgaa acgaggtggc tgtc 24

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
agaagaagat ttttatgcag g 21

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
gatggacgag tggacagatg ttgc 24

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
tgcagcgtaa acccacat 18

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
gggcgaggca tttaccatag cgg 23

<210> SEQ ID NO 77
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
tgtttagcta ttctcaaact gacgagataa g 31

<210> SEQ ID NO 78
<211> LENGTH: 636
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 78

```
Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160
```

-continued

```
Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Ala Thr Thr Ile
            180                 185                 190

Ser Arg Arg Ile Glu Asp Met Ser Tyr Phe Cys Glu Ala Val Leu Val
        195                 200                 205

Asn Arg Leu Lys Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350

Asn Ala Arg Val Phe Ala Leu Leu Cys Asp Asp Leu Gly Ser Leu His
        355                 360                 365

Lys Asn Leu Leu Leu His Thr Glu Thr Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
                405                 410                 415

Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445

Ile Asn Ser Ile Lys Ser Lys Leu Lys Leu Trp Glu Glu Cys Ile Thr
    450                 455                 460

Lys Asn Asn Thr Lys Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
        515                 520                 525

Asp Thr Leu Pro Ile Lys Glu Arg Glu Gln Leu Ile Asp Ile Arg Thr
    530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Lys Arg Ala Val
                565                 570                 575

Lys Glu Leu Met Pro Phe Val Thr Thr Tyr Leu Cys Glu Lys Ser Phe
```

```
            580                 585                 590

Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635


<210> SEQ ID NO 79
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Ala Thr Thr Ile
            180                 185                 190

Ser Arg Arg Ile Glu Asp Met Ser Tyr Phe Cys Glu Ala Val Leu Val
        195                 200                 205

Asn Arg Leu Lys Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300
```

-continued

Ile Lys Lys Leu Val Pro Asp Ile Lys Ala Ser His Cys Cys Leu His
305 310 315 320

Arg His Ala Leu Ala Val Lys Arg Ile Pro Asn Ala Leu His Glu Val
325 330 335

Leu Asn Asp Ala Val Lys Met Ile Asn Phe Ile Lys Ser Arg Pro Leu
340 345 350

Asn Ala Arg Val Phe Ala Leu Leu Cys Asp Asp Leu Gly Ser Leu His
355 360 365

Lys Asn Leu Leu Leu His Thr Glu Thr Arg Trp Leu Ser Arg Gly Lys
370 375 380

Val Leu Thr Arg Phe Trp Glu Leu Arg Asp Glu Ile Arg Ile Phe Phe
385 390 395 400

Asn Glu Arg Glu Phe Ala Gly Lys Leu Asn Asp Thr Ser Trp Leu Gln
405 410 415

Asn Leu Ala Tyr Ile Ala Asp Ile Phe Ser Tyr Leu Asn Glu Val Asn
420 425 430

Leu Ser Leu Gln Gly Pro Asn Ser Thr Ile Phe Lys Val Asn Ser Arg
435 440 445

Ile Asn Ser Phe Lys Ser Lys Leu Lys Leu Trp Glu Glu Cys Ile Thr
450 455 460

Lys Asn Asn Thr Lys Cys Phe Ala Asn Leu Asn Asp Phe Leu Glu Thr
465 470 475 480

Ser Asn Thr Ala Leu Asp Pro Asn Leu Lys Ser Asn Ile Leu Glu His
485 490 495

Leu Asn Gly Leu Lys Asn Thr Phe Leu Glu Tyr Phe Pro Pro Thr Cys
500 505 510

Asn Asn Ile Ser Trp Val Glu Asn Pro Phe Asn Glu Cys Gly Asn Val
515 520 525

Asp Thr Leu Pro Ile Lys Glu Arg Glu Gln Leu Ile Asp Ile Arg Thr
530 535 540

Asp Thr Thr Leu Lys Ser Ser Phe Val Pro Asp Gly Ile Gly Pro Phe
545 550 555 560

Trp Ile Lys Leu Met Asp Glu Phe Pro Glu Ile Ser Lys Arg Ala Val
565 570 575

Lys Glu Leu Met Pro Phe Val Thr Thr Tyr Leu Cys Glu Lys Ser Phe
580 585 590

Ser Val Tyr Val Ala Thr Lys Thr Lys Tyr Arg Asn Arg Leu Asp Ala
595 600 605

Glu Asp Asp Met Arg Leu Gln Leu Thr Thr Ile His Pro Asp Ile Asp
610 615 620

Asn Leu Cys Asn Asn Lys Gln Ala Gln Lys Ser His
625 630 635

<210> SEQ ID NO 80
<211> LENGTH: 636
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Met Met Leu Asn Trp Leu Lys Ser Gly Lys Leu Glu Ser Gln Ser Gln
1 5 10 15

Glu Gln Ser Ser Cys Tyr Leu Glu Asn Ser Asn Cys Leu Pro Pro Thr
20 25 30

```
Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Ser Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175

Lys Phe Ala Ser Lys Val Asp Leu Val Pro Leu Ser Ala Thr Thr Ile
            180                 185                 190

Ser Arg Arg Ile Glu Asp Met Ser Tyr Phe Cys Glu Ala Val Leu Val
        195                 200                 205

Asn Arg Leu Lys Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350

Asn Ala Arg Val Phe Ala Leu Leu Cys Asp Asp Leu Gly Ser Leu His
        355                 360                 365

Lys Asn Leu Leu Leu His Thr Glu Thr Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
                405                 410                 415

Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445
```

```
Ile Asn Ser Ile Lys Ser Lys Leu Lys Leu Trp Glu Glu Cys Ile Thr
    450                 455                 460

Lys Asn Asn Thr Lys Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
        515                 520                 525

Asp Thr Leu Pro Ile Lys Glu Arg Glu Gln Leu Ile Asp Ile Arg Thr
    530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Lys Arg Ala Val
                565                 570                 575

Lys Glu Leu Met Pro Phe Val Thr Thr Tyr Leu Cys Glu Lys Ser Phe
            580                 585                 590

Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635


<210> SEQ ID NO 81
<211> LENGTH: 636
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Met Met Leu Asn Trp Leu Lys Ser Gly Lys Leu Glu Ser Gln Ser Gln
1               5                   10                  15

Glu Gln Ser Ser Cys Tyr Leu Glu Asn Ser Asn Cys Leu Pro Pro Thr
            20                  25                  30

Leu Asp Ser Thr Asp Ile Ile Gly Glu Glu Asn Lys Ala Gly Thr Thr
        35                  40                  45

Ser Arg Lys Lys Arg Lys Tyr Asp Glu Asp Tyr Leu Asn Phe Gly Phe
    50                  55                  60

Thr Trp Thr Gly Asp Lys Asp Glu Pro Asn Gly Leu Cys Val Ile Cys
65                  70                  75                  80

Glu Gln Val Val Asn Asn Ser Ser Leu Asn Pro Ala Lys Leu Lys Arg
                85                  90                  95

His Leu Asp Thr Lys His Pro Thr Leu Lys Gly Lys Ser Glu Tyr Phe
            100                 105                 110

Lys Arg Lys Cys Asn Glu Leu Asn Gln Lys Lys His Thr Phe Glu Arg
        115                 120                 125

Tyr Val Arg Asp Asp Asn Lys Asn Leu Leu Lys Ala Ser Tyr Leu Val
    130                 135                 140

Ser Leu Arg Ile Ala Lys Gln Gly Glu Ala Tyr Thr Ile Ala Glu Lys
145                 150                 155                 160

Leu Ile Lys Pro Cys Thr Lys Asp Leu Thr Thr Cys Val Phe Gly Glu
                165                 170                 175
```

```
Lys Phe Ala Ser Lys Val Asp Leu Val Pro Leu Ser Ala Thr Thr Ile
            180                 185                 190

Ser Arg Arg Ile Glu Asp Met Ser Tyr Phe Cys Glu Ala Val Leu Val
        195                 200                 205

Asn Arg Leu Lys Asn Ala Lys Cys Gly Phe Thr Leu Gln Met Asp Glu
    210                 215                 220

Ser Thr Asp Val Ala Gly Leu Ala Ile Leu Leu Val Phe Val Arg Tyr
225                 230                 235                 240

Ile His Glu Ser Ser Phe Glu Glu Asp Met Leu Phe Cys Lys Ala Leu
                245                 250                 255

Pro Thr Gln Thr Thr Gly Glu Glu Ile Phe Asn Leu Leu Asn Ala Tyr
            260                 265                 270

Phe Glu Lys His Ser Ile Pro Trp Asn Leu Cys Tyr His Ile Cys Thr
        275                 280                 285

Asp Gly Ala Lys Ala Met Val Gly Val Ile Lys Gly Val Ile Ala Arg
    290                 295                 300

Ile Lys Lys Leu Val Pro Asp Ile Lys Ala Ser His Cys Cys Leu His
305                 310                 315                 320

Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350

Asn Ala Arg Val Phe Lys Leu Leu Cys Asp Asp Leu Gly Ser Leu His
        355                 360                 365

Lys Asn Leu Leu Leu His Thr Glu Thr Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
                405                 410                 415

Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445

Ile Asn Ser Ile Lys Ser Lys Leu Lys Leu Trp Glu Glu Cys Ile Thr
    450                 455                 460

Lys Asn Asn Thr Lys Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
        515                 520                 525

Asp Thr Leu Pro Ile Lys Glu Arg Glu Gln Leu Ile Asp Ile Arg Thr
    530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Lys Arg Ala Val
                565                 570                 575

Lys Glu Leu Met Pro Phe Val Thr Thr Tyr Leu Cys Glu Lys Ser Phe
            580                 585                 590
```

```
Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635


<210> SEQ ID NO 82
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: a, c, t, or g
<220> FEATURE:
<221> NAME/KEY: misc_feature
<222> LOCATION: (5)..(5)
<223> OTHER INFORMATION: n is a, c, g, or t

<400> SEQUENCE: 82

atgcntagat                                                            10


<210> SEQ ID NO 83
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 2-8 "Gly Gly Gly
      Gly Ser" repeating units

<400> SEQUENCE: 83

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40


<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Gly Gly Gly Gly Gly Gly Gly
1               5


<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85
```

Gly Ser Ala Gly Ser Ala Ala Gly Ser Gly Glu Phe
1 5 10

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gly Gly Gly Gly Ser Gly Gly Gly Gly Ser Gly Gly Gly Gly Ser Gly
1 5 10 15

Gly Gly Gly Ser
20

<210> SEQ ID NO 87
<211> LENGTH: 35
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(35)
<223> OTHER INFORMATION: This sequence may encompass 2-7 “Glu Ala Ala Ala Lys” repeating units

<400> SEQUENCE: 87

Glu Ala Ala Ala Lys Glu Ala Ala Ala Lys Glu Ala Ala Ala Lys Glu
1 5 10 15

Ala Ala Ala Lys Glu Ala Ala Ala Lys Glu Ala Ala Ala Lys Glu Ala
20 25 30

Ala Ala Lys
35

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gly Gly Gly Gly Ser Ser
1 5

<210> SEQ ID NO 89
<211> LENGTH: 7
<212> TYPE: PRT
<213> ORGANISM: Tribolium castaneum

<400> SEQUENCE: 89

Arg His Leu Asp Thr Lys His
1 5

<210> SEQ ID NO 90
<211> LENGTH: 6
<212> TYPE: PRT
<213> ORGANISM: Tribolium castaneum

<400> SEQUENCE: 90

Tyr Val Arg Asp Asp Asn
1 5

<210> SEQ ID NO 91
<211> LENGTH: 7
<212> TYPE: PRT
<213> ORGANISM: Tribolium castaneum

<400> SEQUENCE: 91

Glu Ala Tyr Thr Ile Ala Glu
1 5

<210> SEQ ID NO 92
<211> LENGTH: 6
<212> TYPE: PRT
<213> ORGANISM: Tribolium castaneum

<400> SEQUENCE: 92

Gly Glu Lys Phe Ala Ser
1 5

<210> SEQ ID NO 93
<211> LENGTH: 5
<212> TYPE: PRT
<213> ORGANISM: Tribolium castaneum

<400> SEQUENCE: 93

Leu Ser Asp Thr Thr
1 5

<210> SEQ ID NO 94
<211> LENGTH: 5
<212> TYPE: PRT
<213> ORGANISM: Tribolium castaneum

<400> SEQUENCE: 94

Asp Glu Ser Thr Asp
1 5

<210> SEQ ID NO 95
<211> LENGTH: 5
<212> TYPE: PRT
<213> ORGANISM: Tribolium castaneum

<400> SEQUENCE: 95

Arg Tyr Ile His Glu
1 5

<210> SEQ ID NO 96
<211> LENGTH: 6
<212> TYPE: PRT
<213> ORGANISM: Tribolium castaneum

<400> SEQUENCE: 96

Thr Thr Gly Glu Glu Ile
1 5

<210> SEQ ID NO 97
<211> LENGTH: 7
<212> TYPE: PRT
<213> ORGANISM: Tribolium castaneum

<400> SEQUENCE: 97

Val Arg Trp Leu Ser Arg Gly
1 5

<210> SEQ ID NO 98
<211> LENGTH: 5
<212> TYPE: PRT
<213> ORGANISM: Tribolium castaneum

<400> SEQUENCE: 98

Glu Cys Phe Ala Asn
1 5

<210> SEQ ID NO 99
<211> LENGTH: 5
<212> TYPE: PRT
<213> ORGANISM: Tribolium castaneum

<400> SEQUENCE: 99

Lys Glu Arg Glu Gln
1 5

<210> SEQ ID NO 100
<211> LENGTH: 4
<212> TYPE: PRT
<213> ORGANISM: Tribolium castaneum

<400> SEQUENCE: 100

Thr Lys Thr Lys
1

<210> SEQ ID NO 101
<211> LENGTH: 7
<212> TYPE: PRT
<213> ORGANISM: Zea mays

<400> SEQUENCE: 101

Asn His Leu Arg Thr Ser His
1 5

<210> SEQ ID NO 102
<211> LENGTH: 6
<212> TYPE: PRT
<213> ORGANISM: Zea mays

<400> SEQUENCE: 102

Tyr Lys Tyr Asp Glu Val
1 5

<210> SEQ ID NO 103
<211> LENGTH: 7
<212> TYPE: PRT
<213> ORGANISM: Zea mays

<400> SEQUENCE: 103

Tyr Pro Phe Asn Ile Val Glu
1 5

<210> SEQ ID NO 104
<211> LENGTH: 6
<212> TYPE: PRT
<213> ORGANISM: Zea mays

<400> SEQUENCE: 104

Lys Ser Arg Val Thr Ala
1 5

<210> SEQ ID NO 105
<211> LENGTH: 5
<212> TYPE: PRT
<213> ORGANISM: Zea mays

<400> SEQUENCE: 105

Leu Tyr Leu Glu Glu
1               5

<210> SEQ ID NO 106
<211> LENGTH: 5
<212> TYPE: PRT
<213> ORGANISM: Zea mays

<400> SEQUENCE: 106

Asp Met Trp Thr Ser
1               5

<210> SEQ ID NO 107
<211> LENGTH: 5
<212> TYPE: PRT
<213> ORGANISM: Zea mays

<400> SEQUENCE: 107

His Trp Ile Asp Asp
1               5

<210> SEQ ID NO 108
<211> LENGTH: 6
<212> TYPE: PRT
<213> ORGANISM: Zea mays

<400> SEQUENCE: 108

His Thr Gly Gln Arg Leu
1               5

<210> SEQ ID NO 109
<211> LENGTH: 7
<212> TYPE: PRT
<213> ORGANISM: Zea mays

<400> SEQUENCE: 109

Thr Arg Trp Asn Ser Thr Tyr
1               5

<210> SEQ ID NO 110
<211> LENGTH: 5
<212> TYPE: PRT
<213> ORGANISM: Zea mays

<400> SEQUENCE: 110

Lys Tyr Trp Lys Val
1               5

<210> SEQ ID NO 111
<211> LENGTH: 5
<212> TYPE: PRT
<213> ORGANISM: Zea mays

<400> SEQUENCE: 111

Asn Asp Ser Met Asp
1               5

<210> SEQ ID NO 112
<211> LENGTH: 4

```
<212> TYPE: PRT
<213> ORGANISM: Zea mays

<400> SEQUENCE: 112

Val Val Asp Pro
1


<210> SEQ ID NO 113
<211> LENGTH: 6
<212> TYPE: PRT
<213> ORGANISM: Musca domestica

<400> SEQUENCE: 113

Val Ser Ala Asp Cys Lys
1               5


<210> SEQ ID NO 114
<211> LENGTH: 7
<212> TYPE: PRT
<213> ORGANISM: Musca domestica

<400> SEQUENCE: 114

Arg Pro Phe Ser Ala Val Ser
1               5


<210> SEQ ID NO 115
<211> LENGTH: 6
<212> TYPE: PRT
<213> ORGANISM: Musca domestica

<400> SEQUENCE: 115

Tyr Gly Glu His Val Asn
1               5


<210> SEQ ID NO 116
<211> LENGTH: 5
<212> TYPE: PRT
<213> ORGANISM: Musca domestica

<400> SEQUENCE: 116

Thr Ser Asp Ala Lys
1               5


<210> SEQ ID NO 117
<211> LENGTH: 5
<212> TYPE: PRT
<213> ORGANISM: Musca domestica

<400> SEQUENCE: 117

Asp Leu Trp Thr Asp
1               5


<210> SEQ ID NO 118
<211> LENGTH: 5
<212> TYPE: PRT
<213> ORGANISM: Musca domestica

<400> SEQUENCE: 118

His Tyr His Glu Asn
1               5


<210> SEQ ID NO 119
<211> LENGTH: 6
<212> TYPE: PRT
<213> ORGANISM: Musca domestica
```

<400> SEQUENCE: 119

Ser Thr Ala Glu Asn Ile
1               5

<210> SEQ ID NO 120
<211> LENGTH: 7
<212> TYPE: PRT
<213> ORGANISM: Musca domestica

<400> SEQUENCE: 120

Thr Arg Trp Asn Ser Thr Tyr
1               5

<210> SEQ ID NO 121
<211> LENGTH: 5
<212> TYPE: PRT
<213> ORGANISM: Musca domestica

<400> SEQUENCE: 121

Ile Ile Trp Glu Glu
1               5

<210> SEQ ID NO 122
<211> LENGTH: 5
<212> TYPE: PRT
<213> ORGANISM: Musca domestica

<400> SEQUENCE: 122

His Asn Ser Ile Asp
1               5

<210> SEQ ID NO 123
<211> LENGTH: 4
<212> TYPE: PRT
<213> ORGANISM: Musca domestica

<400> SEQUENCE: 123

Ile Ile Thr Glu
1

<210> SEQ ID NO 124
<211> LENGTH: 6
<212> TYPE: PRT
<213> ORGANISM: Drosophila melanogaster

<400> SEQUENCE: 124

Val Ser Glu Asn Asp Lys
1               5

<210> SEQ ID NO 125
<211> LENGTH: 7
<212> TYPE: PRT
<213> ORGANISM: Drosophila melanogaster

<400> SEQUENCE: 125

Arg Pro Phe Ser Ala Val Thr
1               5

<210> SEQ ID NO 126
<211> LENGTH: 6
<212> TYPE: PRT
<213> ORGANISM: Drosophila melanogaster

<400> SEQUENCE: 126

Tyr Gly Glu Gln Val Asp
1 5

<210> SEQ ID NO 127
<211> LENGTH: 5
<212> TYPE: PRT
<213> ORGANISM: Drosophila melanogaster

<400> SEQUENCE: 127

Thr Ser Asp Ala Glu
1 5

<210> SEQ ID NO 128
<211> LENGTH: 5
<212> TYPE: PRT
<213> ORGANISM: Drosophila melanogaster

<400> SEQUENCE: 128

Asp Met Trp Thr Asp
1 5

<210> SEQ ID NO 129
<211> LENGTH: 5
<212> TYPE: PRT
<213> ORGANISM: Drosophila melanogaster

<400> SEQUENCE: 129

His Tyr Glu Lys Glu
1 5

<210> SEQ ID NO 130
<211> LENGTH: 6
<212> TYPE: PRT
<213> ORGANISM: Drosophila melanogaster

<400> SEQUENCE: 130

Ser Thr Ala Glu Asn Ile
1 5

<210> SEQ ID NO 131
<211> LENGTH: 7
<212> TYPE: PRT
<213> ORGANISM: Drosophila melanogaster

<400> SEQUENCE: 131

Thr Arg Trp Asn Ser Asn Tyr
1 5

<210> SEQ ID NO 132
<211> LENGTH: 5
<212> TYPE: PRT
<213> ORGANISM: Drosophila melanogaster

<400> SEQUENCE: 132

Lys Ile Trp Met Ala
1 5

<210> SEQ ID NO 133
<211> LENGTH: 5
<212> TYPE: PRT
<213> ORGANISM: Drosophila melanogaster

<400> SEQUENCE: 133

Pro Glu Ser Leu Glu 1 5

<210> SEQ ID NO 134
<211> LENGTH: 4
<212> TYPE: PRT
<213> ORGANISM: Drosophila melanogaster

<400> SEQUENCE: 134

Ile Ile Thr Glu
1

<210> SEQ ID NO 135
<211> LENGTH: 7
<212> TYPE: PRT
<213> ORGANISM: Arabidopsis thaliana

<400> SEQUENCE: 135

Arg His Met Arg Ser Cys Glu
1 5

<210> SEQ ID NO 136
<211> LENGTH: 5
<212> TYPE: PRT
<213> ORGANISM: Arabidopsis thaliana

<400> SEQUENCE: 136

Lys Val Asp Met Met
1 5

<210> SEQ ID NO 137
<211> LENGTH: 7
<212> TYPE: PRT
<213> ORGANISM: Arabidopsis thaliana

<400> SEQUENCE: 137

Leu Pro Tyr Ser Phe Val Glu
1 5

<210> SEQ ID NO 138
<211> LENGTH: 6
<212> TYPE: PRT
<213> ORGANISM: Arabidopsis thaliana

<400> SEQUENCE: 138

Trp Ser Arg Asn Thr Ala
1 5

<210> SEQ ID NO 139
<211> LENGTH: 5
<212> TYPE: PRT
<213> ORGANISM: Arabidopsis thaliana

<400> SEQUENCE: 139

Ile Tyr Glu Arg Glu
1 5

<210> SEQ ID NO 140
<211> LENGTH: 5
<212> TYPE: PRT
<213> ORGANISM: Arabidopsis thaliana

<400> SEQUENCE: 140

Asp Leu Trp Arg Ala
1 5

<210> SEQ ID NO 141
<211> LENGTH: 5
<212> TYPE: PRT
<213> ORGANISM: Arabidopsis thaliana

<400> SEQUENCE: 141

His Tyr Val Asp Val
1               5

<210> SEQ ID NO 142
<211> LENGTH: 6
<212> TYPE: PRT
<213> ORGANISM: Arabidopsis thaliana

<400> SEQUENCE: 142

His Ser Gly Val Ala Ile
1               5

<210> SEQ ID NO 143
<211> LENGTH: 7
<212> TYPE: PRT
<213> ORGANISM: Arabidopsis thaliana

<400> SEQUENCE: 143

Thr Arg Trp Asn Ser Thr Tyr
1               5

<210> SEQ ID NO 144
<211> LENGTH: 5
<212> TYPE: PRT
<213> ORGANISM: Arabidopsis thaliana

<400> SEQUENCE: 144

Lys Tyr Trp Glu Asp
1               5

<210> SEQ ID NO 145
<211> LENGTH: 5
<212> TYPE: PRT
<213> ORGANISM: Arabidopsis thaliana

<400> SEQUENCE: 145

Gln Ser Ser Arg Lys
1               5

<210> SEQ ID NO 146
<211> LENGTH: 4
<212> TYPE: PRT
<213> ORGANISM: Arabidopsis thaliana

<400> SEQUENCE: 146

Val Leu Asn Lys
1

<210> SEQ ID NO 147
<211> LENGTH: 7
<212> TYPE: PRT
<213> ORGANISM: Antirrhinum majus

<400> SEQUENCE: 147

Arg His Leu Thr Ala Lys His
1               5

<210> SEQ ID NO 148

<211> LENGTH: 6
<212> TYPE: PRT
<213> ORGANISM: Antirrhinum majus

<400> SEQUENCE: 148

Trp Arg Tyr Asp Gln Asn
1 5

<210> SEQ ID NO 149
<211> LENGTH: 7
<212> TYPE: PRT
<213> ORGANISM: Antirrhinum majus

<400> SEQUENCE: 149

Leu Pro Phe Ser Phe Ala Gln
1 5

<210> SEQ ID NO 150
<211> LENGTH: 6
<212> TYPE: PRT
<213> ORGANISM: Antirrhinum majus

<400> SEQUENCE: 150

Ile Ser Arg Ala Thr Cys
1 5

<210> SEQ ID NO 151
<211> LENGTH: 5
<212> TYPE: PRT
<213> ORGANISM: Antirrhinum majus

<400> SEQUENCE: 151

Gln Tyr Glu Lys Glu
1 5

<210> SEQ ID NO 152
<211> LENGTH: 5
<212> TYPE: PRT
<213> ORGANISM: Antirrhinum majus

<400> SEQUENCE: 152

Asp Leu Trp Gln Gly
1 5

<210> SEQ ID NO 153
<211> LENGTH: 5
<212> TYPE: PRT
<213> ORGANISM: Antirrhinum majus

<400> SEQUENCE: 153

His Trp Ile Asp Lys
1 5

<210> SEQ ID NO 154
<211> LENGTH: 6
<212> TYPE: PRT
<213> ORGANISM: Antirrhinum majus

<400> SEQUENCE: 154

His Asn Gly Asp Cys Ile
1 5

<210> SEQ ID NO 155
<211> LENGTH: 7
<212> TYPE: PRT

<213> ORGANISM: Antirrhinum majus

<400> SEQUENCE: 155

His Arg Trp Asn Ala Thr Tyr
1               5

<210> SEQ ID NO 156
<211> LENGTH: 5
<212> TYPE: PRT
<213> ORGANISM: Antirrhinum majus

<400> SEQUENCE: 156

Lys Tyr Tyr Lys Lys
1               5

<210> SEQ ID NO 157
<211> LENGTH: 5
<212> TYPE: PRT
<213> ORGANISM: Antirrhinum majus

<400> SEQUENCE: 157

Asn Ala Ser Arg Gly
1               5

<210> SEQ ID NO 158
<211> LENGTH: 4
<212> TYPE: PRT
<213> ORGANISM: Antirrhinum majus

<400> SEQUENCE: 158

Val Leu Thr Asp
1

<210> SEQ ID NO 159
<211> LENGTH: 7
<212> TYPE: PRT
<213> ORGANISM: Anopheles gambiae

<400> SEQUENCE: 159

Arg His Leu Asn Leu Val His
1               5

<210> SEQ ID NO 160
<211> LENGTH: 6
<212> TYPE: PRT
<213> ORGANISM: Anopheles gambiae

<400> SEQUENCE: 160

Ile Asn Ser Glu Thr Lys
1               5

<210> SEQ ID NO 161
<211> LENGTH: 7
<212> TYPE: PRT
<213> ORGANISM: Anopheles gambiae

<400> SEQUENCE: 161

Leu Pro Phe Asn Leu Val Glu
1               5

<210> SEQ ID NO 162
<211> LENGTH: 6
<212> TYPE: PRT
<213> ORGANISM: Anopheles gambiae

<400> SEQUENCE: 162

Pro Thr Arg Lys Ser Leu
1               5

<210> SEQ ID NO 163
<211> LENGTH: 5
<212> TYPE: PRT
<213> ORGANISM: Anopheles gambiae

<400> SEQUENCE: 163

Val Tyr Asn Gln Glu
1               5

<210> SEQ ID NO 164
<211> LENGTH: 5
<212> TYPE: PRT
<213> ORGANISM: Anopheles gambiae

<400> SEQUENCE: 164

Asp Gly Trp Thr Asn
1               5

<210> SEQ ID NO 165
<211> LENGTH: 5
<212> TYPE: PRT
<213> ORGANISM: Anopheles gambiae

<400> SEQUENCE: 165

His Tyr Ile Asp Glu
1               5

<210> SEQ ID NO 166
<211> LENGTH: 6
<212> TYPE: PRT
<213> ORGANISM: Anopheles gambiae

<400> SEQUENCE: 166

His Ser Gly Arg Asn Ile
1               5

<210> SEQ ID NO 167
<211> LENGTH: 7
<212> TYPE: PRT
<213> ORGANISM: Anopheles gambiae

<400> SEQUENCE: 167

Thr Arg Trp Asn Ser Gly Tyr
1               5

<210> SEQ ID NO 168
<211> LENGTH: 5
<212> TYPE: PRT
<213> ORGANISM: Anopheles gambiae

<400> SEQUENCE: 168

Lys Ile Tyr Arg Ser
1               5

<210> SEQ ID NO 169
<211> LENGTH: 5
<212> TYPE: PRT
<213> ORGANISM: Anopheles gambiae

<400> SEQUENCE: 169

Lys Val Ser Lys Asp
1 5

<210> SEQ ID NO 170
<211> LENGTH: 4
<212> TYPE: PRT
<213> ORGANISM: Anopheles gambiae

<400> SEQUENCE: 170

Ile Tyr Ser Glu
1

<210> SEQ ID NO 171
<211> LENGTH: 7
<212> TYPE: PRT
<213> ORGANISM: Tolypocladium inflatum

<400> SEQUENCE: 171

Lys His Leu Arg Asp Ile His
1 5

<210> SEQ ID NO 172
<211> LENGTH: 6
<212> TYPE: PRT
<213> ORGANISM: Tolypocladium inflatum

<400> SEQUENCE: 172

Ile Leu Gly Arg Leu Lys
1 5

<210> SEQ ID NO 173
<211> LENGTH: 7
<212> TYPE: PRT
<213> ORGANISM: Tolypocladium inflatum

<400> SEQUENCE: 173

Leu Pro Phe Arg Leu Ile Glu
1 5

<210> SEQ ID NO 174
<211> LENGTH: 6
<212> TYPE: PRT
<213> ORGANISM: Tolypocladium inflatum

<400> SEQUENCE: 174

Tyr Lys Asp Lys Val Pro
1 5

<210> SEQ ID NO 175
<211> LENGTH: 5
<212> TYPE: PRT
<213> ORGANISM: Tolypocladium inflatum

<400> SEQUENCE: 175

Ile Tyr Asn Gly Ala
1 5

<210> SEQ ID NO 176
<211> LENGTH: 5
<212> TYPE: PRT
<213> ORGANISM: Tolypocladium inflatum

<400> SEQUENCE: 176

Asp Gly Trp Thr Ser
1 5

<210> SEQ ID NO 177
<211> LENGTH: 5
<212> TYPE: PRT
<213> ORGANISM: Tolypocladium inflatum

<400> SEQUENCE: 177

Phe Phe Val Asp Gln
1               5

<210> SEQ ID NO 178
<211> LENGTH: 6
<212> TYPE: PRT
<213> ORGANISM: Tolypocladium inflatum

<400> SEQUENCE: 178

His Thr Gly Asp Asn Leu
1               5

<210> SEQ ID NO 179
<211> LENGTH: 7
<212> TYPE: PRT
<213> ORGANISM: Tolypocladium inflatum

<400> SEQUENCE: 179

Thr Arg Trp Asn Ser Arg His
1               5

<210> SEQ ID NO 180
<211> LENGTH: 5
<212> TYPE: PRT
<213> ORGANISM: Tolypocladium inflatum

<400> SEQUENCE: 180

Glu Tyr Tyr Asp Lys
1               5

<210> SEQ ID NO 181
<211> LENGTH: 5
<212> TYPE: PRT
<213> ORGANISM: Tolypocladium inflatum

<400> SEQUENCE: 181

Ala Ser Ser Arg Thr
1               5

<210> SEQ ID NO 182
<211> LENGTH: 4
<212> TYPE: PRT
<213> ORGANISM: Tolypocladium inflatum

<400> SEQUENCE: 182

Met Val Ser Pro
1

<210> SEQ ID NO 183
<211> LENGTH: 7
<212> TYPE: PRT
<213> ORGANISM: Oryzias latipes

<400> SEQUENCE: 183

Lys His Ile Glu Arg Met His
1               5

<210> SEQ ID NO 184
<211> LENGTH: 6
<212> TYPE: PRT
<213> ORGANISM: Oryzias latipes

<400> SEQUENCE: 184

Val Lys His Val Ser Pro
1               5

<210> SEQ ID NO 185
<211> LENGTH: 7
<212> TYPE: PRT
<213> ORGANISM: Oryzias latipes

<400> SEQUENCE: 185

His Pro Phe Ser Thr Val Asp
1               5

<210> SEQ ID NO 186
<211> LENGTH: 6
<212> TYPE: PRT
<213> ORGANISM: Oryzias latipes

<400> SEQUENCE: 186

Ile Thr Arg Pro Thr Leu
1               5

<210> SEQ ID NO 187
<211> LENGTH: 5
<212> TYPE: PRT
<213> ORGANISM: Oryzias latipes

<400> SEQUENCE: 187

Ala Ala Leu Ile Met
1               5

<210> SEQ ID NO 188
<211> LENGTH: 5
<212> TYPE: PRT
<213> ORGANISM: Oryzias latipes

<400> SEQUENCE: 188

Asp Cys Trp Thr Ala
1               5

<210> SEQ ID NO 189
<211> LENGTH: 5
<212> TYPE: PRT
<213> ORGANISM: Oryzias latipes

<400> SEQUENCE: 189

His Trp Ile Asn Pro
1               5

<210> SEQ ID NO 190
<211> LENGTH: 6
<212> TYPE: PRT
<213> ORGANISM: Oryzias latipes

<400> SEQUENCE: 190

His Thr Phe Glu Val Leu
1               5

<210> SEQ ID NO 191
<211> LENGTH: 7

<212> TYPE: PRT
<213> ORGANISM: Oryzias latipes

<400> SEQUENCE: 191

Thr Arg Trp Asn Ser Thr Phe
1 5

<210> SEQ ID NO 192
<211> LENGTH: 5
<212> TYPE: PRT
<213> ORGANISM: Oryzias latipes

<400> SEQUENCE: 192

Arg Phe Lys His Met
1 5

<210> SEQ ID NO 193
<211> LENGTH: 5
<212> TYPE: PRT
<213> ORGANISM: Oryzias latipes

<400> SEQUENCE: 193

Ser Ser Ser Asp Asp
1 5

<210> SEQ ID NO 194
<211> LENGTH: 4
<212> TYPE: PRT
<213> ORGANISM: Oryzias latipes

<400> SEQUENCE: 194

Leu Phe Ser Pro
1

<210> SEQ ID NO 195
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 195

Asp Lys Asp Glu Pro Asn Gly Leu Cys Val Ile Cys Glu Gln Val Val
1 5 10 15

Asn Asn Ser Ser Leu Asn Pro Ala Lys Leu Lys Arg His Leu Asp Thr
20 25 30

Lys His Pro Thr Leu Lys Gly Lys Ser
35 40

<210> SEQ ID NO 196
<211> LENGTH: 41
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 196

Phe Glu Arg Tyr Val Arg Asp Asp Asn Lys Asn Leu Leu Lys Ala Ser
1 5 10 15

Tyr Leu Val Ser Leu Arg Ile Ala Lys Gln Gly Glu Ala Tyr Thr Ile
20 25 30

Ala Glu Lys Leu Ile Lys Pro Cys Thr 35 40

<210> SEQ ID NO 197
<211> LENGTH: 139
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 197

Arg Arg Ile Glu Asp Met Ser Tyr Phe Cys Glu Ala Val Leu Val Asn
1 5 10 15

Arg Leu Lys Asn Ala Lys Cys Gly Phe Thr Leu Gln Met Asp Glu Ser
20 25 30

Thr Asp Val Ala Gly Leu Ala Ile Leu Leu Val Phe Val Arg Tyr Ile
35 40 45

His Glu Ser Ser Phe Glu Glu Asp Met Leu Phe Cys Lys Ala Leu Pro
50 55 60

Thr Gln Thr Thr Gly Glu Glu Ile Phe Asn Leu Leu Asn Ala Tyr Phe
65 70 75 80

Glu Lys His Ser Ile Pro Trp Asn Leu Cys Tyr His Ile Cys Thr Asp
85 90 95

Gly Ala Lys Ala Met Val Gly Val Ile Lys Gly Val Ile Ala Arg Ile
100 105 110

Lys Lys Leu Val Pro Asp Ile Lys Ala Ser His Cys Cys Leu His Arg
115 120 125

His Ala Leu Ala Val Lys Arg Ile Pro Asn Ala
130 135

<210> SEQ ID NO 198
<211> LENGTH: 63
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 198

Ala Val Lys Met Ile Asn Phe Ile Lys Ser Arg Pro Leu Asn Ala Arg
1 5 10 15

Val Phe Ala Leu Leu Cys Asp Asp Leu Gly Ser Leu His Lys Asn Leu
20 25 30

Leu Leu His Thr Glu Val Arg Trp Leu Ser Arg Gly Lys Val Leu Thr
35 40 45

Arg Phe Trp Glu Leu Arg Asp Glu Ile Arg Ile Phe Phe Asn Glu
50 55 60

<210> SEQ ID NO 199
<211> LENGTH: 31
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 199

Asn Leu Ala Tyr Ile Ala Asp Ile Phe Ser Tyr Leu Asn Glu Val Asn
1 5 10 15

Leu Ser Leu Gln Gly Pro Asn Ser Thr Ile Phe Lys Val Asn Ser
20 25 30

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 200

Asn Ser Ile Lys Ser Lys Leu
1 5

<210> SEQ ID NO 201
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Ile Ser Trp Val Glu Asn Pro
1 5

<210> SEQ ID NO 202
<211> LENGTH: 62
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 202

Ile Arg Thr Asp Thr Thr Leu Lys Ser Ser Phe Val Pro Asp Gly Ile
1 5 10 15

Gly Pro Phe Trp Ile Lys Leu Met Asp Glu Phe Pro Glu Ile Ser Lys
20 25 30

Arg Ala Val Lys Glu Leu Met Pro Phe Val Thr Thr Tyr Leu Cys Glu
35 40 45

Lys Ser Phe Ser Val Tyr Val Ala Thr Lys Thr Lys Tyr Arg
50 55 60

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 203

Gln Leu Thr Thr Ile His Pro
1 5

<210> SEQ ID NO 204
<211> LENGTH: 1908
<212> TYPE: DNA
<213> ORGANISM: Tribolium castaneum

<400> SEQUENCE: 204
atgatgctga attggctgaa gagcggcaag ctggagtcac agtcacagga acagtcctca 60
tgttatctgg agaacagtaa ttgtctgccc cctaccctgg actctacaga tatcatcggc 120
gaggagaata aggccggcac cacaagccgg aagaagagaa agtacgacga ggattatctg 180

```
aatttcggct ttacctggac aggcgacaag gatgagccaa acggcctgtg cgtgatctgt    240
gagcaggtgg tgaacaatag ctccctgaac ccagccaagc tgaagcggca cctggacacc    300
aagcacccca cactgaaggg caagagcgag tactttaaga gaaagtgcaa cgagctgaat    360
cagaagaagc acaccttcga gaggtacgtg cgcgacgata acaagaatct gctgaaggcc    420
tcctatctgg tgtctctgag aatcgccaag cagggcgagg cctacaccat cgccgagaag    480
ctgatcaagc catgcacaaa ggacctgacc acatgcgtgt tcggcgagaa gtttgccagc    540
aaggtggacc tggtgcccct gagcgatacc acaatctccc ggagaatcga ggatatgtcc    600
tatttttgcg aggccgtgct ggtgaacagg ctgaagaatg ccaagtgtgg cttcaccctg    660
cagatggacg agtccacaga tgtggccggc ctggccatcc tgctggtgtt tgtgcgctac    720
atccacgagt ctagcttcga ggaggacatg ctgttttgca aggccctgcc tacccagacc    780
acaggcgagg agatcttcaa cctgctgaat gcctactttg agaagcactc tatcccatgg    840
aacctgtgct atcacatctg taccgacgga gcaaaggcaa tggtgggcgt gatcaagggc    900
gtgatcgcca ggatcaagaa gctggtgccc gatatcaagg cctctcactg ctgtctgcac    960
aggcacgcac tggcagtgaa gaggatccct aacgccctgc acgaggtgct gaatgacgcc   1020
gtgaagatga tcaactttat caagagccgg cctctgaatg ccagagtgtt cgccctgctg   1080
tgcgacgatc tgggctccct gcacaagaac ctgctgctgc acaccgaggt tcggtggctg   1140
tctagaggca aggtgctgac caggttttgg gagctgaggg atgagatccg catcttcttt   1200
aatgagcgcg agttcgccgg caagctgaat gacacaagct ggctgcagaa cctggcctac   1260
atcgccgata tcttttccta tctgaacgaa gtgaatctgt ctctgcaggg ccccaacagc   1320
accatcttca aggtgaactc ccgcatcaat tctatcaaga gcaagctgaa gctgtgggag   1380
gagtgcatca ccaagaacaa tacagagtgt ttcgccaacc tgaatgactt cctggagaca   1440
agcaatacag ccctggatcc taacctgaag tctaatatcc tggagcacct gaacggcctg   1500
aagaatacct tcctggagta ttttccaccc acatgcaaca atatcagctg ggtggagaac   1560
cccttcaatg agtgtggcaa cgtggacacc ctgcctatca aggagcggga gcagctgatc   1620
gacatcagaa cagataccac actgaagtcc tctttcgtgc ctgacggcat cggcccattt   1680
tggatcaagc tgatggatga gttccctgag atctccaagc gggccgtgaa ggagctgatg   1740
ccatttgtga ccacatacct gtgcgagaag agcttctccg tgtacgtggc caccaagaca   1800
aagtatagga accgcctgga tgccgaggac gatatgagac tgcagctgac cactatccat   1860
cccgacattg acaacctgtg caacaacaaa caggcccaga aatcccat                 1908
```

<210> SEQ ID NO 205
<211> LENGTH: 253
<212> TYPE: DNA
<213> ORGANISM: Artificial sequence
<220> FEATURE:
<223> OTHER INFORMATION: Synthetic

<400> SEQUENCE: 205

```
cagtgttctt caacctttgc catccggcgg aaccctttgt cgagatattt ttttttatgg     60
aacccttcat ttagtaatac acccagatga gattttaggg acagctgcgt tgacttgtta    120
cgaacaaggt gagcccgtgc tttggtaata aaaactctaa ataagattta aatttgcatt    180
tatttaaaca aactttaaac aaaaagataa atattccaaa taaaataata tataaaataa    240
aaaataaaaa tta                                                       253
```

<210> SEQ ID NO 206
<211> LENGTH: 328
<212> TYPE: DNA
<213> ORGANISM: Artificial sequence
<220> FEATURE:
<223> OTHER INFORMATION: Synthetic

<400> SEQUENCE: 206
atttctgaac gattctaggt taggatcaaa caaaatacaa tttattttaa aactgtaagt 60
taacttacct ttgcttgtct aaacctaaaa caacaacaaa actacgacca caagtacagt 120
tacatatttt tgaaaattaa ggttaagtgc agtgtaagtc aactatgcga atggataaca 180
tgtttcaaca tgaaactccg attgacgcat gtgcattctg aagagcggcg cggccgacgt 240
ctctcgaatt gaagcaatga ctcgcggaac cccgaaagcc tttgggtgga accctagggt 300
tccgcggaac acaggttgaa gaacactg 328

<210> SEQ ID NO 207
<211> LENGTH: 1911
<212> TYPE: RNA
<213> ORGANISM: Tribolium castaneum

<400> SEQUENCE: 207
augaugcuga auuggcugaa gagcggcaag cuggagucac agucacagga acaguccuca 60
uguuaucugg agaacaguaa uugucugccc ccuacccugg acucuacaga uaucaucggc 120
gaggagaaua aggccggcac cacaagccgg aagaagagaa aguacgacga ggauuaucug 180
aauuucggcu uuaccuggac aggcgacaag gaugagccaa acggccugug cgugaucugu 240
gagcaggugg ugaacaauag cucccugaac ccagccaagc ugaagcggca ccuggacacc 300
aagcacccca cacugaaggg caagagcgag uacuuuaaga gaaagugcaa cgagcugaau 360
cagaagaagc acaccuucga gagguacgug cgcgacgaua acaagaaucu gcugaaggcc 420
uccuaucugg ugucucugag aaucgccaag cagggcgagg ccuacaccau cgccgagaag 480
cugaucaagc caugcacaaa ggaccugacc acaugcgugu ucggcgagaa guuugccagc 540
aagguggacc uggugccccu gagcgauacc acaaucuccc ggagaaucga ggauaugucc 600
uauuuuugcg aggccgugcu ggugaacagg cugaagaaug ccaagugugg cuucacccug 660
cagauggacg aguccacaga uguggccggc cuggccaucc ugcuggugu ugugcgcuac 720 auccacgagu cuagcuucga ggaggacaug cuguuuugca aggcccugcc uacccagacc 780
acaggcgagg agaucuucaa ccugcugaau gccuacuuug agaagcacuc uaucccaugg 840
aaccugugcu aucacaucug uaccgacgga gcaaaggcaa uggugggcgu gaucaagggc 900
gugaucgcca ggaucaagaa gcuggugccc gauaucaagg ccucucacug cugucugcac 960
aggcacgcac uggcagugaa gaggaucccu aacgcccugc acgaggugcu gaaugacgcc 1020
gugaagauga ucaacuuuau caagagccgg ccucugaaug ccagaguguu cgcccugcug 1080
ugcgacgauc ugggcucccu gcacaagaac cugcugcugc acaccgaggu ucgguggcug 1140
ucuagaggca aggugcugac cagguuuugg gagcugaggg augagauccg caucuucuuu 1200
aaugagcgcg aguucgccgg caagcugaau gacacaagcu ggcugcagaa ccuggccuac 1260
aucgccgaua ucuuuuccua ucugaacgaa gugaaucugu cucugcaggg ccccaacagc 1320
accaucuuca aggugaacuc ccgcaucaau ucuaucaaga gcaagcugaa gcugugggag 1380
gagugcauca ccaagaacaa uacagagugu uucgccaacc ugaaugacuu ccuggagaca 1440
agcaauacag cccuggaucc uaaccugaag ucuaauaucc uggagcaccu gaacggccug 1500

```
aagaauaccu uccuggagua uuuuccaccc acaugcaaca auaucagcug gguggagaac   1560

cccuucaaug aguguggcaa cguggacacc cugccuauca aggagcggga gcagcugauc   1620

gacaucagaa cagauaccac acugaagucc ucuuucgugc cugacggcau cggcccauuu   1680

uggaucaagc ugauggauga guucccugag aucuccaagc gggccgugaa ggagcugaug   1740

ccauuuguga ccacauaccu gugcgagaag agcuucuccg uguacguggc caccaagaca   1800

aaguauagga accgccugga ugccgaggac gauaugagac ugcagcugac cacuauccau   1860

cccgacauug acaaccugug caacaacaaa caggcccaga aaucccauug a            1911


<210> SEQ ID NO 208
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = K or R
<220> FEATURE:
<221> NAME/KEY: misc_feature
<222> LOCATION: (3)..(14)
<223> OTHER INFORMATION: Xaa can be any naturally occurring amino acid
<220> FEATURE:
<221> NAME/KEY: MISC_FEATURE
<222> LOCATION: (15)..(18)
<223> OTHER INFORMATION: X = K or R

<400> SEQUENCE: 208

Lys Xaa Xaa Xaa Xaa Xaa Xaa Xaa Xaa Xaa Xaa Xaa Xaa Xaa Xaa Xaa
1               5                   10                  15

Xaa Xaa


<210> SEQ ID NO 209
<211> LENGTH: 17
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X = K or R
<220> FEATURE:
<221> NAME/KEY: misc_feature
<222> LOCATION: (3)..(13)
<223> OTHER INFORMATION: Xaa can be any naturally occurring amino acid
<220> FEATURE:
<221> NAME/KEY: MISC_FEATURE
<222> LOCATION: (14)..(17)
<223> OTHER INFORMATION: X = K or R

<400> SEQUENCE: 209

Lys Xaa Xaa Xaa Xaa Xaa Xaa Xaa Xaa Xaa Xaa Xaa Xaa Xaa Xaa Xaa
1               5                   10                  15

Xaa


<210> SEQ ID NO 210
<211> LENGTH: 16
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
```

<223> OTHER INFORMATION: X= K or R
<220> FEATURE:
<221> NAME/KEY: misc_feature
<222> LOCATION: (3)..(12)
<223> OTHER INFORMATION: Xaa can be any naturally occurring amino acid
<220> FEATURE:
<221> NAME/KEY: MISC_FEATURE
<222> LOCATION: (13)..(16)
<223> OTHER INFORMATION: X= K or R

<400> SEQUENCE: 210

Lys Xaa Xaa Xaa Xaa Xaa Xaa Xaa Xaa Xaa Xaa Xaa Xaa Xaa Xaa Xaa
1 5 10 15

<210> SEQ ID NO 211
<211> LENGTH: 15
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X= K or R
<220> FEATURE:
<221> NAME/KEY: misc_feature
<222> LOCATION: (3)..(11)
<223> OTHER INFORMATION: Xaa can be any naturally occurring amino acid
<220> FEATURE:
<221> NAME/KEY: MISC_FEATURE
<222> LOCATION: (12)..(15)
<223> OTHER INFORMATION: X= K or R

<400> SEQUENCE: 211

Lys Xaa Xaa Xaa Xaa Xaa Xaa Xaa Xaa Xaa Xaa Xaa Xaa Xaa Xaa
1 5 10 15

<210> SEQ ID NO 212
<211> LENGTH: 14
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X= K or R
<220> FEATURE:
<221> NAME/KEY: misc_feature
<222> LOCATION: (3)..(10)
<223> OTHER INFORMATION: Xaa can be any naturally occurring amino acid
<220> FEATURE:
<221> NAME/KEY: MISC_FEATURE
<222> LOCATION: (11)..(14)
<223> OTHER INFORMATION: X= K or R

<400> SEQUENCE: 212

Lys Xaa Xaa Xaa Xaa Xaa Xaa Xaa Xaa Xaa Xaa Xaa Xaa Xaa
1 5 10

<210> SEQ ID NO 213
<211> LENGTH: 13
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X= K or R
<220> FEATURE:
<221> NAME/KEY: misc_feature
<222> LOCATION: (3)..(9)

<223> OTHER INFORMATION: Xaa can be any naturally occurring amino acid
<220> FEATURE:
<221> NAME/KEY: MISC_FEATURE
<222> LOCATION: (10)..(13)
<223> OTHER INFORMATION: X= K or R

<400> SEQUENCE: 213

Lys Xaa Xaa Xaa Xaa Xaa Xaa Xaa Xaa Xaa Xaa Xaa Xaa
1               5                   10

<210> SEQ ID NO 214
<211> LENGTH: 7
<212> TYPE: PRT
<213> ORGANISM: Artificial sequence
<220> FEATURE:
<223> OTHER INFORMATION: Synthetic

<400> SEQUENCE: 214

Pro Lys Lys Lys Arg Lys Val
1               5

<210> SEQ ID NO 215
<211> LENGTH: 20
<212> TYPE: PRT
<213> ORGANISM: Artificial sequence
<220> FEATURE:
<223> OTHER INFORMATION: Synthetic

<400> SEQUENCE: 215

Ala Val Lys Arg Pro Ala Ala Thr Lys Lys Ala Gly Gln Ala Lys Lys
1               5                   10                  15

Lys Lys Leu Asp
            20

<210> SEQ ID NO 216
<211> LENGTH: 9
<212> TYPE: PRT
<213> ORGANISM: Artificial sequence
<220> FEATURE:
<223> OTHER INFORMATION: Synthetic

<400> SEQUENCE: 216

Pro Ala Ala Lys Arg Val Lys Leu Asp
1               5

<210> SEQ ID NO 217
<211> LENGTH: 17
<212> TYPE: PRT
<213> ORGANISM: Artificial sequence
<220> FEATURE:
<223> OTHER INFORMATION: Synthetic

<400> SEQUENCE: 217

Lys Arg Pro Ala Glu Asp Met Glu Glu Glu Gln Ala Phe Lys Arg Ser
1               5                   10                  15

Arg

<210> SEQ ID NO 218
<211> LENGTH: 12
<212> TYPE: PRT
<213> ORGANISM: Artificial sequence
<220> FEATURE:
<223> OTHER INFORMATION: Synthetic

<400> SEQUENCE: 218

Gly Arg Lys Lys Arg Arg Gln Arg Arg Arg Ala Pro

-continued

```
1               5                   10


<210> SEQ ID NO 219
<211> LENGTH: 4
<212> TYPE: PRT
<213> ORGANISM: Artificial sequence
<220> FEATURE:
<223> OTHER INFORMATION: Synthetic

<400> SEQUENCE: 219

Lys Arg Pro Arg
1


<210> SEQ ID NO 220
<211> LENGTH: 42
<212> TYPE: PRT
<213> ORGANISM: Artificial sequence
<220> FEATURE:
<223> OTHER INFORMATION: Synthetic

<400> SEQUENCE: 220

Gly Asn Tyr Asn Asn Gln Ser Ser Asn Phe Gly Pro Met Lys Gly Gly
1               5                   10                  15

Asn Phe Gly Gly Arg Ser Ser Gly Pro Tyr Gly Gly Gly Gly Gln Tyr
            20                  25                  30

Phe Ala Lys Pro Arg Asn Gln Gly Gly Tyr
        35                  40
```

ENHANCED HAT FAMILY TRANSPOSON-MEDIATED GENE TRANSFER AND ASSOCIATED COMPOSITIONS, SYSTEMS, AND METHODS

CROSS-REFERENCE

This application is a continuation-in-part application of U.S. application Ser. No. 15/844,363, filed Dec. 15, 2017, which claims the benefit of U.S. Provisional Application No. 62/435,522, filed Dec. 16, 2016, each of which is incorporated herein by reference in its entirety. This application also claims the benefit of U.S. Provisional Application No. 62/688,278, filed Jun. 21, 2018, which is incorporated herein by reference in its entirety.

SEQUENCE LISTING

The text of the computer readable sequence listing filed herewith, titled "37964-253_SEQUENCE_LISTING_ST25", created Dec. 17, 2020, having a file size of 101,371 bytes, is hereby incorporated by reference in its entirety.

BACKGROUND

Transposable genetic elements, also called transposons, are segments of DNA that can be mobilized from one genomic location to another within a single cell. Transposons can be divided into two major groups according to their mechanism of transposition: transposition can occur (1) via reverse transcription of an RNA intermediate for elements termed retrotransposons, and (2) via direct transposition of DNA flanked by terminal inverted repeats (TIRs) for DNA transposons. Active transposons encode one or more proteins that are required for transposition. The natural active DNA transposons harbor a transposase enzyme gene.

DNA transposons in the hAT family are widespread in plants and animals. A number of active hAT transposon systems have been identified and found to be functional, including but not limited to, the Hermes transposon, Ac transposon, hobo transposon, and the Tol2 transposon. The hAT family is composed of two families that have been classified as the AC subfamily and the Buster subfamily, based on the primary sequence of their transposases. Members of the hAT family belong to Class II transposable elements. Class II mobile elements use a cut and paste mechanism of transposition. hAT elements share similar transposases, short terminal inverted repeats, and an eight base-pairs duplication of genomic target.

SUMMARY

Described herein, in one aspect, is a mutant TcBuster transposase comprising an amino acid sequence at least 70% identical to full-length SEQ ID NO: 1 and having one or more amino acid substitutions from Table 1.1. In some embodiments, the mutant TcBuster transposase comprises an amino acid substitution that increases a net charge at a neutral pH in comparison to SEQ ID NO: 1. In some embodiments, the amino acid substitution that increases the net charge at the neutral pH comprises a substitution to a lysine or an arginine. In some embodiments, amino acid substitution that increases the net charge at the neutral pH comprises a substitution of an aspartic acid or a glutamic acid to a neutral amino acid, a lysine or an arginine. In some embodiments, the mutant TcBuster transposase comprises one or more amino acid substitutions from Table 4.1. In some embodiments, the mutant TcBuster transposase further comprises one or more amino acid substitutions from Table 4. In some embodiments, the mutant TcBuster transposase comprises an amino acid substitution in a DNA Binding and Oligomerization domain; an insertion domain; a Zn-BED domain; or a combination thereof. In some embodiments, the mutant TcBuster transposase comprises an amino acid substitution that increases a net charge at a neutral pH within or in proximity to a catalytic domain in comparison to SEQ ID NO: 1. In some embodiments, the mutant TcBuster transposase comprises an amino acid substitution that increases a net charge at a neutral pH in comparison to SEQ ID NO: 1, wherein the one or more amino acids are located in proximity to D223, D289, or E589, when numbered in accordance to SEQ ID NO: 1. In some embodiments, the proximity is a distance of about 80, 75, 70, 60, 50, 40, 30, 20, 10, or 5 amino acids. In some embodiments, the proximity is a distance of about 70 to 80 amino acids. In some embodiments, the amino acid sequence of the mutant TcBuster transposase is at least 80%, at least 90%, at least 95%, at least 98%, or at least 99% identical to full-length SEQ ID NO: 1. In some embodiments, the mutant TcBuster transposase further comprises one or more amino acid substitutions from Table 2. In some embodiments, the mutant TcBuster transposase further comprises one or more amino acid substitutions from Table 3. In some embodiments, the mutant TcBuster transposase further comprises amino acid substitutions V377T, E469K, and D189A, when numbered in accordance with SEQ ID NO: 1. In some embodiments, the mutant TcBuster transposase further comprises amino acid substitutions K573E and E578L, when numbered in accordance with SEQ ID NO: 1. In some embodiments, the mutant TcBuster transposase further comprises amino acid substitution 1452K, when numbered in accordance with SEQ ID NO: 1. In some embodiments, the mutant TcBuster transposase further comprises amino acid substitution A358K, when numbered in accordance with SEQ ID NO: 1. In some embodiments, the mutant TcBuster transposase further comprises amino acid substitution V297K, when numbered in accordance with SEQ ID NO: 1. In some embodiments, the mutant TcBuster transposase further comprises amino acid substitution N85S, when numbered in accordance with SEQ ID NO: 1. In some embodiments, the mutant TcBuster transposase further comprises amino acid substitutions I452F, V377T, E469K, and D189A, when numbered in accordance with SEQ ID NO: 1. In some embodiments, the mutant TcBuster transposase further comprises amino acid substitutions A358K, V377T, E469K, and D189A, when numbered in accordance with SEQ ID NO: 1. In some embodiments, the mutant TcBuster transposase further comprises amino acid substitutions V377T, E469K, D189A, K573E and E578L, when numbered in accordance with SEQ ID NO: 1. In some embodiments, the mutant TcBuster transposase further comprises one or more amino acid substitutions from Table 1. In some embodiments, the mutant TcBuster transposase has increased transposition efficiency in comparison to a wild-type TcBuster transposase having amino acid sequence SEQ ID NO: 1. In some embodiments, the transposition efficiency is measured by an assay that comprises introducing the mutant TcBuster transposase or the wild-type TcBuster transposase and a TcBuster transposon containing a reporter cargo cassette into a population of cells, and detecting transposition of the reporter cargo cassette in genome of the population of cells.

Described herein, in one aspect, is a fusion transposase, comprising a TcBuster transposase sequence and one or more additional Nuclear Localization Signal sequences, wherein the TcBuster transposase sequence has at least 70% identity to full-length SEQ ID NO: 1. In some embodiments, the TcBuster transposase sequence has at least 80%, at least 90%, at least 95%, at least 98%, or at least 99% identity to full-length SEQ ID NO: 1. In some embodiments, the TcBuster transposase sequence comprises one or more amino acid substitutions that increase a net charge at a neutral pH in comparison to SEQ ID NO: 1. In some embodiments, the one or more amino acid substitutions comprise a substitution with a lysine or an arginine. In some embodiments, the one or more amino acid substitutions comprise a substitution of an aspartic acid or a glutamic acid with a neutral amino acid, a lysine or an arginine. In some embodiments, the TcBuster transposase sequence comprises one or more amino acid substitutions from Table 4, Table 4.1, or both. In some embodiments, the TcBuster transposase sequence comprises one or more amino acid substitutions in a DNA Binding and Oligomerization domain; an insertion domain; a Zn-BED domain; or a combination thereof. In some embodiments, the TcBuster transposase sequence comprises one or more amino acid substitutions from Table 1, Table 1.1, or both. In some embodiments, the TcBuster transposase sequence has increased transposition efficiency in comparison to a wild-type TcBuster transposase having amino acid sequence SEQ ID NO: 1. In some embodiments, the transposition efficiency of the TcBuster transposase sequence is measured by an assay that comprises introducing the fusion transposase or the wild-type TcBuster transposase and a TcBuster transposon containing a reporter cargo cassette into a population of cells, and detecting transposition of the reporter cargo cassette in genome of the population of cells. In some embodiments, the TcBuster transposase sequence comprises one or more amino acid substitutions that increase a net charge at a neutral pH within or in proximity to a catalytic domain in comparison to SEQ ID NO: 1. In some embodiments, the TcBuster transposase sequence comprises one or more amino acid substitutions that increase a net charge at a neutral pH in comparison to SEQ ID NO: 1, wherein the one or more amino acid substitutions are located in proximity to D223, D289, or E589, when numbered in accordance to SEQ ID NO: 1. In some embodiments, the proximity is a distance of about 80, 75, 70, 60, 50, 40, 30, 20, 10, or 5 amino acids. In some embodiments, the proximity is a distance of about 70 to 80 amino acids. In some embodiments, the TcBuster transposase sequence comprises one or more amino acid substitutions from Table 2. In some embodiments, the TcBuster transposase sequence comprises one or more amino acid substitutions from Table 3. In some embodiments, the TcBuster transposase sequence comprises amino acid substitutions V377T, E469K, and D189A, when numbered in accordance with SEQ ID NO: 1. In some embodiments, the TcBuster transposase sequence comprises amino acid substitutions K573E and E578L, when numbered in accordance with SEQ ID NO: 1. In some embodiments, the TcBuster transposase sequence comprises amino acid substitution I452K, when numbered in accordance with SEQ ID NO: 1. In some embodiments, the TcBuster transposase sequence comprises amino acid substitution A358K, when numbered in accordance with SEQ ID NO: 1. In some embodiments, the TcBuster transposase sequence comprises amino acid substitution V297K, when numbered in accordance with SEQ ID NO: 1. In some embodiments, the TcBuster transposase sequence comprises amino acid substitution N85S, when numbered in accordance with SEQ ID NO: 1. In some embodiments, the TcBuster transposase sequence comprises amino acid substitutions I452F, V377T, E469K, and D189A, when numbered in accordance with SEQ ID NO: 1. In some embodiments, the TcBuster transposase sequence comprises amino acid substitutions A358K, V377T, E469K, and D189A, when numbered in accordance with SEQ ID NO: 1. In some embodiments, the TcBuster transposase sequence comprises amino acid substitutions V377T, E469K, D189A, K573E and E578L, when numbered in accordance with SEQ ID NO: 1. In some embodiments, the TcBuster transposase sequence has 100% identity to full-length SEQ ID NO: 1.

Described herein, in one aspect, is a fusion transposase comprising a TcBuster transposase sequence and a DNA sequence specific binding domain, wherein the TcBuster transposase sequence has an amino acid sequence any of the mutant TcBuster transposes described herein. In some embodiments, the DNA sequence specific binding domain comprises a TALE domain, zinc finger domain, AAV Rep DNA-binding domain, or any combination thereof. In some embodiments, the DNA sequence specific binding domain comprises a TALE domain. In some embodiments, the TcBuster transposase sequence and the DNA sequence specific binding domain are separated by a linker. In some embodiments, the linker comprises at least 3, at least 4, at least 5, at least 6, at least 7, at least 8, at least 9, at least 10, at least 15, at least 20, or at least 50 amino acids. In some embodiments, the linker comprises SEQ ID NO: 9.

Described herein, in one aspect, is a polynucleotide comprising a nucleic acid sequence at least about 80%, 85%, 90%, 95%, or 98% identical to or complementary with full length SEQ ID NO: 204 or 207. Described herein, in one aspect, is a polynucleotide that codes for the mutant TcBuster transposase described herein. Described herein, in one aspect, is a polynucleotide that codes for the fusion transposase described herein. In some embodiments, the polynucleotide comprises DNA that encodes the mutant TcBuster transposase or the fusion transposase. In some embodiments, the polynucleotide comprises messenger RNA (mRNA) that encodes the mutant TcBuster transposase or the fusion transposase. In some embodiments, the mRNA is chemically modified. In some embodiments, the polynucleotide comprises nucleic acid sequence encoding for a transposon recognizable by the mutant TcBuster transposase or the fusion transposase. In some embodiments, the polynucleotide is present in a DNA vector. In some embodiments, the DNA vector comprises a mini-circle plasmid. In some embodiments, the polynucleotide is codon optimized for expression in human cells. In some embodiments, the polynucleotide comprises a nucleic acid sequence at least about 70%, 75%, 80%, 85%, 90%, 95%, or 98% identical to or complementary with full length SEQ ID NO: 204 or 207. In some embodiments, the polynucleotide comprises a nucleic acid sequence at least about 80%, 85%, 90%, 95%, or 98% identical to or complementary with full length SEQ ID NO: 204 or 207. In some embodiments, the polynucleotide comprises a nucleic acid sequence at least about 95% identical to or complementary with full length SEQ ID NO: 204 or 207. In some embodiments, the polynucleotide comprises a nucleic acid sequence 100% identical to or complementary with full length SEQ ID NO: 204 or 207.

One aspect of the present disclosure provides a mutant TcBuster transposase, comprising an amino acid sequence at least 70% identical to full-length SEQ ID NO: 1 and having one or more amino acid substitutions that increase a net charge at a neutral pH in comparison to SEQ ID NO: 1. In some embodiments, the mutant TcBuster transposase has increased transposition efficiency in comparison to a wild-type TcBuster transposase having amino acid sequence SEQ ID NO: 1. Another aspect of the present disclosure provides a mutant TcBuster transposase, comprising an amino acid sequence at least 70% identical to full-length SEQ ID NO: 1 and having one more amino acid substitutions in a DNA Binding and Oligomerization domain; an insertion domain; a Zn-BED domain; or a combination thereof. In some embodiments, the mutant TcBuster transposase has increased transposition efficiency in comparison to a wild-type TcBuster transposase having amino acid sequence SEQ ID NO: 1. Yet another aspect of the present disclosure provides a mutant TcBuster transposase comprising an amino acid sequence at least 70% identical to full-length SEQ ID NO: 1 and having one or more amino acid substitutions from Table 1. In some embodiments, a mutant TcBuster transposase comprises one or more amino acid substitutions that increase a net charge at a neutral pH within or in proximity to a catalytic domain in comparison to SEQ ID NO: 1. In some embodiments, the mutant TcBuster transposase comprises one or more amino acid substitutions that increase a net charge at a neutral pH in comparison to SEQ ID NO: 1, and the one or more amino acids are located in proximity to D223, D289, or E589, when numbered in accordance to SEQ ID NO: 1. In some embodiments, the proximity is a distance of about 80, 75, 70, 60, 50, 40, 30, 20, 10, or 5 amino acids. In some embodiments, the proximity is a distance of about 70 to 80 amino acids. In some embodiments, the amino acid sequence of the mutant TcBuster transposase is at least 80%, at least 90%, at least 95%, at least 98%, or at least 99% identical to full-length SEQ ID NO: 1. In some embodiments, the one or more amino acid substitutions comprise a substitution to a lysine or an arginine. In some embodiments, the one or more amino acid substitutions comprise a substitution of an aspartic acid or a glutamic acid to a neutral amino acid, a lysine or an arginine. In some embodiments, the mutant TcBuster transposase comprises one or more amino acid substitutions from Table 4. In some embodiments, the mutant TcBuster transposase comprises one or more amino acid substitutions from Table 2. In some embodiments, the mutant TcBuster transposase comprises one or more amino acid substitutions from Table 3. In some embodiments, the mutant TcBuster transposase comprises amino acid substitutions V377T, E469K, and D189A, when numbered in accordance with SEQ ID NO: 1. In some embodiments, the mutant TcBuster transposase comprises amino acid substitutions K573E and E578L, when numbered in accordance with SEQ ID NO: 1. In some embodiments, the mutant TcBuster transposase comprises amino acid substitution 1452K, when numbered in accordance with SEQ ID NO: 1. In some embodiments, the mutant TcBuster transposase comprises amino acid substitution A358K, when numbered in accordance with SEQ ID NO: 1. In some embodiments, the mutant TcBuster transposase comprises amino acid substitution V297K, when numbered in accordance with SEQ ID NO: 1. In some embodiments, the mutant TcBuster transposase comprises amino acid substitution N85S, when numbered in accordance with SEQ ID NO: 1. In some embodiments, the mutant TcBuster transposase comprises amino acid substitutions I452F, V377T, E469K, and D189A, when numbered in accordance with SEQ ID NO: 1. In some embodiments, the mutant TcBuster transposase comprises amino acid substitutions A358K, V377T, E469K, and D189A, when numbered in accordance with SEQ ID NO: 1. In some embodiments, the mutant TcBuster transposase comprises amino acid substitutions V377T, E469K, D189A, K573E and E578L, when numbered in accordance with SEQ ID NO: 1. In some embodiments, the transposition efficiency is measured by an assay that comprises introducing the mutant TcBuster transposase and a TcBuster transposon containing a reporter cargo cassette into a population of cells, and detecting transposition of the reporter cargo cassette in genome of the population of cells.

Yet another aspect of the present disclosure provides a fusion transposase comprising a TcBuster transposase sequence and a DNA sequence specific binding domain. In some embodiments, the TcBuster transposase sequence has at least 70% identity to full-length SEQ ID NO: 1. In some embodiments, the DNA sequence specific binding domain comprises a TALE domain, zinc finger domain, AAV Rep DNA-binding domain, or any combination thereof. In some embodiments, the DNA sequence specific binding domain comprises a TALE domain. In some embodiments, the TcBuster transposase sequence has at least 80%, at least 90%, at least 95%, at least 98%, or at least 99% identity to full-length SEQ ID NO: 1. In some embodiments, the TcBuster transposase sequence comprises one or more amino acid substitutions that increase a net charge at a neutral pH in comparison to SEQ ID NO: 1. In some embodiments, the TcBuster transposase sequence comprises one or more amino acid substitutions in a DNA Binding and Oligomerization domain; an insertion domain; a Zn-BED domain; or a combination thereof. In some embodiments, the TcBuster transposase sequence comprises one or more amino acid substitutions from Table 1. In some embodiments, the TcBuster transposase sequence has increased transposition efficiency in comparison to a wild-type TcBuster transposase having amino acid sequence SEQ ID NO: 1. In some embodiments, the TcBuster transposase sequence comprises one or more amino acid substitutions that increase a net charge at a neutral pH within or in proximity to a catalytic domain in comparison to SEQ ID NO: 1. In some embodiments, the TcBuster transposase sequence comprises one or more amino acid substitutions that increase a net charge at a neutral pH in comparison to SEQ ID NO: 1, and the one or more amino acid substitutions are located in proximity to D223, D289, or E589, when numbered in accordance to SEQ ID NO: 1. In some embodiments, the proximity is a distance of about 80, 75, 70, 60, 50, 40, 30, 20, 10, or 5 amino acids. In some embodiments, the proximity is a distance of about 70 to 80 amino acids. In some embodiments, the TcBuster transposase sequence comprises one or more amino acid substitutions from Table 2. In some embodiments, the TcBuster transposase sequence comprises one or more amino acid substitutions from Table 3. In some embodiments, the TcBuster transposase sequence comprises amino acid substitutions V377T, E469K, and D189A, when numbered in accordance with SEQ ID NO: 1. In some embodiments, the TcBuster transposase sequence comprises amino acid substitutions K573E and E578L, when numbered in accordance with SEQ ID NO: 1. In some embodiments, the TcBuster transposase sequence comprises amino acid substitution 1452K, when numbered in accordance with SEQ ID NO: 1. In some embodiments, the TcBuster transposase sequence comprises amino acid substitution A358K, when numbered in accordance with SEQ ID NO: 1. In some embodiments, the TcBuster transposase sequence comprises amino acid substitution V297K, when numbered in accordance with SEQ ID NO: 1. In some embodiments, the TcBuster transposase sequence comprises amino acid substitution N85S, when numbered in accordance with SEQ ID NO: 1. In some embodiments, the TcBuster transposase sequence comprises amino acid substitutions I452F, V377T, E469K, and D189A, when numbered in accordance with SEQ ID NO: 1. In some embodiments, the TcBuster transposase sequence comprises amino acid substitutions A358K, V377T, E469K, and D189A, when numbered in accordance with SEQ ID NO: 1. In some embodiments, the TcBuster transposase sequence comprises amino acid substitutions V377T, E469K, D189A, K573E and E578L, when numbered in accordance with SEQ ID NO: 1. In some embodiments, the TcBuster transposase sequence has 100% identity to full-length SEQ ID NO: 1. In some embodiments of a fusion transposase, the TcBuster transposase sequence and the DNA sequence specific binding domain are separated by a linker. In some embodiments, the linker comprises at least 3, at least 4, at least 5, at least 6, at least 7, at least 8, at least 9, at least 10, at least 15, at least 20, or at least 50 amino acids. In some embodiments, the linker comprises SEQ ID NO: 9.

Yet another aspect of the present disclosure provides a polynucleotide that codes for the mutant TcBuster transposase as described herein. Yet another aspect of the present disclosure provides a polynucleotide that codes for the fusion transposase as described herein. In some embodiments, the polynucleotide comprises DNA that encodes the mutant TcBuster transposase or the fusion transposase. In some embodiments, the polynucleotide comprises messenger RNA (mRNA) that encodes the mutant TcBuster transposase or the fusion transposase. In some embodiments, the mRNA is chemically modified. In some embodiments, the polynucleotide comprises nucleic acid sequence encoding for a transposon recognizable by the mutant TcBuster transposase or the fusion transposase. In some embodiments, the polynucleotide is present in a DNA vector. In some embodiments, the DNA vector comprises a mini-circle plasmid.

Yet another aspect of the present disclosure provides a cell producing the mutant TcBuster transposase or fusion transposase as described herein. Yet another aspect of the present disclosure provides a cell containing the polynucleotide as described herein. Yet another aspect of the present disclosure provides a method comprising: introducing into a cell the mutant TcBuster transposase as described herein and a transposon recognizable by the mutant TcBuster transposase. Yet another aspect of the present disclosure provides a method comprising: introducing into a cell the fusion transposase as described herein and a transposon recognizable by the fusion transposase. In some embodiments of a method, the introducing comprises contacting the cell with a polynucleotide encoding the mutant TcBuster transposase or the fusion transposase. In some embodiments, the polynucleotide comprises DNA that encodes the mutant TcBuster transposase or the fusion transposase. In some embodiments, the polynucleotide comprises messenger RNA (mRNA) that encodes the mutant TcBuster transposase or the fusion transposase. In some embodiments, the mRNA is chemically modified. In some embodiments of a method, the introducing comprises contacting the cell with a DNA vector that contains the transposon. In some embodiments, the DNA vector comprises a mini-circle plasmid. In some embodiments, the introducing comprises contacting the cell with a plasmid vector that contains both the transposon and the polynucleotide encoding the mutant TcBuster transposase or the fusion transposase. In some embodiments, the introducing comprises contacting the cell with the mutant TcBuster transposase or the fusion transposase as a purified protein. In some embodiments of a method, the transposon comprises a cargo cassette positioned between two inverted repeats. In some embodiments, a left inverted repeat of the two inverted repeats comprises a sequence having at least 50%, at least 60%, at least 80%, at least 90%, at least 95%, at least 98%, or at least 99% identity to SEQ ID NO: 3. In some embodiments, a left inverted repeat of the two inverted repeats comprises SEQ ID NO: 3. In some embodiments, a right inverted repeat of the two inverted repeats comprises a sequence having at least 50%, at least 60%, at least 80%, at least 90%, at least 95%, at least 98%, or at least 99% identity to SEQ ID NO: 4. In some embodiments, a right inverted repeat of the two inverted repeats comprises SEQ ID NO: 4. In some embodiments, a left inverted repeat of the two inverted repeats comprises a sequence having at least 50%, at least 60%, at least 80%, at least 90%, at least 95%, at least 98%, or at least 99% identity to SEQ ID NO: 5. In some embodiments, a left inverted repeat of the two inverted repeats comprises SEQ ID NO: 5. In some embodiments, a right inverted repeat of the two inverted repeats comprises a sequence having at least 50%, at least 60%, at least 80%, at least 90%, at least 95%, at least 98%, or at least 99% identity to SEQ ID NO: 6. In some embodiments, a right inverted repeat of the two inverted repeats comprises SEQ ID NO: 6. In some embodiments, a left inverted repeat of the two inverted repeats comprises a sequence having at least 50%, at least 60%, at least 80%, at least 90%, at least 95%, at least 98%, or at least 99% identity to SEQ ID NO: 205. In some embodiments, a left inverted repeat of the two inverted repeats comprises SEQ ID NO: 205. In some embodiments, a right inverted repeat of the two inverted repeats comprises a sequence having at least 50%, at least 60%, at least 80%, at least 90%, at least 95%, at least 98%, or at least 99% identity to SEQ ID NO: 206. In some embodiments, a right inverted repeat of the two inverted repeats comprises SEQ ID NO: 206. In some embodiments, the cargo cassette comprises a promoter selected from the group consisting of: CMV, EFS, MND, EF1α, CAGCs, PGK, UBC, U6, H1, and Cumate. In some embodiments, the cargo cassette comprises a CMV promoter. In some embodiments, the cargo cassette is present in a forward direction. In some embodiments, the cargo cassette is present in a reverse direction. In some embodiments, the cargo cassette comprises a transgene. In some embodiments, the transgene codes for a protein selected from the group consisting of: a cellular receptor, an immunological checkpoint protein, a cytokine, and any combination thereof. In some embodiments, the transgene codes for a cellular receptor selected from the group consisting of: a T cell receptor (TCR), a B cell receptor (BCR), a chimeric antigen receptor (CAR), or any combination thereof. In some embodiments, the introducing comprises transfecting the cell with the aid of electroporation, microinjection, calcium phosphate precipitation, cationic polymers, dendrimers, liposome, microprojectile bombardment, fugene, direct sonic loading, cell squeezing, optical transfection, protoplast fusion, impalefection, magnetofection, nucleofection, or any combination thereof. In some embodiments, the introducing comprises electroporating the cell. In some embodiments of a method, the cell is a primary cell isolated from a subject. In some embodiments, the subject is a human. In some embodiments, the subject is a patient with a disease. In some embodiments, the subject has been diagnosed with cancer or tumor. In some embodiments, the cell is isolated from blood of the subject. In some embodiments, the cell comprises a primary immune cell. In some embodiments, the cell comprises a primary leukocyte. In some embodiments, the cell comprises a primary T cell. In some embodiments, the primary T cell comprises a gamma delta T cell, a helper T cell, a memory T cell, a natural killer T cell, an effector T cell, or any combination thereof. In some embodiments, the primary immune cell comprises a CD3+ cell. In some embodiments, the cell comprises a stem cell. In some embodiments, the stem cell is selected from the group consisting of: embryonic stem cell, hematopoietic stem cell, epidermal stem cell, epithelial stem cell, bronchoalveolar stem cell, mammary stem cell, mesenchymal stem cell, intestine stem cell, endothelial stem cell, neural stem cell, olfactory adult stem cell, neural crest stem cell, testicular cell, and any combination thereof. In some embodiments, the stem cell comprises induced pluripotent stem cell.

Yet another aspect of the present disclosure provides a method of treatment, comprising: (a) introducing into a cell a transposon and the mutant TcBuster transposase or the fusion transposase as described herein, which recognize the transposon, thereby generating a genetically modified cell; (b) administering the genetically modified cell to a patient in need of the treatment. In some embodiments, the genetically modified cell comprises a transgene introduced by the transposon. In some embodiments, the patient has been diagnosed with cancer or tumor. In some embodiments, the administering comprises transfusing the genetically modified cell into blood vessels of the patient.

Yet another aspect of the present disclosure provides a system for genome editing, comprising: the mutant TcBuster transposase or fusion transposase as described herein, and a transposon recognizable by the mutant TcBuster transposase or the fusion transposase. Yet another aspect of the present disclosure provides a system for genome editing, comprising: the polynucleotide encoding a mutant TcBuster transposase or fusion transposase as described herein, and a transposon recognizable by the mutant TcBuster transposase or the fusion transposase. In some embodiments of a system, the polynucleotide comprises DNA that encodes the mutant TcBuster transposase or the fusion transposase. In some embodiments, the polynucleotide comprises messenger RNA (mRNA) that encodes the mutant TcBuster transposase or the fusion transposase. In some embodiments, the mRNA is chemically modified. In some embodiments, the transposon is present in a DNA vector. In some embodiments, the DNA vector comprises a mini-circle plasmid. In some embodiments, the polynucleotide and the transposon are present in a same plasmid. In some embodiments, the transposon comprises a cargo cassette positioned between two inverted repeats. In some embodiments, a left inverted repeat of the two inverted repeats comprises a sequence having at least 50%, at least 60%, at least 80%, at least 90%, at least 95%, at least 98%, or at least 99% identity to SEQ ID NO: 3. In some embodiments, a left inverted repeat of the two inverted repeats comprises SEQ ID NO: 3. In some embodiments, a right inverted repeat of the two inverted repeats comprises a sequence having at least 50%, at least 60%, at least 80%, at least 90%, at least 95%, at least 98%, or at least 99% identity to SEQ ID NO: 4. In some embodiments, a right inverted repeat of the two inverted repeats comprises SEQ ID NO: 4. In some embodiments, a left inverted repeat of the two inverted repeats comprises a sequence having at least 50%, at least 60%, at least 80%, at least 90%, at least 95%, at least 98%, or at least 99% identity to SEQ ID NO: 5. In some embodiments, a left inverted repeat of the two inverted repeats comprises SEQ ID NO: 5. In some embodiments, a right inverted repeat of the two inverted repeats comprises a sequence having at least 50%, at least 60%, at least 80%, at least 90%, at least 95%, at least 98%, or at least 99% identity to SEQ ID NO: 6. In some embodiments, a right inverted repeat of the two inverted repeats comprises SEQ ID NO: 6. In some embodiments, a left inverted repeat of the two inverted repeats comprises a sequence having at least 50%, at least 60%, at least 80%, at least 90%, at least 95%, at least 98%, or at least 99% identity to SEQ ID NO: 205. In some embodiments, a left inverted repeat of the two inverted repeats comprises SEQ ID NO: 205. In some embodiments, a right inverted repeat of the two inverted repeats comprises a sequence having at least 50%, at least 60%, at least 80%, at least 90%, at least 95%, at least 98%, or at least 99% identity to SEQ ID NO: 206. In some embodiments, a right inverted repeat of the two inverted repeats comprises SEQ ID NO: 206. In some embodiments, the cargo cassette comprises a promoter selected from the group consisting of: CMV, EFS, MND, EF1α, CAGCs, PGK, UBC, U6, H1, and Cumate. In some embodiments, the cargo cassette comprises a CMV promoter. In some embodiments, the cargo cassette comprises a transgene. In some embodiments, the transgene codes for a protein selected from the group consisting of: a cellular receptor, an immunological checkpoint protein, a cytokine, and any combination thereof. In some embodiments, the transgene codes for a cellular receptor selected from the group consisting of: a T cell receptor (TCR), a B cell receptor (BCR), a chimeric antigen receptor (CAR), or any combination thereof. In some embodiments, the cargo cassette is present in a forward direction. In some embodiments, the cargo cassette is present in a reverse direction.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent that a term incorporated by reference conflicts with a term defined herein, this specification controls.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 11 shows amino acid sequence of wild-type TcBuster transposase with certain amino acids annotated (SEQ ID NO: 1).

FIG. 12 shows amino acid sequence of mutant TcBuster transposase containing amino acid substitutions D189A/V377T/E469K (SEQ ID NO: 78).

FIG. 13 shows amino acid sequence of mutant TcBuster transposase containing amino acid substitutions D189A/V377T/E469K/I452K (SEQ ID NO: 79).

FIG. 14 shows amino acid sequence of mutant TcBuster transposase containing amino acid substitutions D189A/V377T/E469K/N85S (SEQ ID NO: 80).

FIG. 15 shows amino acid sequence of mutant TcBuster transposase containing amino acid substitutions D189A/V377T/E469K/A358K (SEQ ID NO: 81).

FIG. 16 shows amino acid sequence of mutant TcBuster transposase containing amino acid substitutions D189A/V377T/E469K/K573E/E578L (SEQ ID NO: 13).

DETAILED DESCRIPTION

Overview

Figure 1:
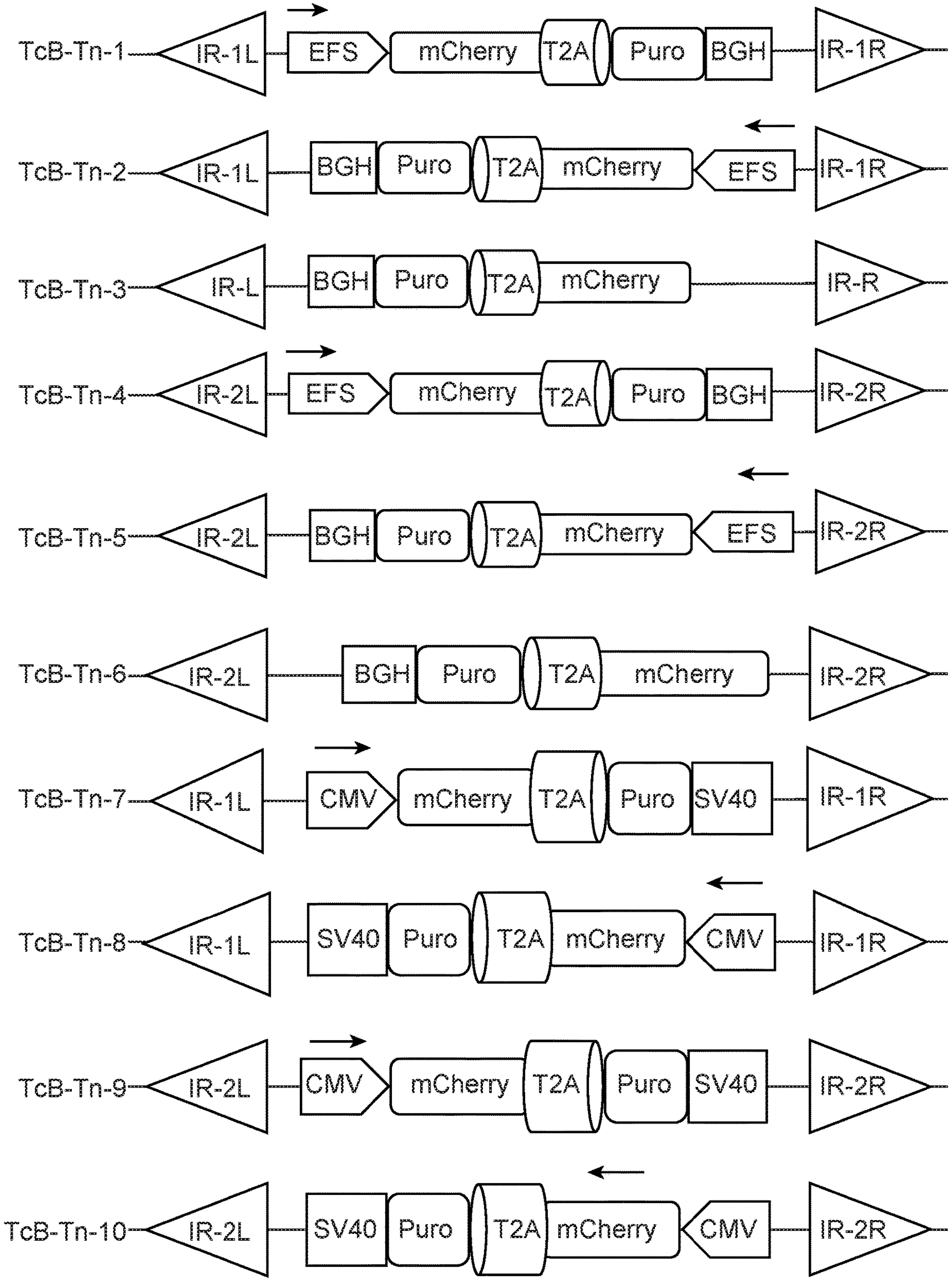
FIG. 1 shows the transposition efficiency of several exemplary TcBuster transposon vector constructs, as measured by percent of mCherry positive cells in cells that were transfected with wild-type (WT) TcBuster transposase and the exemplary TcBuster transposons.
Figure 1:
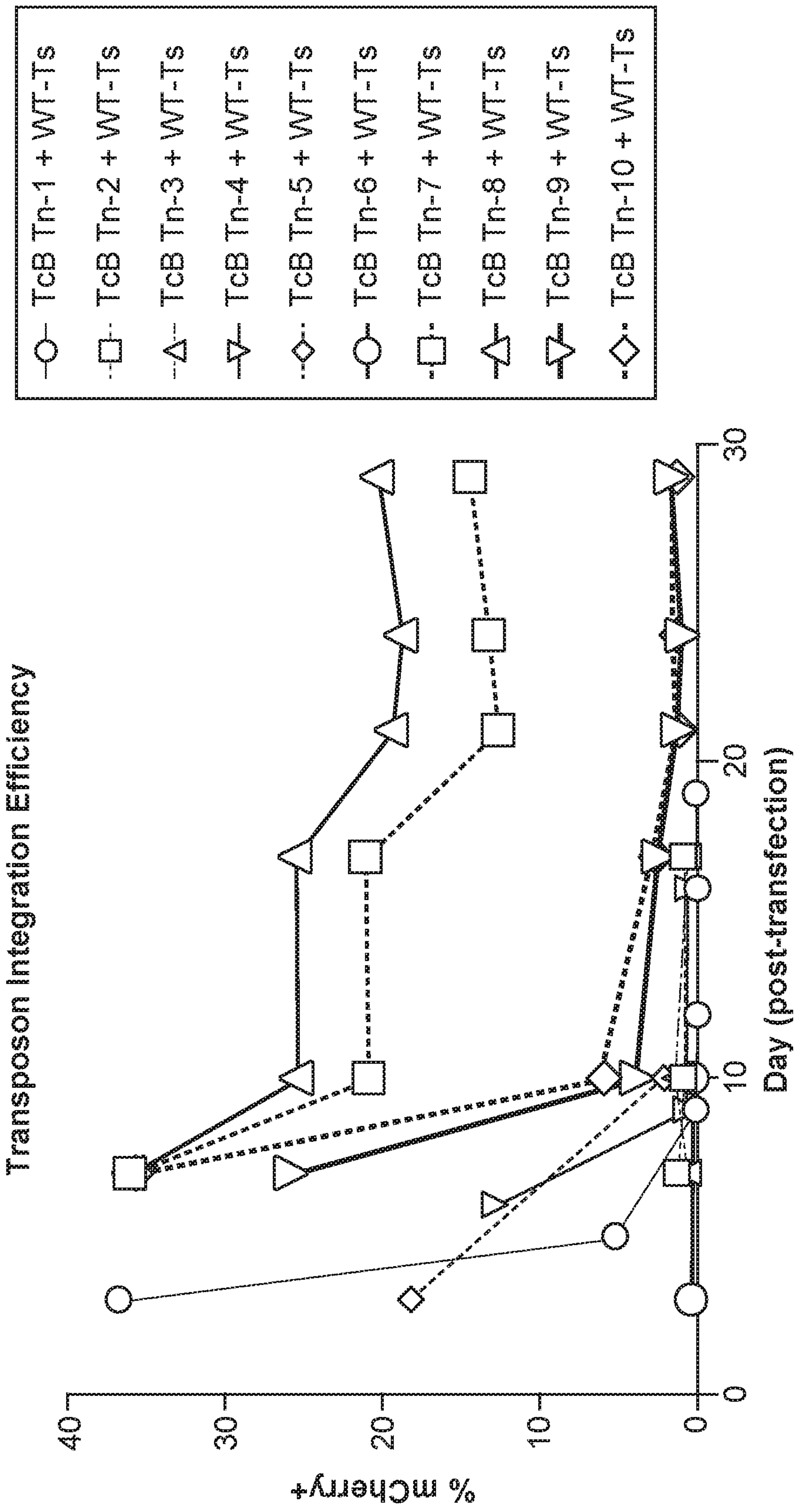

DNA transposons can translocate via a non-replicative, 'cut-and-paste' mechanism. This requires recognition of the two terminal inverted repeats by a catalytic enzyme, i.e. transposase, which can cleave its target and consequently release the DNA transposon from its donor template. Upon excision, the DNA transposons may subsequently integrate into the acceptor DNA that is cleaved by the same transposase. In some of their natural configurations, DNA transposons are flanked by two inverted repeats and may contain a gene encoding a transposase that catalyzes transposition.

For genome editing applications with DNA transposons, it is desirable to design a transposon to develop a binary system based on two distinct plasmids whereby the transposase is physically separated from the transposon DNA containing the gene of interest flanked by the inverted repeats. Co-delivery of the transposon and transposase plasmids into the target cells enables transposition via a conventional cut-and-paste mechanism.

TcBuster is a member of the hAT family of DNA transposons. Other members of the family include Sleeping Beauty and PiggBac. Discussed herein are various devices, systems and methods relating to synergistic approaches to enhance gene transfer into human hematopoietic and immune system cells using hAT family transposon components. The present disclosure relates to improved hAT transposases, transposon vector sequences, transposase delivery methods, and transposon delivery methods. In one implementation, the present study identified specific, universal sites for making hyperactive hAT transposases. In another implementation, methods for making minimally sized hAT transposon vector inverted terminal repeats (ITRs) that conserve genomic space are described. In another implementation, improved methods to deliver hAT family transposases as chemically modified in vitro transcribed mRNAs are described. In another implementation, methods to deliver hAT family transposon vectors as "miniature" circles of DNA are described, in which virtually all prokaryotic sequences have been removed by a recombination method. In another implementation, methods to fuse DNA sequence specific binding domains using transcription activator-like (TAL) domains fused to the hAT transposases are described. These improvements, individually or in combination, can yield unexpectedly high levels of gene transfer to the cell types in question and improvements in the delivery of transposon vectors to sequences of interest.

Mutant TcBuster Transposase

One aspect of the present disclosure provides a mutant TcBuster transposase. A mutant TcBuster transposase may comprise one or more amino acid substitutions in comparison to a wild-type TcBuster transposase (SEQ ID NO: 1).

A mutant TcBuster transposase can comprise an amino acid sequence having at least 70% sequence identity to full length sequence of a wild-type TcBuster transposase (SEQ ID NO: 1). In some embodiments, a mutant TcBuster transposase can comprise an amino acid sequence having at least 40%, at least 50%, at least 60%, at least 70%, at least 80%, at least 90%, at least 95%, at least 96%, at least 97%, at least 98%, or at least 99% sequence identity to full length sequence of a wild-type TcBuster transposase (SEQ ID NO: 1). In some cases, a mutant TcBuster transposase can comprise an amino acid sequence having at least 98%, at least 98.5%, at least 99%, at least 99.1%, at least 99.2%, at least 99.3%, at least 99.4%, at least 99.5%, at least 99.6%, at least 99.7%, at least 99.8%, at least 99.9%, or at least 99.95% sequence identity to full length sequence of a wild-type TcBuster transposase (SEQ ID NO: 1).

The term "percent (%) identity," as used herein, can refer to the percentage of amino acid (or nucleic acid) residues of a candidate sequence that are identical to the amino acid (or nucleic acid) residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment, for purposes of determining percent identity, can be achieved in various ways that are within the skill in the art, for instance, using publicly available computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence.

The terms "complement," "complements," "complementary," and "complementarity," as used herein, can refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, can be measured by any suitable alignment algorithm, including but not limited to the Needleman-Wunsch algorithm (see e.g. the EMBOSS Needle aligner available at ebi.ac.uk/Tools/psa/emboss needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at ebi.ac.uk/Tools/psa/emboss_water/nucleotide.html, optionally with default settings). Optimal alignment can be assessed using any suitable parameters of a chosen algorithm, including default parameters.

Complementarity can be perfect or substantial/sufficient. Perfect complementarity between two nucleic acids can mean that the two nucleic acids can form a duplex in which every base in the duplex is bonded to a complementary base by Watson-Crick pairing. Substantial or sufficient complementary can mean that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods.

A mutant TcBuster transposase can comprise an amino acid sequence having at least one amino acid different from full length sequence of a wild-type TcBuster transposase (SEQ ID NO: 1). In some embodiments, a mutant TcBuster transposase can comprise an amino acid sequence having at least 2, at least 3, at least 4, at least 5, at least 6, at least 7, at least 8, at least 9, at least 10, or more amino acids different from full length sequence of a wild-type TcBuster transposase (SEQ ID NO: 1). In some cases, a mutant TcBuster transposase can comprise an amino acid sequence having at least 5, at least 10, at least 20, at least 30, at least 40, at least 50, at least 60, at least 70, at least 80, at least 90, at least 100, at least 200, or at least 300 amino acid different from full length sequence of a wild-type TcBuster transposase (SEQ ID NO: 1). In some cases, a mutant TcBuster transposase can comprise an amino acid sequence having at most 3, at most 6, at most 12, at most 25, at most 35, at most 45, at most 55, at most 65, at most 75, at most 85, at most 95, at most 150, at most 250, or at most 350 amino acid different from full length sequence of a wild-type TcBuster transposase (SEQ ID NO: 1).

Figure 4:
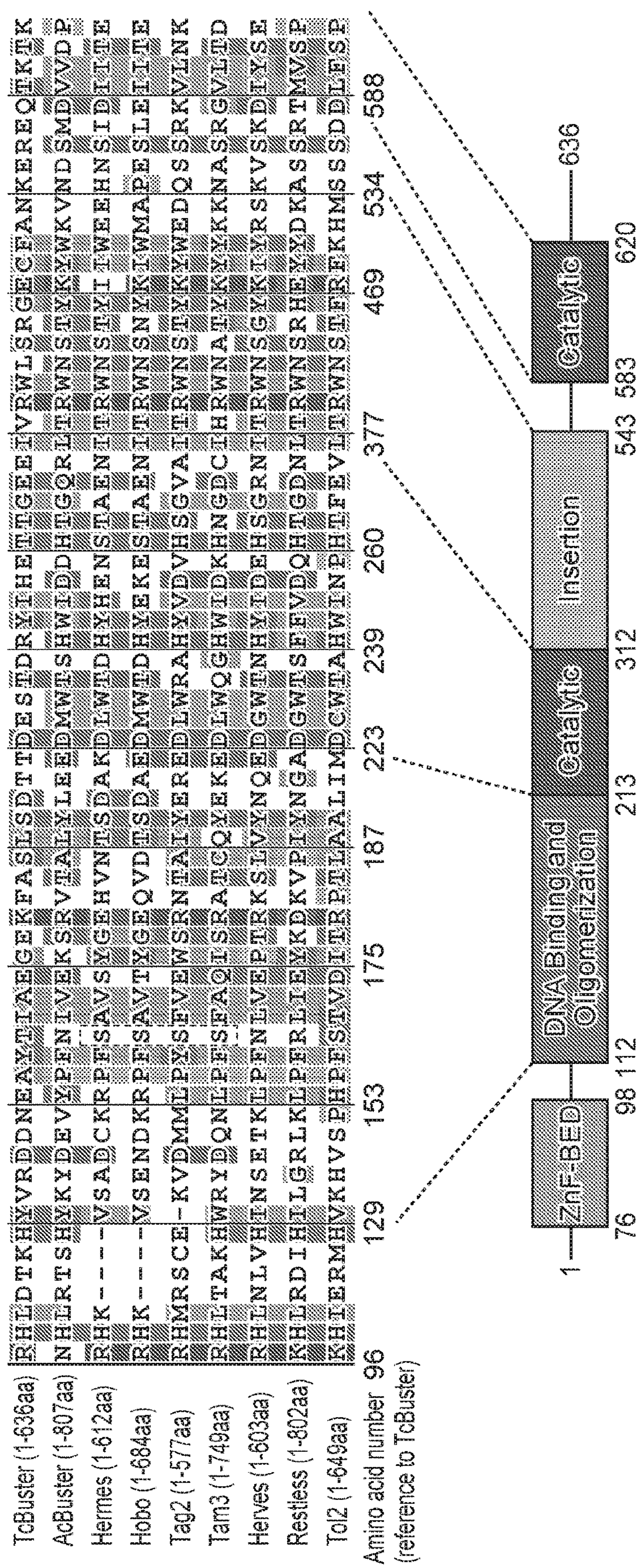
FIG. 4 depicts the amino acid sequence alignment of TcBuster transposase versus a number of transposases in AC subfamily, with only regions of amino acid conservation being shown (SEQ ID NOS 89-194, respectively in order of appearance).

As shown in FIG. 4, typically, a wild-type TcBuster transposase can be regarded as comprising, from N terminus to C terminus, a ZnF-BED domain (amino acids 76-98), a DNA Binding and Oligomerization domain (amino acids 112-213), a first Catalytic domain (amino acids 213-312), an Insertion domain (amino acids 312-543), and a second Catalytic domain (amino acids 583-620), as well as at least four inter-domain regions in between these annotated domains. Unless indicated otherwise, numerical references to amino acids, as used herein, are all in accordance to SEQ ID NO: 1. A mutant TcBuster transposase can comprise one or more amino acid substitutions in any one of these domains, or any combination thereof. In some cases, a mutant TcBuster transposase can comprise one or more amino acid substitutions in ZnF-BED domain, a DNA Binding and Oligomerization domain, a first Catalytic domain, an Insertion domain, or a combination thereof. A mutant TcBuster transposase can comprise one or more amino acid substitutions in at least one of the two catalytic domains.

An exemplary mutant TcBuster transposase can comprise one or more amino acid substitutions from Table 1 or Table 1.1. Sometimes, a mutant TcBuster transposase can comprise at least one of the amino acid substitutions from Table 1 or Table 1.1. A mutant TcBuster transposase can comprise at least 2, at least 3, at least 4, at least 5, at least 6, at least 7, at least 8, at least 9, at least 10, at least 20, at least 30, or more of the amino acid substitutions from Table 1 or Table 1.1.

TABLE 1

| Amino Acid of Wild-type TcBuster Transposase (SEQ ID NO: 1) | Amino Acid Substitution |
|---|---|
| Q82 | Q82E |
| N85 | N85S |
| D99 | D99A |
| D132 | D132A |
| Q151 | Q151S |
| Q151 | Q151A |
| E153 | E153K |
| E153 | E153R |
| A154 | A154P |
| Y155 | Y155H |
| E159 | E159A |
| T171 | T171K |
| T171 | T171R |
| K177 | K177E |
| D183 | D183K |
| D183 | D183R |
| D189 | D189A |

TABLE 1-continued

| Amino Acid of Wild-type TcBuster Transposase (SEQ ID NO: 1) | Amino Acid Substitution |
|---|---|
| T191 | T191E |
| S193 | S193K |
| S193 | S193R |
| Y201 | Y201A |
| F202 | F202D |
| F202 | F202K |
| C203 | C203I |
| C203 | C203V |
| Q221 | Q221T |
| M222 | M222L |
| I233 | I233Q |
| E224 | E224G |
| S225 | S225W |
| D227 | D227A |
| R239 | R239H |
| E243 | E243A |
| E247 | E247K |
| P257 | P257K |
| P257 | P257R |
| Q258 | Q258T |
| E263 | E263A |
| E263 | E263K |
| E263 | E263R |
| E274 | E274K |
| E274 | E274R |
| S277 | S277K |
| N281 | N281E |
| L282 | L282K |
| L282 | L282R |
| K292 | K292P |
| V297 | V297K |
| K299 | K299S |
| A303 | A303T |
| H322 | H322E |
| A332 | A332S |
| A358 | A358E |
| A358 | A358K |
| A358 | A358S |
| D376 | D376A |
| V377 | V377T |
| L380 | L380N |
| I398 | I398D |
| I398 | I398S |
| I398 | I398K |
| F400 | F400L |
| V431 | V431L |
| S447 | S447E |
| N450 | N450K |
| N450 | N450R |
| I452 | I452F |
| E469 | E469K |
| P510 | P510D |
| P510 | P510N |
| E519 | E519R |
| R536 | R536S |
| V553 | V553S |
| P554 | P554T |
| P559 | P559D |
| P559 | P559S |
| P559 | P559K |
| K573 | K573E |
| E578 | E578L |
| K590 | K590T |
| Y595 | Y595L |
| V596 | V596A |
| T598 | T598I |
| K599 | K599A |
| Q615 | Q615A |
| T618 | T618K |
| T618 | T618R |
| D622 | D622K |
| D622 | D622R |
| E274 | E274K |

TABLE 1.1

| Amino Acid of Wild-type TcBuster Transposase (SEQ ID NO: 1) | Amino Acid Substitution |
|---|---|
| V549 | V549P |
| R574 | R574K |
| E570 | E570V |
| G558 | G558T |
| P554 | P554T |
| D555 | D555M |
| G556 | G556P |
| L539 | L539F |
| E538 | E538Q |
| E534 | E534A |
| I532 | I532E |
| L564 | L564C |
| D555 | D555S |
| T556 | T556D |
| T557 | T557A |
| K635 | K635P |
| D607 | D607I |
| Y595 | Y595A |
| S591 | S591I |
| V583 | V583P |
| E578 | E578L |
| K573 | K573R |
| T544 | T544N |
| D545 | D545S |
| T546 | T546D |
| T547 | T547A |
| Y59 | Y59F |
| G75 | G75P |
| L76 | L76Q |
| S87 | S87E |
| H124 | H124D |
| D132 | D132K |
| D133 | D133L |
| C172 | C172V |
| D189 | D189N |
| T190 | T190N |
| T190 | T190D |
| Y201 | Y201D |
| V206 | V206Q |
| N209 | N209E |
| T219 | T219S |
| A229 | A229S |
| A229 | A229D |
| I233 | I233Q |
| F237 | F237Y |
| M250 | M250F |
| A255 | A255P |
| P257 | P257E |
| L268 | L268T |
| K275 | K275E |
| S277 | S277G |
| S277 | S277K |
| Y284 | Y284I |
| H285 | H285G |
| K292 | K292N |
| C318 | C318I |
| H322 | H322Q |
| H322 | H322A |
| M343L | M343L |
| A354 | A354S |
| L359 | L359K |
| G365 | G365D |
| F389 | F389V |
| N417 | N417R |
| Y427 | Y427K |
| Y427 | Y427S |
| S426 | S426Q |
| C462 | C462D |
| C470 | C470M |
| A472 | A472P |
| A472 | A472D |
| N473 | N473T |
| K490 | K490I |
| S491 | S491N |
| N492 | N492G |
| E535 | E535A |

TABLE 1.1-continued

| Amino Acid of Wild-type TcBuster Transposase (SEQ ID NO: 1) | Amino Acid Substitution |
|---|---|
| R536 | R536Q |
| E538 | E538A |
| E567 | E567S |
| F568 | F568Y |
| R574 | R574E |
| R574 | R574I |
| R574 | R574T |
| K590 | K590A |
| S591 | S591K |
| V594 | V594S |
| M612 | M612L |
| M612 | M612S |
| Q615 | Q615K |
| A632 | A632S |
| Y155 | Y155F |
| I421 | I421L |
| A632 | A632Q |
| P559 | P559I |
| G526 | G526V |
| C512 | C512E |
| V356 | V356L |
| Y284 | Y284V |
| N90 | N90S |
| Q18 | Q18A |

An exemplary mutant TcBuster transposase comprises one or more amino acid substitutions, or combinations of substitutions, from Table 2. Sometimes, a mutant TcBuster transposase can comprise at least one of the amino acid substitutions, or combinations of substitutions, from Table 2. A mutant TcBuster transposase can comprise at least 2, at least 3, at least 4, at least 5, at least 6, at least 7, at least 8, at least 9, at least 10, at least 20, at least 30, or more of the amino acid substitutions, or combinations of substitutions, from Table 2.

TABLE 2

| Amino Acid of Wild-type TcBuster Transposase (SEQ ID NO: 1) | Amino Acid Substitution |
|---|---|
| V377 and E469 | V377T/E469K |
| V377, E469, and R536S | V377T/E469K/R536S |
| A332 | A332S |
| V553 and P554 | V553S/P554T |
| E519 | E519R |
| K299 | K299S |
| Q615 and T618 | Q615A/T618K |
| S277 | S277K |
| A303 | A303T |
| P510 | P510D |
| P510 | P510N |
| N281 | N281S |
| N281 | N281E |
| K590 | K590T |
| E274 | E274K |
| Q258 | Q258T |
| E247 | E247K |
| S447 | S447E |
| N85 | N85S |
| V297 | V297K |
| A358 | A358K |
| I452 | I452F |
| V377, E469, D189 | V377T/E469K/D189A |
| K573, E578 | K573E/E578L |
| I452, V377, E469, D189 | I452F/V377T/E469K/D189A |
| A358, V377, E469, D189 | A358K/V377T/E469K/D189A |
| K573, E578, V377, E469, D189 | K573E/E578L/V377T/E469K/D189A |
| T171 | T171R |
| D183 | D183R |

TABLE 2-continued

| Amino Acid of Wild-type TcBuster Transposase (SEQ ID NO: 1) | Amino Acid Substitution |
|---|---|
| S193 | S193R |
| P257 | P257K |
| E263 | E263R |
| L282 | L282K |
| T618 | T618K |
| D622 | D622R |
| E153 | E153K |
| N450 | N450K |
| T171 | T171K |
| D183 | D183K |
| S193 | S193K |
| P257 | P257R |
| E263 | E263K |
| L282 | L282R |
| T618 | T618R |
| D622 | D622K |
| E153 | E153R |
| N450 | N450R |
| E247, E274, V297, A358 | E247K/E274K/V297K/A358K |

An exemplary mutant TcBuster transposase comprises one or more amino acid substitutions, or combinations of substitutions, from Table 3. Sometimes, a mutant TcBuster transposase can comprise at least one of the amino acid substitutions, or combinations of substitutions, from Table 3. A mutant TcBuster transposase can comprise at least 2, at least 3, at least 4, at least 5, at least 6, at least 7, at least 8, at least 9, at least 10, at least 20, at least 30, or more of the amino acid substitutions, or combinations of substitutions, from Table 3.

TABLE 3

| Amino Acid of Wild-type TcBuster Transposase (SEQ ID NO: 1) | Amino Acid Substitutions |
|---|---|
| V377 and E469 | V377T/E469K |
| V377, E469, and R536S | V377T/E469K/R536S |
| A332 | A332S |
| V553 and P554 | V553S/P554T |
| E519 | E519R |
| K299 | K299S |
| Q615 and T618 | Q615A/T618K |
| S277 | S277K |
| A303 | A303T |
| P510 | P510D |
| P510 | P510N |
| N281 | N281S |
| N281 | N281E |
| K590 | K590T |
| E274 | E274K |
| Q258 | Q258T |
| E247 | E247K |
| S447 | S447E |
| N85 | N85S |
| V297 | V297K |
| A358 | A358K |
| I452 | I452F |
| V377, E469, D189 | V377T/E469K/D189A |
| K573, E578 | K573E/E578L |

Hyperactive Mutant TcBuster Transposase

Another aspect of the present disclosure is to provide a hyperactive mutant TcBuster transposase. A "hyperactive" mutant TcBuster transposase, as used herein, can refer to any mutant TcBuster transposase that has increased transposition efficiency as compared to a wild-type TcBuster transposase having amino acid sequence SEQ ID NO: 1.

In some embodiments, a hyperactive mutant TcBuster transposase may have increased transposition efficiency under certain situations as compared to a wild-type TcBuster transposase having amino acid sequence SEQ ID NO: 1. For example, the hyperactive mutant TcBuster transposase may have better transposition efficiency than the wild-type TcBuster transposase when being used to catalyze transposition of transposons having particular types of inverted repeat sequences. It is possible that with some other transposons having other types of inverted repeat sequences, the hyperactive mutant TcBuster transposase does not have increased transposition efficiency in comparison to the wild-type TcBuster transposase. In some other non-limiting examples, the hyperactive mutant TcBuster transposase may have increased transposition efficiency in comparison to a wild-type TcBuster transposase having amino acid sequence SEQ ID NO: 1, under certain transfection conditions. Without being limited, when compared to a wild-type TcBuster transposase, a hyperactive mutant TcBuster transposase may have better transposition efficiency when the temperature is higher than normal cell culture temperature; a hyperactive mutant TcBuster transposase may have better transposition efficiency in a relative acidic or basic aqueous medium; a hyperactive mutant TcBuster transposase may have better transposition efficiency when a particular type of transfection technique (e.g. electroporation) is performed.

Transposition efficiency can be measured by the percent of successful transposition events occurring in a population of host cells normalized by the amount of transposon and transposase introduced into the population of host cells. In many instances, when the transposition efficiency of two or more transposases is compared, the same transposon construct is paired with each of the two or more transposases for transfection of the host cells under same or similar transfection conditions. The amount of transposition events in the host cells can be examined by various approaches. For example, the transposon construct may be designed to contain a reporter gene positioned between the inverted repeats, and transfected cells positive for the reporter gene can be counted as the cells where successful transposition events occurs, which can give an estimate of the amount of the transposition events. Another non-limiting example includes sequencing of the host cell genome to examine the insertion of the cassette cargo of the transposon. In some embodiments, when the transposition efficiency of two or more different transposons is compared, the same transposase can be paired with each of the different transposons for transfection of the host cells under same or similar transfection conditions. Similar approaches can be utilized for the measurement of transposition efficiency. Other methods known to one skilled in the art may also be implemented for the comparison of transposition efficiency.

Also provided herein are methods of obtaining a hyperactive mutant TcBuster transposase.

One exemplary method can comprise systemically mutating amino acids of TcBuster transposase to increase a net charge of the amino acid sequence. Sometimes, the method can comprise performing systematic alanine scanning to mutate aspartic acid (D) or glutamic acid (E), which are negatively charged at a neutral pH, to alanine residues. A method can comprise performing systemic mutation to lysing (K) or arginine (R) residues, which are positively charged at a neutral pH.

Without wishing to be bound by a particular theory, increase in a net charge of the amino acid sequence at a neutral pH may increase the transposition efficiency of the TcBuster transposase. Particularly, when the net charge is increased in proximity to a catalytic domain of the transposase, the transposition efficiency is expected to increase. It can be contemplated that positively charged amino acids can form points of contact with DNA target and allow the catalytic domains to act on the DNA target. It may also be contemplated that loss of these positively charged amino acids can decrease either excision or integration activity in transposases.

FIG. 11 depicts the WT TcBuster transposase amino acid sequence, highlighting amino acids that may be points of contact with DNA. In FIG. 11, large bold lettering indicates catalytic triad amino acids; lettering with boxes indicates amino acids that when substituted to a positive charged amino acid increases transposition; italicized and lower-cased lettering indicates positive charged amino acids that when substituted to a different amino acid decreases transposition; bold italicized and underlined indicates amino acids that when substituted to a positive charged amino acid increases transposition, and when substituted to a negative charged amino acid decreases transposition; underlined lettering indicates amino acids that could be positive charged amino acids based on protein sequence alignment to the Buster subfamily.

A mutant TcBuster transposase can comprise one or more amino acid substitutions that increase a net charge at a neutral pH in comparison to SEQ ID NO: 1. Sometimes, a mutant TcBuster transposase comprising one or more amino acid substitutions that increase a net charge at a neutral pH in comparison to SEQ ID NO: 1 can be hyperactive. Sometimes, the mutant TcBuster transposase can comprise one or more substitutions to a positively charged amino acid, such as, but not limited to, lysine (K) or arginine (R). A mutant TcBuster transposase can comprise one or more substitutions of a negatively charged amino acid, such as, but not limited to, aspartic acid (D) or glutamic acid (E), with a neutral amino acid, or a positively charged amino acid.

One non-limiting example includes a mutant TcBuster transposase that comprises one or more amino acid substitutions that increase a net charge at a neutral pH within or in proximity to a catalytic domain in comparison to SEQ ID NO: 1. The catalytic domain can be the first catalytic domain or the second catalytic domain. The catalytic domain can also include both catalytic domains of the transposase.

An exemplary method of the present disclosure can comprise mutating amino acids that are predicted to be in close proximity to, or to make direct contact with, the DNA. These amino acids can be substituted amino acids identified as being conserved in other member(s) of the hAT family (e.g., other members of the Buster and/or Ac subfamilies). The amino acids predicted to be in close proximity to, or to make direct contact with, the DNA can be identified, for example, by reference to a crystal structure, predicted structures, mutational analysis, functional analysis, alignment with other members of the hAT family, or any other suitable method.

Without wishing to be bound by a particular theory, TcBuster transposase, like other members of the hAT transposase family, has a DDE motif, which may be the active site that catalyzes the movement of the transposon. It is contemplated that D223, D289, and E589 make up the active site, which is a triad of acidic residues. The DDE motif may coordinate divalent metal ions and can be important in the catalytic reaction. In some embodiments, a mutant TcBuster transposase can comprise one or more amino acid substitutions that increase a net charge at a neutral pH in comparison to SEQ ID NO: 1, and the one or more amino acids are located in proximity to D223, D289, or E589, when numbered in accordance to SEQ ID NO: 1.

In certain embodiments, a mutant TcBuster transposase as provided herein does not comprise any disruption of the catalytic triad, i.e. D223, D289, or E589. A mutant TcBuster transposase may not comprise any amino acid substitution at D223, D289, or E589. A mutant TcBuster transposase may comprises amino acid substitution at D223, D289, or E589, but such substitution does not disrupt the catalytic activity contributed by the catalytic triad.

In some cases, the term "proximity" can refer to a measurement of a linear distance in the primary structure of the transposase. For instance, the distance between D223 and D289 in the primary structure of a wild-type TcBuster transposase is 66 amino acids. In certain embodiments, the proximity can refer to a distance of about 70 to 80 amino acids. In many cases, the proximity can refer to a distance of about 80, 75, 70, 60, 50, 40, 30, 20, 10, or 5 amino acids.

In some cases, the term "proximity" can refer to a measurement of a spatial relationship in the secondary or tertiary structure of the transposase, i.e. when the transposase folds into its three dimensional configurations. Protein secondary structure can refer to three dimensional form of local segments of proteins. Common secondary structural elements include alpha helices, beta sheets, beta turns and omega loops. Secondary structure elements may form as an intermediate before the protein folds into its three dimensional tertiary structure. Protein tertiary structure can refer to the three dimensional shape of a protein. Protein tertiary structure may exhibit dynamic configurational change under physiological or other conditions. The tertiary structure will have a single polypeptide chain "backbone" with one or more protein secondary structures, the protein domains. Amino acid side chains may interact and bond in a number of ways. The interactions and bonds of side chains within a particular protein determine its tertiary structure. In many implementations, the proximity can refer to a distance of about 1 Å, about 2 Å, about 5 Å, about 8 Å, about 10 Å, about 15 Å, about 20 Å, about 25 Å, about 30 Å, about 35 Å, about 40 Å, about 50 Å, about 60 Å, about 70 Å, about 80 Å, about 90 Å, or about 100 Å.

A neutral pH can be a pH value around 7. Sometimes, a neutral pH can be a pH value between 6.9 and 7.1, between 6.8 and 7.2, between 6.7 and 7.3, between 6.6 and 7.4, between 6.5 and 7.5, between 6.4 and 7.6, between 6.3 and 7.7, between 6.2-7.8, between 6.1-7.9, between 6.0-8.0, between 5-8, or in a range derived therefrom.

Non-limiting exemplary mutant TcBuster transposases that comprise one or more amino acid substitutions that increase a net charge at a neutral pH in comparison to SEQ ID NO: 1 include TcBuster transposases comprising at least one of the combinations of amino acid substitutions from Table 4, Table 4.1, or both. A mutant TcBuster transposase can comprise at least 2, at least 3, at least 4, at least 5, at least 6, at least 7, at least 8, at least 9, at least 10, at least 20, at least 30, or more of the amino acid substitutions from Table 4, Table 4.1, or both.

In some embodiments, a mutant TcBuster transposase can comprise one or more amino acid substitutions that increase a net charge at a non-neutral pH in comparison to SEQ ID NO: 1. In some cases, the net charge is increased within or in proximity to a catalytic domain at a non-neutral pH. In many cases, the net charge is increased in proximity to D223, D289, or E589, at a non-neutral pH. The non-neutral pH can be a pH value lower than 7, lower than 6.5, lower than 6, lower than 5.5, lower than 5, lower than 4.5, lower than 4, lower than 3.5, lower than 3, lower than 2.5, lower than 2, lower than 1.5, or lower than 1. The non-neutral pH can also be a pH value higher than 7, higher than 7.5, higher than 8, higher than 8.5, higher than 9, higher than 9.5, or higher than 10.

TABLE 4

| Amino Acid of Wild-type TcBuster Transposase (SEQ ID NO: 1) | Amino Acid Substitutions |
|---|---|
| E247 | E247K |
| E274 | E274K |
| V297 | V297K |
| A358 | A358K |
| S277 | S277K |
| E247 | E247R |
| E274 | E274R |
| V297 | V297R |
| A358 | A358R |
| S277 | S277R |
| T171 | T171R |
| D183 | D183R |
| S193 | S193R |
| P257 | P257K |
| E263 | E263R |
| L282 | L282K |
| T618 | T618K |
| D622 | D622R |
| E153 | E153K |
| N450 | N450K |
| T171 | T171K |
| D183 | D183K |
| S193 | S193K |
| P257 | P257R |
| E263 | E263K |
| L282 | L282R |
| T618 | T618R |
| D622 | D622K |
| E153 | E153R |
| N450 | N450R |

TABLE 4.1

| Amino Acid of Wild-type TcBuster Transposase (SEQ ID NO: 1) | Amino Acid Substitutions |
|---|---|
| D132 | D132K |
| S277 | S277K |
| L359 | L359K |
| N417 | N417R |
| Y427 | Y427K |
| S591 | S591K |
| Q615 | Q615K |

In one exemplary embodiment, a method can comprise systemically mutating amino acids in the DNA Binding and Oligomerization domain. Without wishing to be bound by a particular theory, mutation in the DNA Binding and Oligomerization domain may increase the binding affinity to DNA target and promote oligomerization activity of the transposase, which consequentially may promote transposition efficiency. More specifically, the method can comprise systemically mutating amino acids one by one within or in proximity to the DNA Binding and Oligomerization domain (e.g., amino acid 112 to 213). The method can also comprise mutating more than one amino acid within or in proximity to the DNA Binding and Oligomerization domain. The method can also comprise mutating one or more amino acids within or in proximity to the DNA Binding and Oligomerization domain, together with one or more amino acids outside the DNA Binding and Oligomerization domain.

In some embodiments, the method can comprise performing rational replacement of selective amino acid residues based on multiple sequence alignments of TcBuster with other hAT family transposases (Ac, Hermes, Hobo, Tag2, Tam3, Hermes, Restless and Tol2) or with other members of Buster subfamily (e.g., AeBuster1, AeBuster2, AeBuster3, BtBuster1, BtBuster2, CfBuster1, and CfBuster2). Without being bound by a certain theory, conservancy of certain amino acids among other hAT family transposases, especially among the active ones, may indicate their importance for the catalytic activity of the transposases. Therefore, replacement of unconserved amino acids in wild-type TcBuster sequence (SEQ ID NO: 1) with conserved amino acids among other hAT family may yield hyperactive mutant TcBuster transposase. The method may comprise obtaining sequences of TcBuster as well as other hAT family transposases; aligning the sequences and identifying the amino acids in TcBuster transposase with a different conserved counterpart among the other hAT family transposases; performing site-directed mutagenesis to produce mutant TcBuster transposase harboring the mutation(s).

A hyperactive mutant TcBuster transposase can comprise one or more amino acid substitutions based on alignment to other members of Buster subfamily or other members of hAT family. In many cases, the one or more amino acid substitutions can be substitutions of conserved amino acid for the unconserved amino acid in wild-type TcBuster sequence (SEQ ID NO: 1). Non-limiting examples of mutant TcBuster transposases include TcBuster transposases comprising at least one of the amino acid substitutions from Table 5, Table 5.1, or both. A mutant TcBuster transposase can comprise at least 2, at least 3, at least 4, at least 5, at least 6, at least 7, at least 8, at least 9, at least 10, at least 20, at least 30, or more of the amino acid substitutions from Table 5, Table 5.1, or both.

Another exemplary method can comprise systemically mutating acidic amino acids to basic amino acids and identifying hyperactive mutant transposase.

In some cases, mutant TcBuster transposase can comprise amino acid substitutions V377T, E469K, and D189A. A mutant TcBuster transposase can comprise amino acid substitutions K573E and E578L. A mutant TcBuster transposase can comprise amino acid substitution 1452K. A mutant TcBuster transposase can comprise amino acid substitution A358K. A mutant TcBuster transposase can comprise amino acid substitution V297K. A mutant TcBuster transposase can comprise amino acid substitution N85S. A mutant TcBuster transposase can comprise amino acid substitutions N85S, V377T, E469K, and D189A. A mutant TcBuster transposase can comprise amino acid substitutions I452F, V377T, E469K, and D189A. A mutant TcBuster transposase can comprise amino acid substitutions A358K, V377T, E469K, and D189A. A mutant TcBuster transposase can comprise amino acid substitutions V377T, E469K, D189A, K573E and E578L.

TABLE 5

| Amino Acid of Wild-type TcBuster Transposase (SEQ ID NO: 1) | Amino Acid Substitution |
|---|---|
| Q151 | Q151S |
| Q151 | Q151A |
| A154 | A154P |
| Q615 | Q615A |
| V553 | V553S |
| Y155 | Y155H |

TABLE 5-continued

| Amino Acid of Wild-type TcBuster Transposase (SEQ ID NO: 1) | Amino Acid Substitution |
|---|---|
| Y201 | Y201A |
| F202 | F202D |
| F202 | F202K |
| C203 | C203I |
| C203 | C203V |
| F400 | F400L |
| I398 | I398D |
| I398 | I398S |
| I398 | I398K |
| V431 | V431L |
| P559 | P559D |
| P559 | P559S |
| P559 | P559K |
| M222 | M222L |
| V549 | V549P |
| R574 | R574K |
| E570 | E570V |
| G558 | G558T |
| P554 | P554T |
| D555 | D555M |
| G556 | G556P |
| L539 | L539F |
| E538 | E538Q |
| E534 | E534A |
| I532 | I532E |
| L564 | L564C |
| D555 | D555S |
| T556 | T556D |
| T557 | T557A |
| K635 | K635P |
| D622 | D622R |
| D607 | D607I |
| Y595 | Y595L |
| S591 | S591I |
| V583 | V583P |
| E578 | E578L |
| K573 | K573E |
| T544 | T544N |
| D545 | D545S |
| T546 | T546D |
| T547 | T547A |

TABLE 5.1

| Amino Acid of Wild-type TcBuster Transposase (SEQ ID NO: 1) | Amino Acid Substitution |
|---|---|
| Y59 | Y59F |
| G75 | G75P |
| L76 | L76Q |
| S87 | S87E |
| H124 | H124D |
| D133 | D133L |
| C172 | C172V |
| D189 | D189N |
| T190 | T190N |
| T190 | T190D |
| Y201 | Y201D |
| V206 | V206Q |
| N209 | N209E |
| T219 | T219S |
| A229 | A229S |
| A229 | A229D |
| I233 | I233Q |
| F237 | F237Y |

TABLE 5.1-continued

| Amino Acid of Wild-type TcBuster Transposase (SEQ ID NO: 1) | Amino Acid Substitution |
|---|---|
| M250 | M250F |
| A255 | A255P |
| P257 | P257E |
| L268 | L268T |
| K275 | K275E |
| S277 | S277G |
| Y284 | Y284I |
| H285 | H285G |
| K292 | K292N |
| C318 | C318I |
| H322 | H322Q |
| H322 | H322A |
| M343L | M343L |
| A354 | A354S |
| G365 | G365D |
| F389 | F389V |
| Y427 | Y427S |
| S426 | S426Q |
| C462 | C462D |
| C470 | C470M |
| A472 | A472P |
| A472 | A472D |
| N473 | N473T |
| K490 | K490I |
| S491 | S491N |
| N492 | N492G |
| E535 | E535A |
| R536 | R536Q |
| E538 | E538A |
| E567 | E567S |
| F568 | F568Y |
| R574 | R574E |
| R574 | R574I |
| R574 | R574T |
| K590 | K590A |
| V594 | V594S |
| M612 | M612L |
| M612 | M612S |
| A632 | A632S |
| Y155 | Y155F |
| I421 | I42IL |
| A632 | A632Q |
| P559 | P559I |
| G526 | G526V |
| C512 | C512E |
| V356 | V356L |
| Y284 | Y284V |
| N90 | N90S |

Nuclear Localization Signal

Another aspect of the present disclosure provides a fusion TcBuster transposase with one or more additional Nuclear Localization Signal (NLS) sequences. Wild-type TcBuster transposase (SEQ ID NO: 1) contains two putative monopartite NLS sequences RKKR and KKRK. In some embodiments of the present disclosure, a fusion TcBuster transposase as provided herein can comprise additional monopartite NLS sequences created through amino acid substitutions. In some cases, the additional monopartite NLS sequences can have a sequence K(K/R)X(K/R), where X represents any amino acid. In some cases, the fusion TcBuster transposase comprising additional monopartite NLS sequences as provided herein can have increased transposition efficiency as compared to an otherwise identical TcBuster transposase that does not have the additional monopartite NLS sequence.

In some embodiments, a fusion TcBuster transposase as provided herein comprises at least 1, at least 2, at least 3, at least 4, or at least 5 additional NLS sequences. In some cases, the additional NLS sequences include the ones listed in Table 6. As provided herein, the additional NLS sequences can be fused to the N-terminal end, C-terminal end, and/or the internal part of the TcBuster transposase.

Exemplary TcBuster transposase comprising bipartite NLS sequences as provided herein can have NLS sequences like K(K/R)XXXXXXXXXXXX(K/R)(K/R)(K/R)(K/R) (SEQ ID NO: 208), K(K/R)XXXXXXXXXXX(K/R)(K/R)(K/R)(K/R) (SEQ ID NO: 209), K(K/R)XXXXXXXXXX(K/R)(K/R)(K/R)(K/R) (SEQ ID NO: 210), K(K/R)XXXXXXXXX(K/R)(K/R)(K/R)(K/R) (SEQ ID NO: 211), K(K/R)XXXXXXXX(K/R)(K/R)(K/R)(K/R) (SEQ ID NO: 212), or K(K/R)XXXXXXX(K/R)(K/R)(K/R)(K/R) (SEQ ID NO: 213), wherein X represents any amino acid.

TABLE 6

Exemplary Nuclear Localization Signals

| Nuclear Localization signal | Amino acid sequence | SEQ ID NO: |
|---|---|---|
| SV40 | PKKKRKV | 214 |
| Nucleoplasmin | AVKRPAATKKAGQAKKKKLD | 215 |
| Myc | PAAKRVKLD | 216 |
| hnRNPK | KRPAEDMEEEQAFKRSR | 217 |
| viral TAT-NLS | GRKKRRQRRRAP | 218 |
| human ribosomal protein S7 | KRPR | 219 |
| M9 | GNYNNQSSNFGPMKGGNFGGRSSGPYGGGGQ YFAKPRNQGGY | 220 |

Fusion Transposase with DNA Binding Domain

Another aspect of the present disclosure provides a fusion transposase. The fusion transposase can comprise a TcBuster transposase sequence and a DNA sequence specific binding domain.

The TcBuster transposase sequence of a fusion transposase can comprise an amino acid sequence of any of the mutant TcBuster transposases as described herein. The TcBuster transposase sequence of a fusion transposase can also comprise an amino acid sequence of a wild-type TcBuster transposase having amino acid sequence SEQ ID NO: 1.

A DNA sequence specific binding domain as described herein can refer to a protein domain that is adapted to bind to a DNA molecule at a sequence region ("target sequence") containing a specific sequence motif. For instance, an exemplary DNA sequence specific binding domain may selectively bind to a sequence motif TATA, while another exemplary DNA sequence specific binding domain may selectively bind to a different sequence motif ATGCNTAGAT (SEQ ID NO: 82) (N denotes any one of A, T, G, and C).

A fusion transposase as provided herein may direct sequence specific insertion of the transposon. For instance, a DNA sequence specific binding domain may guide the fusion transposase to bind to a target sequence based on the binding specificity of the binding domain. Being bound to or restricted to a certain sequence region may spatially limit the interaction between the fusion transposase and the transposon, thereby limiting the catalyzed transposition to a sequence region in proximity to the target sequence. Depending on the size, three-dimensional configuration, and sequence binding affinity of the DNA binding domain, as well as the spatial relationship between the DNA binding domain and the TcBuster transposase sequence, and the flexibility of the connection between the two domains, the distance of the actual transposition site to the target sequence may vary. Proper design of the fusion transposase configuration can direct the transposition to a desirable target genomic region.

A target genomic region for transposition can be any particular genomic region, depending on application purposes. For instance, sometimes, it is desirable to avoid transcription start sites for the transposition, which may cause undesirable, or even harmful, change in expression level of certain important endogenous gene(s) of the cell. A fusion transposase may contain a DNA sequence specific binding domain that can target the transposition to a safe harbor of the host genome. Non-limiting examples of safe harbors can include HPRT, AAVS site (e.g. AAVS1, AAVS2, ETC.), CCR5, or Rosa26. Safe harbor sites can generally refer to sites for transgene insertion whose use exert little to none disrupting effects on genome integrity of the cell or cellular health and functions.

A DNA sequence specific binding domain may be derived from, or be a variant of any DNA binding protein that has sequence-specificity. In many instances, a DNA sequence specific binding domain may comprise an amino acid sequence at least 40%, at least 50%, at least 60%, at least 70%, at least 80%, at least 90%, at least 95%, at least 98%, at least 99%, or 100% identical to a naturally occurring sequence-specific DNA binding protein. A DNA sequence specific binding domain may comprise an amino acid sequence at least 70% identical to a naturally occurring sequence-specific DNA binding protein. Non-limiting examples of a naturally occurring sequence-specific DNA binding protein include, but not limited to, transcription factors from various origins, specific-sequence nucleases, and viral replication proteins. A naturally occurring sequence-specific DNA binding protein can also be any other protein having the specific binding capability from various origins. Selection and prediction of DNA binding proteins can be conducted by various approaches, including, but not limited to, using computational prediction databases available online, like DP-Bind (http://lcg.rit.albany.edu/dp-bind/) or DNABIND (http://dnabind.szialab.org/)

The term "transcription factor" can refer to a protein that controls the rate of transcription of genetic information from DNA to messenger DNA, by binding to a specific DNA sequence. A transcription factor that can be used in a fusion transposase described herein can be based on a prokaryotic transcription factor or a eukaryotic transcription factor, as long as it confers sequence specificity when binding to the target DNA molecule. Transcription factor prediction databases such as DBD (transcriptionfactor.org) may be used for selection of appropriate transcription factor for application of the disclosure herein.

A DNA sequence specific binding domain as used herein can comprise one or more DNA binding domain from a naturally occurring transcription factor. Non-limiting examples of DNA binding domains of transcription factors include DNA binding domains that belong to families like basic helix-loop-helix, basic-leucine zipper (bZIP), C-terminal effector domain of the bipartite response regulators, AP2/ERF/GCC box, helix-turn-helix, homeodomain proteins, lambda repressor-like, srf-like (serum response factor), paired box, winged helix, zinc fingers, multi-domain Cys2His2 (C2H2) zinc fingers, Zn2/Cys6, or Zn2/Cys8 nuclear receptor zinc finger.

A DNA sequence specific binding domain can be an artificially engineered amino acid sequence that binds to specific DNA sequences. Non-limiting examples of such artificially designed amino acid sequence include sequences created based on frameworks like transcription activator like effector nucleases (TALEs) DNA binding domain, zinc finger nucleases, adeno associated virus (AAV) Rep protein, and any other suitable DNA binding proteins as described herein.

Natural TALEs are proteins secreted by Xanthomonas bacteria to aid the infection of plant species. Natural TALEs can assist infections by binding to specific DNA sequences and activating the expression of host genes. In general, TALE proteins consist of a central repeat domain, which determines the DNA targeting specificity and can be rapidly synthesized de novo. TALEs have a modular DNA-binding domain (DBD) containing repetitive sequences of residues. In some TALEs, each repeat region contains 34 amino acids. The term "TALE domain" as used herein can refer to the modular DBD of TALEs. A pair of residues at the 12th and 13th position of each repeat region can determine the nucleotide specificity and are referred to as the repeat variable diresidue (RVD). The last repeat region, termed the half-repeat, is typically truncated to 20 amino acids. Combining these repeat regions allows synthesizing sequence-specific synthetic TALEs. The C-terminus typically contains a nuclear localization signal (NLS), which directs a TALE to the nucleus, as well as a functional domain that modulates transcription, such as an acidic activation domain (AD). The endogenous NLS can be replaced by an organism-specific localization signal. For example, an NLS derived from the simian virus 40 large T-antigen can be used in mammalian cells. The RVDs HD, NG, NI, and NN target C, T, A, and G/A, respectively. A list of RVDs and their binding preferences under certain circumstances for nucleotides can be found in Table 7. Additional TALE RVDs can also be used for custom degenerate TALE-DNA interactions. For example, NA has high affinity for all four bases of DNA. Additionally, N*, where * is an RVD with a deletion in the 13th residue, can accommodate all letters of DNA including methylated cytosine. Also S* may have the ability to bind to any DNA nucleotide.

A number of online tools are available for designing TALEs to target a specific DNA sequence, for example TALE-NT (https://tale-nt.cac.cornell.edu/), Mojo hand (talendesign.org/). Commercially available kits may also assist in creating custom assembly of TALE repeat regions between the N and C-terminus of the protein. These methods can be used to assemble custom DBDs, which are then cloned into an expression vector containing a functional domain, e.g. TcBuster transposase sequence.

TABLE 7

RVD Binding Preference

| | nucleotides | | | |
|---|---|---|---|---|
| RVD | A | G | C | T |
| NN | medium | medium | | |
| NK | | weak | | |
| NI | medium | | | |
| NG | | | | weak |
| HD | | | medium | |
| NS | weak | medium | weak | weak |
| NG | | | | weak |
| N* | | | weak | weak |
| HN | weak | medium | | |
| NT | weak | medium | | |
| NP | weak | | weak | medium |
| NH | | medium | | |
| SN | | weak | | |
| SH | | weak | | |
| NA | weak | strong | weak | weak |
| IG | | | | weak |
| H* | poor | poor | weak | poor |
| ND | | | weak | |
| HI | medium | | | |
| HG | | | | weak |
| NC | | | | weak |
| NQ | | weak | | |
| SS | | weak | | |
| SN | | weak | | |
| S* | medium | medium | strong | medium |
| NV | weak | medium | poor | poor |
| HH | poor | poor | poor | poor |
| YG | poor | poor | poor | poor |

TALEs can be synthesized de novo in the laboratory, for example, by combining digestion and ligation steps in a Golden Gate reaction with type II restriction enzymes. Alternatively, TALE can be assembled by a number of different approaches, including, but not limited to, Ligation-Independent Cloning (LIC), Fast Ligation-based Automatable Solid-phase High-throughput (FLASH) assembly, and Iterative-Capped Assembly (ICA).

Zinc fingers (ZF) are ~30 amino acids that can bind to a limited combination of ~3 nucleotides. The C2H2 ZF domain may be the most common type of ZF and appears to be one of the most abundantly expressed proteins in eukaryotic cells. ZFs are small, functional and independently folded domains coordinated with zinc molecules in their structure. Amino acids in each ZF can have affinity towards specific nucleotides, causing each finger to selectively recognize 3-4 nucleotides of DNA. Multiple ZFs can be arranged into a tandem array and recognize a set of nucleotides on the DNA. By using a combination of different zinc fingers, a unique DNA sequence within the genome can be targeted. Different ZFPs of various lengths can be generated, which may allow for recognition of almost any desired DNA sequence out of the possible 64 triplet subsites.

Zinc fingers to be used in connection with the present disclosure can be created using established modular assembly fingers, such as a set of modular assembly finger domains developed by Barbas and colleagues, and also another set of modular assembly finger domains by ToolGen. Both set of domains cover all 3 bp GNN, most ANN, many CNN and some TNN triplets (where N can be any of the four nucleotides). Both have a different set of fingers, which allows for searching and coding different ZF modules as needed. A combinatorial selection-based oligomerized pool engineering (OPEN) strategy can also be employed to minimize context-dependent effects of modular assembly involving the position of a finger in the protein and the sequence of neighboring fingers. OPEN ZF arrays are publicly available from the Zinc Finger Consortium Database.

AAV Rep DNA-binding domain is another DNA sequence specific binding domain that can be used in connection with the subject matter of the present disclosure. Viral cis-acting inverted terminal repeats (ITRs), and the trans-acting viral Rep proteins (Rep) are believed to be the factors mediating preferential integration of AAV into AAVS1 site of the host genome in the absence of a helper virus. AAV Rep protein can bind to specific DNA sequence in the AAVS1 site. Therefore, a site-specific DNA-binding domain can be fused together with a TcBuster transposase domain as described herein.

A fusion transposase as provided herein can comprise a TcBuster transposase sequence and a tag sequence. A tag sequence as provide herein can refer to any protein sequence that can be used as a detection tag of the fusion protein, such as, but not limited to, reporter proteins and affinity tags that can be recognized by antibodies. Reporter proteins include, but not limited to, fluorescent proteins (e.g. GFP, RFP, mCherry, YFP), β-galactosidase β-gal), alkaline phosphatase (AP), chloramphenicol acetyl transferase (CAT), horseradish peroxidase (HRP). Non-limiting examples of affinity tags include polyhistidine (His tag), Glutathione S-Transferase (GST), Maltose Binding Protein (MBP), Calmodulin Binding Peptide (CBP), intein-chitin binding domain (intein-CBD), Streptavidin/Biotin-based tags, Epitope tags like FLAG, HA, c-myc, T7, Glu-Glu and many others.

Figure 8:
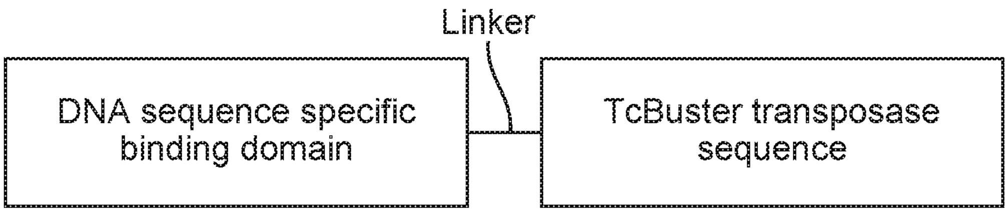
FIG. 8 depicts one exemplary fusion transposase that contains a DNA sequence specific binding domain and a TcBuster transposase sequence joined by an optional linker.

A fusion transposase as provided herein can comprise a TcBuster transposase sequence and a DNA sequence specific binding domain or a tag sequence fused together without any intermediate sequence (e.g., "back-to-back"). In some cases, a fusion transposase as provided herein can comprise a TcBuster transposase sequence and a DNA sequence specific binding domain or a tag sequence joined by a linker sequence. FIG. 8 is a schematic of an exemplary fusion transposase that comprises a DNA sequence specific binding domain and a TcBuster transposase sequence, joined by a linker. In an exemplary fusion transposase, a linker may serve primarily as a spacer between the first and second polypeptides. A linker can be a short amino acid sequence to separate multiple domains in a single polypeptide. A linker sequence can comprise linkers occurring in natural multi-domain proteins. In some instances, a linker sequence can comprise linkers artificially created. The choice of linker sequence may be based on the application of the fusion transposase. A linker sequence can comprise 3, 4, 5, 6, 7, 8, 9, 10, or more amino acids. In some embodiments, the linker sequence may comprise at least 3, at least 4, at least 5, at least 6, at least 7, at least 8, at least 9, at least 10, at least 15, at least 20, or at least 50 amino acids. In some embodiments, the linker sequence can comprise at most 4, at most 5, at most 6, at most 7, at most 8, at most 9, at most 10, at most 11, at most 12, at most 15, at most 20, at most 30, at most 40, at most 50, or at most 100 amino acids. In certain cases, it may be desirable to use flexible linker sequences, such as, but not limited to, stretches of Gly and Ser residues ("GS" linker) like (GGGGS)n (n=2-8) (SEQ ID NO: 83), $(Gly)_8$ (SEQ ID NO: 84), GSAGSAAGSGEF (SEQ ID NO: 85), $(GGGGS)_4$ (SEQ ID NO: 86). Sometimes, it may be desirable to use rigid linker sequences, such as, but not limited to, (EAAAK)n (n=2-7) (SEQ ID NO: 87), Pro-rich sequences like (XP)n, with X designating any amino acid.

In an exemplary fusion transposase provided herein, a TcBuster transposase sequence can be fused to the N-terminus of a DNA sequence specific binding domain or a tag sequence. Alternatively, a TcBuster transposase sequence can be fused to the C-terminus of a DNA sequence specific binding domain or a tag sequence. In some embodiments, a third domain sequence or more of other sequences can be present in between the TcBuster transposase and the DNA sequence specific binding domain or the tag sequence, depending on the application of the fusion transposase.

Nucleotide Sequence of TcBuster

Another aspect of the present disclosure provides polynucleotides, e.g., nucleotide sequences, coding for a TcBuster transposase as provided herein. In some embodiments, the polynucleotides as provided herein comprise one or more codons that are favorable by a translation system of the organism whose cell the polynucleotide is delivered into. For example, a polynucleotide as provided herein can comprise one or more codons that are favorable by a human (e.g., *Homo sapiens*) translation system, when the polynucleotide is delivered to a human cell for genome editing purposes. In some embodiments, one or more codons in the polynucleotides coding for a TcBuster transposase as provided herein can be codons that are found at a higher frequency in the organism whose cell the polynucleotide is delivered into. Without being bound by a certain theory, in some cases, the TcBuster transposase as provided herein is delivered to a target cell in the form of a polynucleotide coding for it, and the codons of a high frequency in the target cell can be utilized by the translation system of the cell more efficiently as compared to the natural codons in the DNA coding for TcBuster transposase, thereby leading to an increased expression of the TcBuster transposase in the target cell.

Certain embodiments of the polynucleotide as provided herein can comprise at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, or at least 200 codons that are replaced with codons that are favorable by the organism whose cell the polynucleotide is delivered into. Certain embodiments of the polynucleotide can comprise one or more codons that are found at high frequency in *Homo sapiens*, such as the ones with high frequency/thousand (or fraction) listed in Table 8. In some cases, the codons in Table 8 are selected if their frequency/thousand in *Homo sapiens* is at least 5, at least 6, at least 8, at least 10, at least 12, at least 14, at least 16, at least 18, at least 20, at least 25, or at least 30. In some cases, the codons Table 8 are selected if their fraction in *Homo sapiens* is at least 0.1, at least 0.12, at least 0.14, at least 0.16, at least 0.18, at least 0.2, at least 0.22, at least 0.24, at least 0.26, at least 0.28, at least 0.3, at least 0.35, at least 0.4, at least 0.45, at least 0.5, or at least 0.55.

In some embodiments, the polynucleotides provided herein are codon optimized for expression in cells of a target species, e.g., human cells. A polynucleotide can be codon optimized for expression in cells of a target species, for instance, at least 70%, 75%, 80%, 85%, 90%, 95%, 98%, 99%, or 100% of codons in the polynucleotide exist at a high frequency in the target species (e.g., at least 5, at least 6, at least 8, at least 10, at least 12, at least 14, at least 16, at least 18, at least 20, at least 25, or at least 30 frequency/thousands in the target species, or e.g., at least 0.1, at least 0.12, at least 0.14, at least 0.16, at least 0.18, at least 0.2, at least 0.22, at least 0.24, at least 0.26, at least 0.28, at least 0.3, at least 0.35, at least 0.4, at least 0.45, at least 0.5, or at least 0.55 fraction in the target species. In some embodiments, the polynucleotide is codon optimized for expression in cells of a target species, for instance, at least 80%, 85%, 90%, 95%, 98%, 99%, or 100% of codons in the polynucleotide exist at a high frequency in the target species (e.g., at least 20, at least 25, or at least 30 frequency/thousands in the target species, or at least 0.2, at least 0.22, at least 0.24, at least 0.26, at least 0.28, at least 0.3, at least 0.35, at least 0.4, at least 0.45, at least 0.5, or at least 0.55 fraction in the target species.

SEQ ID NO: 204 is an exemplary DNA sequence that is codon optimized for expression in human cells and encodes a wild-type TcBuster transposase. SEQ ID NO: 207 is an exemplary mRNA sequence that is codon optimized for expression in human cells and encodes a wild-type TcBuster transposase. A polynucleotide provided herein can comprise a nucleotide sequence at least about 70%, 75%, 80%, 85%, 90%, 95%, or 98% identical to or complementary with full length SEQ ID NO: 204 or 207. In some embodiments, the polynucleotide has a nucleotide sequence at least about 80%, 85%, 90%, 95%, or 98% identical to or complementary with full length SEQ ID NO: 204 or 207. In some embodiments, the polynucleotide has a nucleotide sequence at least about 95% identical to or complementary with full length SEQ ID NO: 204 or 207.

TABLE 8

Codon usage table for *Homo Sapiens*

| Triplet | Amino acid | Fraction | Frequency/ Thousand | Number | Triplet | Amino acid | Fraction | Frequency/ Thousand | Number |
|---|---|---|---|---|---|---|---|---|---|
| TTT | F | 0.45 | 16.9 | 336562 | TCT | S | 0.18 | 14.6 | 291040 |
| TTC | F | 0.55 | 20.4 | 406571 | TCC | S | 0.22 | 17.4 | 346943 |
| TTA | L | 0.07 | 7.2 | 143715 | TCA | S | 0.15 | 11.7 | 233110 |
| TTG | L | 0.13 | 12.6 | 249879 | TCG | S | 0.06 | 4.5 | 89429 |
| TAT | Y | 0.43 | 12 | 239268 | TGT | C | 0.45 | 9.9 | 197293 |
| TAC | Y | 0.57 | 15.6 | 310695 | TGC | C | 0.55 | 12.2 | 243685 |

TABLE 8-continued

Codon usage table for *Homo Sapiens*

| Triplet | Amino acid | Fraction | Frequency/ Thousand | Number | Triplet | Amino acid | Fraction | Frequency/ Thousand | Number |
|---|---|---|---|---|---|---|---|---|---|
| TAA | * | 0.28 | 0.7 | 14322 | TGA | * | 0.52 | 1.3 | 25383 |
| TAG | * | 0.2 | 0.5 | 10915 | TGG | W | 1 | 12.8 | 255512 |
| CTT | L | 0.13 | 12.8 | 253795 | CCT | P | 0.28 | 17.3 | 343793 |
| CTC | L | 0.2 | 19.4 | 386182 | CCC | P | 0.33 | 20 | 397790 |
| CTA | L | 0.07 | 6.9 | 138154 | CCA | P | 0.27 | 16.7 | 331944 |
| CTG | L | 0.41 | 40.3 | 800774 | CCG | P | 0.11 | 7 | 139414 |
| CAT | H | 0.41 | 10.4 | 207826 | CGT | R | 0.08 | 4.7 | 93458 |
| CAC | H | 0.59 | 14.9 | 297048 | CGC | R | 0.19 | 10.9 | 217130 |
| CAA | Q | 0.25 | 11.8 | 234785 | CGA | R | 0.11 | 6.3 | 126113 |
| CAG | Q | 0.75 | 34.6 | 688316 | CGG | R | 0.21 | 11.9 | 235938 |
| ATT | I | 0.36 | 15.7 | 313225 | ACT | T | 0.24 | 12.8 | 255582 |
| ATC | I | 0.48 | 21.4 | 426570 | ACC | T | 0.36 | 19.2 | 382050 |
| ATA | I | 0.16 | 7.1 | 140652 | ACA | T | 0.28 | 14.8 | 294223 |
| ATG | M | 1 | 22.3 | 443795 | ACG | T | 0.12 | 6.2 | 123533 |
| AAT | N | 0.46 | 16.7 | 331714 | AGT | S | 0.15 | 11.9 | 237404 |
| AAC | N | 0.54 | 19.5 | 387148 | AGC | S | 0.24 | 19.4 | 385113 |
| AAA | K | 0.42 | 24 | 476554 | AGA | R | 0.2 | 11.5 | 228151 |
| AAG | K | 0.58 | 32.9 | 654280 | AGG | R | 0.2 | 11.4 | 227281 |
| GTT | V | 0.18 | 10.9 | 216818 | GCT | A | 0.26 | 18.6 | 370873 |
| GTC | V | 0.24 | 14.6 | 290874 | GCC | A | 0.4 | 28.5 | 567930 |
| GTA | V | 0.11 | 7 | 139156 | GCA | A | 0.23 | 16 | 317338 |
| GTG | V | 0.47 | 28.9 | 575438 | GCG | A | 0.11 | 7.6 | 150708 |
| GAT | D | 0.46 | 22.3 | 443369 | GGT | G | 0.16 | 10.8 | 215544 |
| GAC | D | 0.54 | 26 | 517579 | GGC | G | 0.34 | 22.8 | 453917 |
| GAA | E | 0.42 | 29 | 577846 | GGA | G | 0.25 | 16.3 | 325243 |
| GAG | E | 0.58 | 40.8 | 810842 | GGG | G | 0.25 | 16.4 | 326879 |

TcBuster Transposon

Another aspect of the present disclosure provides a TcBuster transposon that comprises a cassette cargo positioned between two inverted repeats. A TcBuster transposon can be recognized by a TcBuster transposase as described herein, e.g., a TcBuster transposase can recognize the TcBuster transposon and catalyze transposition of the TcBuster transposon into a DNA sequence.

The terms "inverted repeats", "terminal inverted repeats", "inverted terminal repeats", as used interchangeably herein, can refer to short sequence repeats flanking the transposase gene in a natural transposon or a cassette cargo in an artificially engineered transposon. The two inverted repeats are generally required for the mobilization of the transposon in the presence of a corresponding transposase. Inverted repeats as described herein may contain one or more direct repeat (DR) sequences. These sequences usually are embedded in the terminal inverted repeats (TIRs) of the elements. The term "cargo cassette" as used herein can refer to a nucleotide sequence other than a native nucleotide sequence between the inverted repeats that contains the TcBuster transposase gene. A cargo cassette can be artificially engineered.

Figure 2:
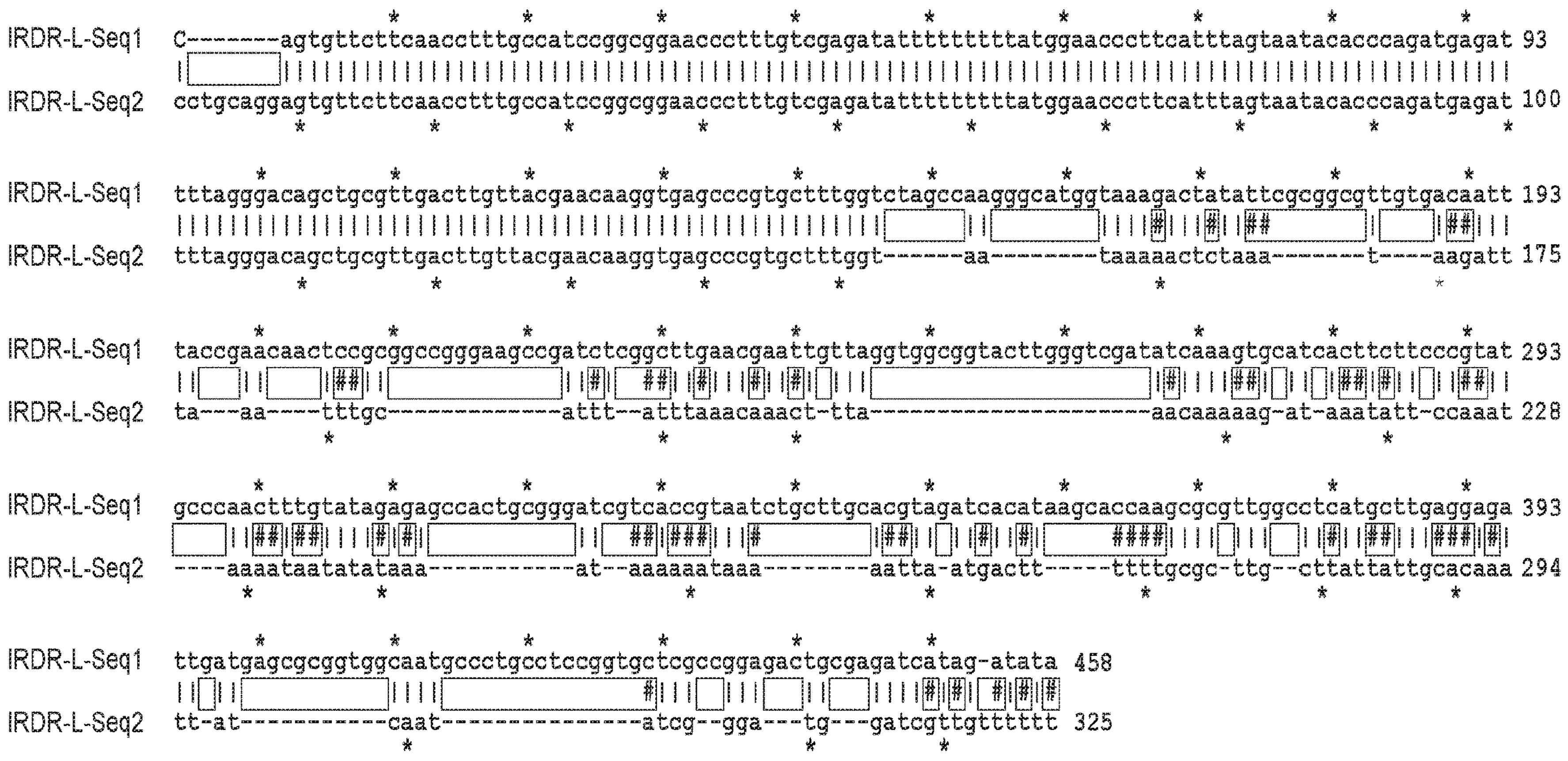
FIG. 2 shows nucleotide sequence comparison of exemplary TcBuster IR/DR sequence 1 (SEQ ID NOS 3-4, respectively in order of appearance) and sequence 2 (SEQ ID NOS 5-6, respectively in order of appearance).

A transposon described herein may contain a cargo cassette flanked by IR/DR sequences. In some embodiments, at least one of the repeats contains at least one direct repeat. As shown in FIGS. 1 and 2, a transposon may contain a cargo cassette flanked by IRDR-L-Seq1 (SEQ ID NO: 3) and IRDR-R-Seq1 (SEQ ID NO: 4). In many cases, a left inverted repeat can comprise a sequence at least 40%, at least 50%, at least 60%, at least 70%, at least 80%, at least 90%, at least 95%, at least 98%, at least 99%, or 100% identical to IRDR-L-Seq1 (SEQ ID NO: 3). Sometimes, a right inverted repeat can comprise a sequence at least 40%, at least 50%, at least 60%, at least 70%, at least 80%, at least 90%, at least 95%, at least 98%, at least 99%, or 100% identical to IRDR-R-Seq1 (SEQ ID NO: 4). In other cases, a right inverted repeat can comprise a sequence at least 40%, at least 50%, at least 60%, at least 70%, at least 80%, at least 90%, at least 95%, at least 98%, at least 99%, or 100% identical to IRDR-L-Seq1 (SEQ ID NO: 3). Sometimes, a left inverted repeat can comprise a sequence at least 40%, at least 50%, at least 60%, at least 70%, at least 80%, at least 90%, at least 95%, at least 98%, at least 99%, or 100% identical to IRDR-R-Seq1 (SEQ ID NO: 4). The terms "left" and "right", as used herein, can refer to the 5' and 3' sides of the cargo cassette on the sense strand of the double strand transposon, respectively. It is also possible that a transposon may contain a cargo cassette flanked by IRDR-L-Seq2 (SEQ ID NO: 5) and IRDR-R-Seq2 (SEQ ID NO: 6). In many cases, a left inverted repeat can comprise a sequence at least 40%, at least 50%, at least 60%, at least 70%, at least 80%, at least 90%, at least 95%, at least 98%, at least 99%, or 100% identical to IRDR-L-Seq2 (SEQ ID NO: 5). Sometimes, a right inverted repeat can comprise a sequence at least 40%, at least 50%, at least 60%, at least 70%, at least 80%, at least 90%, at least 95%, at least 98%, at least 99%, or 100% identical to IRDR-R-Seq2 (SEQ ID NO: 6). In other cases, a right inverted repeat can comprise a sequence at least 40%, at least 50%, at least 60%, at least 70%, at least 80%, at least 90%, at least 95%, at least 98%, at least 99%, or 100% identical to IRDR-L-Seq2 (SEQ ID NO: 5). Sometimes a left inverted repeat can comprise a sequence at least 40%, at least 50%, at least 60%, at least 70%, at least 80%, at least 90%, at least 95%, at least 98%, at least 99%, or 100% identical to IRDR-R-Seq2 (SEQ ID NO: 6). Alternatively, a transposon can contain a cargo cassette flanked by IRDR-L-Seq3 (SEQ ID NO: 205) and IRDR-R-Seq3 (SEQ ID NO: 206). In many cases, a left inverted repeat can comprise a sequence at least 40%, at least 50%, at least 60%, at least 70%, at least 80%, at least 90%, at least 95%, at least 98%, at least 99%, or 100% identical to IRDR-L-Seq3 (SEQ ID NO: 205). Sometimes, a right inverted repeat can comprise a sequence at least 40%, at least 50%, at least 60%, at least 70%, at least 80%, at least 90%, at least 95%, at least 98%, at least 99%, or 100% identical to IRDR-R-Seq3 (SEQ ID NO: 206). In other cases, a right inverted repeat can comprise a sequence at least 40%, at least 50%, at least 60%, at least 70%, at least 80%, at least 90%, at least 95%, at least 98%, at least 99%, or 100% identical to IRDR-L-Seq3 (SEQ ID NO: 205). Sometimes a left inverted repeat can comprise a sequence at least 40%, at least 50%, at least 60%, at least 70%, at least 80%, at least 90%, at least 95%, at least 98%, at least 99%, or 100% identical to IRDR-R-Seq3 (SEQ ID NO: 206). A transposon may contain a cargo cassette flanked by two inverted repeats that have different nucleotide sequences than the ones given in FIG. 2, or a combination of the various sequences known to one skilled in the art. At least one of the two inverted repeats of a transposon described herein may contain a sequence that is at least 40%, at least 50%, at least 60%, at least 70%, at least 80%, at least 90%, at least 95%, at least 98%, at least 99%, or 100% identical to any one of SEQ ID NOs: 3-6. At least one of inverted repeats of a transposon described herein may contain a sequence that is at least 80% identical to SEQ ID NO: 3 or 4. At least one of inverted repeats of a transposon described herein may contain a sequence that is at least 80% identical to SEQ ID NO: 5 or 6. The choice of inverted repeat sequences may vary depending on the expected transposition efficiency, the type of cell to be modified, the transposase to use, and many other factors.

In many implementations, minimally sized transposon vector inverted terminal repeats that conserve genomic space may be used. The ITRs of hAT family transposons diverge greatly with differences in right-hand and left-hand ITRs. In many cases, smaller ITRs consisting of just 100-200 nucleotides are as active as the longer native ITRs in hAT transposon vectors. These sequences may be consistently reduced while mediating hAT family transposition. These shorter ITRs can conserve genomic space within hAT transposon vectors.

The inverted repeats of a transposon provided herein can be about 50 to 2000 nucleotides, about 50 to 1000 nucleotides, about 50 to 800 nucleotides, about 50 to 600 nucleotides, about 50 to 500 nucleotides, about 50 to 400 nucleotides, about 50 to 350 nucleotides, about 50 to 300 nucleotides, about 50 to 250 nucleotides, about 50 to 200 nucleotides, about 50 to 180 nucleotides, about 50 to 160 nucleotides, about 50 to 140 nucleotides, about 50 to 120 nucleotides, about 50 to 110 nucleotides, about 50 to 100 nucleotides, about 50 to 90 nucleotides, about 50 to 80 nucleotides, about 50 to 70 nucleotides, about 50 to 60 nucleotides, about 75 to 750 nucleotides, about 75 to 450 nucleotides, about 75 to 325 nucleotides, about 75 to 250 nucleotides, about 75 to 150 nucleotides, about 75 to 95 nucleotides, about 100 to 500 nucleotides, about 100 to 400 nucleotides, about 100 to 350 nucleotides, about 100 to 300 nucleotides, about 100 to 250 nucleotides, about 100 to 220 nucleotides, about 100 to 200 nucleotides, or in any range derived therefrom.

In some cases, a cargo cassette can comprise a promoter, a transgene, or a combination thereof. In cargo cassettes comprising both a promoter and a transgene, the expression of the transgene can be directed by the promoter. A promoter can be any type of promoter available to one skilled in the art. Non-limiting examples of the promoters that can be used in a TcBuster transposon include EFS, CMV, MND, EF1α, CAGGs, PGK, UBC, U6, H1, and Cumate. The choice of a promoter to be used in a TcBuster transposition would depend on a number of factors, such as, but not limited to, the expression efficiency of the promoter, the type of cell to be genetically modified, and the desired transgene expression level.

A transgene in a TcBuster transposon can be any gene of interest and available to one skilled in the art. A transgene can be derived from, or a variant of, a gene in nature, or can be artificially designed. A transgene can be of the same species origin as the cell to be modified, or from different species. A transgene can be a prokaryotic gene, or a eukaryotic gene. Sometimes, a transgene can be a gene derived from a non-human animal, a plant, or a human being. A transgene can comprise introns. Alternatively, a transgene may have introns removed or not present.

In some embodiments, a transgene can code for a protein. Exemplary proteins include, but are not limited to, a cellular receptor, an immunological checkpoint protein, a cytokine, or any combination thereof. Sometimes, a cellular receptor as described herein can include, but not limited to a T cell receptor (TCR), a B cell receptor (BCR), a chimeric antigen receptor (CAR), or any combination thereof.

A cargo cassette as described herein may not contain a transgene coding for any type of protein product, but that is useful for other purposes. For instance, a cargo cassette may be used for creating frameshift in the insertion site, for example, when it is inserted in an exon of a gene in the host genome. This may lead to a truncation of the gene product or a null mutation. Sometimes, a cargo cassette may be used for replacing an endogenous genomic sequence with an exogenous nucleotide sequence, thereby modifying the host genome.

A transposon described herein may have a cargo cassette in either forward or reverse direction. In many cases, a cargo cassette has its own directionality. For instance, a cargo cassette containing a transgene would have a 5' to 3' coding sequence. A cargo cassette containing a promoter and a gene insertion would have promoter on the 5' site of the gene insertion. The term "forward direction", as used herein, can refer to the situation where a cargo cassette maintains its directionality on the sense strand of the double strand transposon. The term "reverse direction", as used herein, can refer to the situation where a cargo cassette maintains its directionality on the antisense strand of the double strand transposon.

Systems for Genome Editing and Methods of Use

Another aspect of the present disclosure provides a system for genome editing. A system can comprise a TcBuster transposase and a TcBuster transposon. A system can be used to edit a genome of a host cell, disrupting or modifying an endogenous genomic region of the host cell, inserting an exogenous gene into the host genome, replacing an endogenous nucleotide sequence with an exogenous nucleotide sequence or any combination thereof.

A system for genome editing can comprise a mutant TcBuster transposase or fusion transposase as described herein, and a transposon recognizable by the mutant TcBuster transposase or the fusion transposase. A mutant TcBuster transposase or the fusion transposase can be provided as a purified protein. Protein production and purification technologies are known to one skilled in the art. The purified protein can be kept in a different container than the transposon, or they can be kept in the same container.

In many cases, a system for genome editing can comprise a polynucleotide encoding a mutant TcBuster transposase or fusion transposase as described herein, and a transposon recognizable by the mutant TcBuster transposase or the fusion transposase. Sometimes, a polynucleotide of the system can comprise DNA that encodes the mutant TcBuster transposase or the fusion transposase. Alternatively or additionally, a polynucleotide of the system can comprise messenger RNA (mRNA) that encodes the mutant TcBuster transposase or the fusion transposase. The mRNA can be produced by a number of approaches well known to one of ordinary skills in the art, such as, but not limited to, in vivo transcription and RNA purification, in vitro transcription, and de novo synthesis. In many cases, the mRNA can be chemically modified. The chemically modified mRNA may be resistant to degradation than unmodified or natural mRNAs or may degrade more quickly. In many cases, the chemical modification of the mRNA may render the mRNA being translated with more efficiency. Chemical modification of mRNAs can be performed with well-known technologies available to one skilled in the art, or by commercial vendors.

For many applications, safety dictates that the duration of hAT transposase expression be only long enough to mediate safe transposon delivery. Moreover, a pulse of hAT transposase expression that coincides with the height of transposon vector levels can achieve maximal gene delivery. The implementations are made using available technologies for the in vitro transcription of RNA molecules from DNA plasmid templates. The RNA molecules can be synthesized using a variety of methods for in vitro (e.g., cell free) transcription from a DNA copy. Methods to do this have been described and are commercially available. For example, the mMessage Machine in vitro transcription kit available through life technologies.

There are also a number of companies that can perform in vitro transcription on a fee for service basis. We have also found that that chemically modified RNAs for hAT expression work especially well for gene transfer. These chemically modified RNAs do not induce cellular immune responses and RNA generated using proprietary methods that also avoid the cellular immune response. These RNA preparations remove RNA dimers (Clean-Cap) and cellular reactivity (pseudouridine incorporation) produce better transient gene expression in human T cells without toxicity in our hands (data not shown). The RNA molecules can be introduced into cells using any of many described methods for RNA transfection, which is usually non-toxic to most cells. Methods to do this have been described and are commercially available. For example, the Amaxa nucleofector, Neon electroporator, and the Maxcyte platforms.

A transposon as described herein may be present in an expression vector. In many cases, the expression vector can be DNA plasmid. Sometimes, the expression vector can be a mini-circle vector. The term "mini-circle vector" as used herein can refer to small circular plasmid derivative that is free of most, if not all, prokaryotic vector parts (e.g., control sequences or non-functional sequences of prokaryotic origin). Under circumstances, the toxicity to the cells created by transfection or electroporation can be mitigated by using the "mini-circles" as described herein.

A mini-circle vector can be prepared by well-known molecular cloning technologies available. First, a 'parental plasmid' (bacterial plasmid with insertion, such as transposon construct) in bacterial, such as *E. coli*, can be produced, which can be followed by induction of a site-specific recombinase. These steps can then be followed by the excision of prokaryotic vector parts via two recombinase-target sequences at both ends of the insert, as well as recovery of the resulting mini-circle vector. The purified mini-circle can be transferred into the recipient cell by transfection or lipofection and into a differentiated tissue by, for instance, jet injection. A mini-circle containing TcBuster transposon can have a size about 1.5 kb, about 2 kb, about 2.2 kb, about 2.4 kb, about 2.6 kb, about 2.8 kb, about 3 kb, about 3.2 kb, about 3.4 kb, about 3.6 kb, about 3.8 kb, about 4 kb, about 4.2 kb, about 4.4 kb, about 4.6 kb, about 4.8 kb, about 5 kb, about 5.2 kb, about 5.4 kb, about 5.6 kb, about 5.8 kb, about 6 kb, about 6.5 kb, about 7 kb, about 8 kb, about 9 kb, about 10 kb, about 12 kb, about 25 kb, about 50 kb, or a value between any two of these numbers. Sometimes, a mini-circle containing TcBuster transposon as provided herein can have a size at most 2.1 kb, at most 3.1 kb, at most 4.1 kb, at most 4.5 kb, at most 5.1 kb, at most 5.5 kb, at most 6.5 kb, at most 7.5 kb, at most 8.5 kb, at most 9.5 kb, at most 11 kb, at most 13 kb, at most 15 kb, at most 30 kb, or at most 60 kb.

In certain embodiments, a system as described herein may contain a polynucleotide encoding a mutant TcBuster transposase or fusion transposase as described herein, and a transposon, which are present in a same expression vector, e.g. plasmid.

Yet another aspect of the present disclosure provides a method of genetic engineering. A method of genetic engineering can comprise introducing into a cell a TcBuster transposase and a transposon recognizable by the TcBuster transposase. A method of genetic engineering can also be performed in a cell-free environment. A method of genetic engineering in a cell-free environment can comprise combining a TcBuster transposase, a transposon recognizable by the transposase, and a target nucleic acid into a container, such as a well or tube.

A method described herein can comprises introducing into a cell a mutant TcBuster transposase provided herein and a transposon recognizable by the mutant TcBuster transposase. A method of genome editing can comprise: introducing into a cell a fusion transposase provided herein and a transposon recognizable by the fusion transposase.

The mutant TcBuster transposase or the fusion transposase can be introduced into the cell either as a protein or via a polynucleotide that encodes for the mutant TcBuster transposase or the fusion transposase. The polynucleotide, as discussed above, can comprise a DNA or an mRNA that encodes the mutant TcBuster transposase or the fusion transposase.

In many instances, the TcBuster transposase or the fusion transposase can be transfected into a host cell as a protein, and the concentration of the protein can be at least 0.05 nM, at least 0.1 nM, at least 0.2 nM, at least 0.5 nM, at least 1 nM, at least 2 nM, at least 5 nM, at least 10 nM, at least 50 nM, at least 100 nM, at least 200 nM, at least 500 nM, at least 1 μM, at least 2 μM, at least 5 μM, at least 7.5 μM, at least 10 μM, at least 15 μM, at least 20 μM, at least 25 μM, at least 50 μM, at least 100 μM, at least 200 μM, at least 500 μM, or at least 1 μM. Sometimes, the concentration of the protein can be around 1 μM to around 50 μM, around 2 μM to around 25 μM, around 5 μM to around 12.5 μM, or around 7.5 μM to around 10 μM.

In many cases, the TcBuster transposase or the fusion transposase can be transfected into a host cell through a polynucleotide, and the concentration of the polynucleotide can be at least about 5 ng/ml, 10 ng/ml, 20 ng/ml, 40 ng/ml, 50 ng/ml, 60 ng/ml, 80 ng/ml, 100 ng/ml, 120 ng/ml, 150 ng/ml, 180 ng/ml, 200 ng/ml, 220 ng/ml, 250 ng/ml, 280 ng/ml, 300 ng/ml, 500 ng/ml, 750 ng/ml, 1 μg/ml, 2 μg/ml, 3 μg/ml, 5 μg/ml, 50 μg/ml, 100 μg/ml, 150 μg/ml, 200 μg/ml, 250 μg/ml, 300 μg/ml, 350 μg/ml, 400 μg/ml, 450 μg/ml, 500 μg/ml, 550 μg/ml, 600 μg/ml, 650 μg/ml, 700 μg/ml, 750 μg/ml, or 800 μg/ml. Sometimes, the concentration of the polynucleotide can be between about 5-25 μg/ml, 25-50 μg/ml, 50-100 μg/ml, 100-150 μg/ml, 150-200 μg/ml, 200-250 μg/ml, 250-500 μg/ml, 5-800 μg/ml, 200-800 μg/ml, 250-800 μg/ml, 400-800 μg/ml, 500-800 μg/ml, or any range derivable therein. In many cases, the transposon is present in a separate expression vector than the transposase, and the concentration of the transposon can be at least about 5 ng/ml, 10 ng/ml, 20 ng/ml, 40 ng/ml, 50 ng/ml, 60 ng/ml, 80 ng/ml, 100 ng/ml, 120 ng/ml, 150 ng/ml, 180 ng/ml, 200 ng/ml, 220 ng/ml, 250 ng/ml, 280 ng/ml, 300 ng/ml, 500 ng/ml, 750 ng/ml, 1 μg/ml, 2 μg/ml, 3 μg/ml, 5 μg/ml, 50 μg/ml, 100 μg/ml, 150 μg/ml, 200 μg/ml, 250 μg/ml, 300 μg/ml, 350 μg/ml, 400 μg/ml, 450 μg/ml, 500 μg/ml, 550 μg/ml, 600 μg/ml, 650 μg/ml, 700 μg/ml, 750 μg/ml, or 800 μg/ml. Sometimes, the concentration of the transposon can be between about 5-25 μg/ml, 25-50 μg/ml, 50-100 μg/ml, 100-150 μg/ml, 150-200 μg/ml, 200-250 μg/ml, 250-500 μg/ml, 5-800 μg/ml, 200-800 μg/ml, 250-800 μg/ml, 400-800 μg/ml, 500-800 μg/ml, or any range derivable therein. It is possible the ratio of the transposon versus the polynucleotide coding for the transposase is at most 10000, at most 5000, at most 1000, at most 500, at most 200, at most 100, at most 50, at most 20, at most 10, at most 5, at most 2, at most 1, at most 0.1, at most 0.05, at most 0.01, at most 0.001, at most 0.0001, or any number in between any two thereof.

In some other cases, the transposon and the polynucleotide coding for the transposase are present in the same expression vector, and the concentration of the expression vector containing both transposon and the polynucleotide encoding transposase can be at least about 5 ng/ml, 10 ng/ml, 20 ng/ml, 40 ng/ml, 50 ng/ml, 60 ng/ml, 80 ng/ml, 100 ng/ml, 120 ng/ml, 150 ng/ml, 180 ng/ml, 200 ng/ml, 220 ng/ml, 250 ng/ml, 280 ng/ml, 300 ng/ml, 500 ng/ml, 750 ng/ml, 1 μg/ml, 2 μg/ml, 3 μg/ml, 5 μg/ml, 50 μg/ml, 100 μg/ml, 150 μg/ml, 200 μg/ml, 250 μg/ml, 300 μg/ml, 350 μg/ml, 400 μg/ml, 450 μg/ml, 500 μg/ml, 550 μg/ml, 600 μg/ml, 650 μg/ml, 700 μg/ml, 750 μg/ml, or 800 μg/ml. Sometimes, the concentration of the expression vector containing both transposon and the polynucleotide encoding transposase can be between about 5-25 μg/ml, 25-50 μg/ml, 50-100 μg/ml, 100-150 μg/ml, 150-200 μg/ml, 200-250 μg/ml, 250-500 μg/ml, 5-800 μg/ml, 200-800 μg/ml, 250-800 μg/ml, 400-800 μg/ml, 500-800 μg/ml, or any range derivable therein.

In some cases, the amount of polynucleic acids that may be introduced into the cell by electroporation may be varied to optimize transfection efficiency and/or cell viability. In some cases, less than about 100 pg of nucleic acid may be added to each cell sample (e.g., one or more cells being electroporated). In some cases, at least about 100 pg, at least about 200 pg, at least about 300 pg, at least about 400 pg, at least about 500 pg, at least about 600 pg, at least about 700 pg, at least about 800 pg, at least about 900 pg, at least about 1 microgram, at least about 1.5 μg, at least about 2 μg, at least about 2.5 μg, at least about 3 μg, at least about 3.5 μg, at least about 4 μg, at least about 4.5 μg, at least about 5 μg, at least about 5.5 μg, at least about 6 μg, at least about 6.5 μg, at least about 7 μg, at least about 7.5 μg, at least about 8 μg, at least about 8.5 μg, at least about 9 μg, at least about 9.5 μg, at least about 10 μg, at least about 11 μg, at least about 12 μg, at least about 13 μg, at least about 14 μg, at least about 15 μg, at least about 20 μg, at least about 25 μg, at least about 30 μg, at least about 35 μg, at least about 40 μg, at least about 45 μg, or at least about 50 μg, of nucleic acid may be added to each cell sample (e.g., one or more cells being electroporated). For example, 1 microgram of dsDNA may be added to each cell sample for electroporation. In some cases, the amount of polynucleic acids (e.g., dsDNA) required for optimal transfection efficiency and/or cell viability may be specific to the cell type.

The subject matter disclosed herein may find use in genome editing of a wide range of various types of host cells. In preferred embodiments, the host cells may be from eukaryotic organisms. In some embodiments, the cells may be from a mammal origin. In some embodiments, the cells may be from a human origin.

In general, the cells may be from an immortalized cell line or primary cells.

The terms "cell line" and "immortalized cell line", as used herein interchangeably, can refer to a population of cells from an organism which would normally not proliferate indefinitely but, due to mutation, may have evaded normal cellular senescence and instead can keep undergoing division. The subject matter provided herein may find use in a range of common established cell lines, including, but not limited to, human BC-1 cells, human BJAB cells, human IM-9 cells, human Jiyoye cells, human K-562 cells, human LCL cells, mouse MPC-11 cells, human Raji cells, human Ramos cells, mouse Ramos cells, human RPMI8226 cells, human RS4-11 cells, human SKW6.4 cells, human Dendritic cells, mouse P815 cells, mouse RBL-2H3 cells, human HL-60 cells, human NAMALWA cells, human Macrophage cells, mouse RAW 264.7 cells, human KG-1 cells, mouse M1 cells, human PBMC cells, mouse BW5147 (T200-A)5.2 cells, human CCRF-CEM cells, mouse EL4 cells, human Jurkat cells, human SCID.adh cells, human U-937 cells or any combination of cells thereof.

The term "primary cells" and its grammatical equivalents, as used herein, can refer to cells taken directly from an organism, typically living tissue of a multicellular organism, such as animals or plants. In many cases, primary cells may be established for growth in vitro. In some cases, primary cells may be just removed from the organism and have not been established for growth in vitro yet before the transfection. In some embodiments, the primary cells can also be expanded in vitro, i.e. primary cells may also include progeny cells that are generated from proliferation of the cells taken directly from an organism. In these cases, the progeny cells do not exhibit the indefinite proliferative property as cells in established cell lines. For instance, the host cells may be human primary T cells, while prior to the transfection, the T cells have been exposed to stimulatory factor(s) that may result in T cell proliferation and expansion of the cell population.

The cells to be genetically modified may be primary cells from tissues or organs, such as, but not limited to, brain, lung, liver, heart, spleen, pancreas, small intestine, large intestine, skeletal muscle, smooth muscle, skin, bones, adipose tissues, hairs, thyroid, trachea, gall bladder, kidney, ureter, bladder, aorta, vein, esophagus, diaphragm, stomach, rectum, adrenal glands, bronchi, ears, eyes, retina, genitals, hypothalamus, larynx, nose, tongue, spinal cord, or ureters, uterus, ovary, testis, and any combination thereof. In certain embodiments, the cells may include, but not limited to, hematocyte, trichocyte, keratinocyte, gonadotrope, corticotrope, thyrotrope, somatotrope, lactotroph, chromaffin cell, parafollicular cell, *glomus* cell, melanocyte, nevus cell, merkel cell, odontoblast, cementoblast, corneal keratocyte, retina muller cell, retinal pigment epithelium cell, neuron, glia, ependymocyte, pinealocyte, pneumocyte, clara cell, goblet cell, G cell, D cell, Enterochromaffin-like cell, gastric chief cell, parietal cell, foveolar cell, K cell, D cell, I cell, paneth cell, enterocyte, microfold cell, hepatocyte, hepatic stellate cell, cholecystocyte, centroacinar cell, pancreatic stellate cell, pancreatic α cell, pancreatic β cell, pancreatic δ cell, pancreatic F cell, pancreatic c cell, thyroid parathyroid, oxyphil cell, urothelial cell, osteoblast, osteocyte, chondroblast, chondrocyte, fibroblast, fibrocyte, myoblast, myocyte, myosatellite cell, tendon cell, cardiac muscle cell, lipoblast, adipocyte, interstitial cell of cajal, angioblast, endothelial cell, mesangial cell, juxtaglomerular cell, macula *densa* cell, stromal cell, interstitial cell, telocyte, simple epithelial cell, podocyte, kidney proximal tubule brush border cell, sertoli cell, leydig cell, granulosa cell, peg cell, germ cell, spermatozoon ovum, lymphocyte, myeloid cell, endothelial progenitor cell, endothelial stem cell, angioblast, mesoangioblast, pericyte mural cell, and any combination thereof. In many instances, the cell to be modified may be a stem cell, such as, but not limited to, embryonic stem cell, hematopoietic stem cell, epidermal stem cell, epithelial stem cell, bronchoalveolar stem cell, mammary stem cell, mesenchymal stem cell, intestine stem cell, endothelial stem cell, neural stem cell, olfactory adult stem cell, neural crest stem cell, testicular cell, and any combination thereof. Sometimes, the cell can be an induced pluripotent stem cell that is derived from any type of tissue.

In some embodiments, the cell to be genetically modified may be a mammalian cell. In some embodiments, the cell may be an immune cell. Non-limiting examples of the cell can include a B cell, a basophil, a dendritic cell, an eosinophil, a gamma delta T cell, a granulocyte, a helper T cell, a Langerhans cell, a lymphoid cell, an innate lymphoid cell (ILC), a macrophage, a mast cell, a megakaryocyte, a memory T cell, a monocyte, a myeloid cell, a natural killer T cell, a neutrophil, a precursor cell, a plasma cell, a progenitor cell, a regulatory T-cell, a T cell, a thymocyte, any differentiated or de-differentiated cell thereof, or any mixture or combination of cells thereof. In certain cases, the cell may be a T cell. In some embodiments, the cell may be a primary T cell. In certain cases, the cell may be an antigen-presenting cell (APC). In some embodiments, the cell may be a primary APC. The APCs in connection with the present disclosure may be a dendritic cell, macrophage, B cell, other non-professional APCs, or any combination thereof.

In some embodiments, the cell may be an ILC (innate lymphoid cell), and the ILC can be a group 1 ILC, a group 2 ILC, or a group 3 ILC. Group 1 ILCs may generally be described as cells controlled by the T-bet transcription factor, secreting type-1 cytokines such as IFN-gamma and TNF-alpha in response to intracellular pathogens. Group 2 ILCs may generally be described as cells relying on the GATA-3 and ROR-alpha transcription factors, producing type-2 cytokines in response to extracellular parasite infections. Group 3 ILCs may generally be described as cells controlled by the ROR-gamma t transcription factor, and produce IL-17 and/or IL-22.

In some embodiments, the cell may be a cell that is positive or negative for a given factor. In some embodiments, a cell may be a CD3+ cell, CD3− cell, a CD5+ cell, CD5− cell, a CD7+ cell, CD7− cell, a CD14+ cell, CD14− cell, CD8+ cell, a CD8− cell, a CD103+ cell, CD103− cell, CD11b+ cell, CD11b− cell, a BDCA1+ cell, a BDCA1− cell, an L-selectin+ cell, an L-selectin-cell, a CD25+, a CD25− cell, a CD27+, a CD27− cell, a CD28+ cell, CD28− cell, a CD44+ cell, a CD44− cell, a CD56+ cell, a CD56− cell, a CD57+ cell, a CD57− cell, a CD62L+ cell, a CD62L-cell, a CD69+ cell, a CD69− cell, a CD45RO+ cell, a CD45RO-cell, a CD127+ cell, a CD127− cell, a CD132+ cell, a CD132− cell, an IL-7+ cell, an IL-7− cell, an IL-15+ cell, an IL-15− cell, a lectin-like receptor G1positive cell, a lectin-like receptor G1 negative cell, or an differentiated or de-differentiated cell thereof. The examples of factors expressed by cells is not intended to be limiting, and a person having skill in the art will appreciate that the cell may be positive or negative for any factor known in the art. In some embodiments, the cell may be positive for two or more factors. For example, the cell may be CD4+ and CD8+. In some embodiments, the cell may be negative for two or more factors. For example, the cell may be CD25−, CD44−, and CD69−. In some embodiments, the cell may be positive for one or more factors, and negative for one or more factors. For example, a cell may be CD4+ and CD8−.

It should be understood that cells used in any of the methods disclosed herein may be a mixture (e.g., two or more different cells) of any of the cells disclosed herein. For example, a method of the present disclosure may comprise cells, and the cells are a mixture of CD4+ cells and CD8+ cells. In another example, a method of the present disclosure may comprise cells, and the cells are a mixture of CD4+ cells and naïve cells.

As provided herein, the transposase and the transposon can be introduced in to a cell through a number of approaches. The term “transfection” and its grammatical equivalents as used herein can generally refer to a process whereby nucleic acids are introduced into eukaryotic cells. The transfection methods that can be used in connection with the subject matter can include, but not limited to, electroporation, microinjection, calcium phosphate precipitation, cationic polymers, dendrimers, liposome, microprojectile bombardment, fugene, direct sonic loading, cell squeezing, optical transfection, protoplast fusion, impalefection, magnetofection, nucleofection, or any combination thereof. In many cases, the transposase and transposon described herein can be transfected into a host cell through electroporation. Sometimes, transfection can also be done through a variant of electroporation method, such as nucleofection (also known as Nucleofector™ technology). The term “electroporation” and its grammatical equivalents as used herein can refer to a process whereby an electrical field is applied to cells in order to increase the permeability of the cell membrane, allowing chemicals, drugs, or DNA to be introduced into the cell. During electroporation, the electric filed is often provided in the form of “pulses” of very brief time periods, e.g. 5 milliseconds, 10 milliseconds, and 50 milliseconds. As understood by those skilled in the art, electroporation temporarily opens up pores in a cell’s outer membrane by use of pulsed rotating electric fields. Methods and apparatus used for electroporation in vitro and in vivo are also well known. Various electric parameters can be selected dependent on the cell type being electroporated and physical characteristics of the molecules that are to be taken up by the cell, such as pulse intensity, pulse length, number of pulses).

Applications

The subject matter, e.g., the compositions (e.g., mutant TcBuster transposases, fusion transposases, TcBuster transposons), systems and methods, provided herein may find use in a wide range of applications relating to genome editing, in various aspects of modern life.

Under certain circumstances, advantages of the subject matter described herein may include, but not limited to, reduced costs, regulatory consideration, lower immunogenicity and less complexity. In some cases, a significant advantage of the present disclosure is the high transposition efficiency. Another advantage of the present disclosure, in many cases, is that the transposition system provided herein can be “tunable”, e.g., transposition can be designed to target select genomic region rather than random insertion.

One non-limiting example is related to create genetically modified cells for research and clinical applications. For example, as discussed above, genetically modified T cells can be created using the subject matter provided herein, which may find use in helping people fighting against a variety of diseases, such as, but not limited to, cancer and infectious disease.

One particular example includes generation of genetically modified primary leukocytes using the methods provided herein, and administering the genetically modified primary leukocytes to a patient in need thereof. The generation of genetically modified primary leukocytes can include introducing into a leukocyte a transposon and a mutant TcBuster transposase or the fusion transposase as described herein, which can recognize the transposon, thereby generating a genetically modified leukocyte. In many cases, the transposon may comprise a transgene. The transgene can be a cellular receptor, an immunological checkpoint protein, a cytokine, and any combination thereof. Sometimes, a cellular receptor can include, but not limited to a T cell receptor (TCR), a B cell receptor (BCR), a chimeric antigen receptor (CAR), or any combination thereof. In some other cases, the transposon and the transposase are designed to delete or modify an endogenous gene, for instance, a cytokine, an immunological checkpoint protein, an oncogene, or any combination thereof. The genetic modification of the primary leukocytes can be designed to facilitate immunity against an infectious pathogen or cancer cells that render the patient in diseased state.

Another non-limiting example is related to create genetically modified organisms for agriculture, food production, medicine, and pharmaceutics. The species that can be genetically modified span a wide range, including, but not limited to, plants and animals. The genetically modified organisms, such as genetically modified crops or livestock, may be modified in a certain aspect of their physiological properties. Examples in food crops include resistance to certain pests, diseases, or environmental conditions, reduction of spoilage, or resistance to chemical treatments (e.g. resistance to a herbicide), or improving the nutrient profile of the crop. Examples in non-food crops include production of pharmaceutical agents, biofuels, and other industrially useful goods, as well as for bioremediation. Examples in livestock include resistance to certain parasites, production of certain nutrition elements, increase in growth rate, and increase in milk production.

The term "about" and its grammatical equivalents in relation to a reference numerical value and its grammatical equivalents as used herein can include a range of values plus or minus 10% from that value. For example, the amount "about 10" includes amounts from 9 to 11. The term "about" in relation to a reference numerical value can also include a range of values plus or minus 10%, 9%, 8%, 7%, 6%, 5%, 4%, 3%, 2%, or 1% from that value.

EXAMPLES

The examples below further illustrate the described embodiments without limiting the scope of this disclosure.

Example 1. Materials and Methods

This example describes several methods utilized for generation and evaluation of exemplary mutant TcBuster transposases.

Site Directed Mutagenesis for TcBuster Mutant Preparation

Putative hyperactive TcBuster (TcB) transposase mutants were identified by nucleotide sequence and amino acid alignment of hAT and buster subfamilies. The Q5 site-directed mutagenesis kit (New England BioLabs) was used for all site-directed mutagenesis. Following PCR mutagenesis, PCR products were purified with GeneJET PCR purification kit (Thermo Fisher Scientific). A 20 uL ligation reaction of purified PCR products was performed using T4 DNA ligase (New England BioLabs). 5 uL of ligation reaction was used for transformation in DH10Beta cells. Direct colony sequencing through Sequetech was used to confirm the presence of desired mutations. DNA for confirmed mutations was prepped using ZymoPURE plasmid miniprep kits (Zymo Research).

Measuring Transection Efficiency in HEK-293T Cells

HEK-293T cells were plated at 300,000 cells per well of a 6 well plate one day prior to transfection. Cells were transfected with 500 ng transposon carrying mCherry-puromycin cassette and 62.5 ng TcB transposase using TransIT X2 reagent per manufacturer's instructions (Mirus Bio). Two days post-transfection, cells were re-plated with puromycin (1 ug/mL) at a density of 3,000 cells/well of a 6 well plate in triplicate in DMEM complete media, or re-plated without puromycin selection. Stable integration of the transgene was assessed by colony counting of puromycin treated cells (each cell that survived drug selection formed a colony) or flow cytometry. For colony counting, two weeks post-puromycin selection, DMEM complete+puromycin media was removed. Cells were washed with 1×PBS and cells were stained with 1× crystal violet solution for 10 minutes. Plates were washed twice with PBS and colonies counted.

For flow cytometry analysis, stable integration of the transgene was assessed by detection of mCherry fluorescence in cells grown without drug selection. Transfected cells were harvested at indicated time points post-transfection, washed 1× with PBS and resuspended in 200 uL RDFII buffer for analysis. Cells were analyzed using Novocyte (Acea Biosciences) and mCherry expression was assessed using the PE-Texas red channel.

Screening of TcB Transposase Mutants in HEK-293T Cells

HEK-293T cells were plated at 75,000 cells per well of a 24 well plate one day prior to transfection. Cells were transfected with 500 ng transposon and 125 ng transposase using TransIT X2 reagent in duplicate per manufacturer's instructions (Mirus Bio). Stable integration of the transgene was assessed by detection of mCherry fluorescence. Cells were harvested at 14 days post-transfection, washed 1× with PBS and resuspended in 200 uL RDFII buffer. Cells were analyzed using Novocyte (Acea Biosciences) and mCherry expression was assessed using the PE-Texas red channel.

Transfection of TcBuster Transposon and Transposase in CD3+ T-Cells

CD3+ T-Cells were Enriched and Cryopreserved from Leukopaks (StemCellTechnologies). CD3+ T-cells were thawed and activated using CD3/CD28 Dynabeads (ThermoFisher) for 2 days in X-Vivo-15 media supplemented with human serum and IL-2, IL-15 and IL-7 cytokines. Prior to transfection, CD3/CD28 beads were removed, cells washed and electroporated using Neon Transfection system (ThermoFisher) with TcBuster transposon (mini-circle carrying TcBuster and Sleeping beauty IR/DRs and GFP cargo) and TcBuster or Sleeping Beauty transposases in RNA form. As a viability control, cells were "pulse" electroporated without DNA or RNA. Electroporated cells were expanded for 21 days post-transfection and viability stable integration of GFP cargo was assessed by flow cytometry. Viability was measured by SSC-A vs FSC-A and standardized to pulse only control, and GFP expression was assessed using FITC channel on days 2, 7, 14 and 21.

Example 2. Exemplary Transposon Constructs

The aim of this study was to examine transposition efficiency of different exemplary TcBuster transposon constructs. Inventors compared 10 TcBuster (TcB) transposon (Tn) configurations (FIG. 1A) to test their transposition efficiency in mammalian cells. These 10 TcB Tns differed in the promoter used (EFS vs CMV), IR/DR sequence and direction of the transposon cargo. The transposons each contained an identical cassette coding for mCherry linked by 2A to a drug-resistance gene, puromycin, so that transfected cells could be identified by fluorescence and/or selection with puromycin. HEK-293T cells were transfected with one of the 10 TcB Tns and TcB wild-type transposase (ratio of 1 transposon:1 transposase). Stable integration of the transgene was assessed by flow cytometry by detection of mCherry fluorescence for 10-30 days post-transfection (FIG. 1B).

It was found that, under experimental conditions, stable expression of the transgene mCherry was greatly enhanced using the CMV promoter compared to EFS. Transposition appeared to only occur when sequence 1 IR/DRs was used. It was also found that transcription of the cargo in the reverse direction promoted greater transposition activity compared to the forward direction.

Figure 3B:
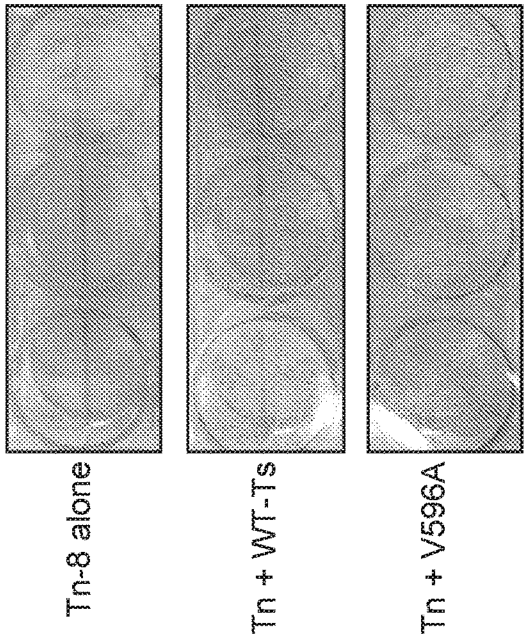
FIG. 3B shows representative pictures of the transfected cell colonies in 6-well plate 2 weeks posttransfection.
Figure 3C:
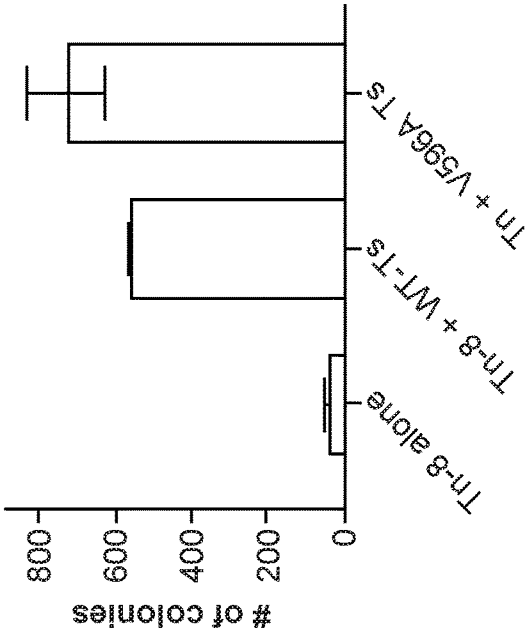
FIG. 3C is a graph showing the quantification of colonies per each transfection condition 2 weeks posttransfection.
Figure 3A:
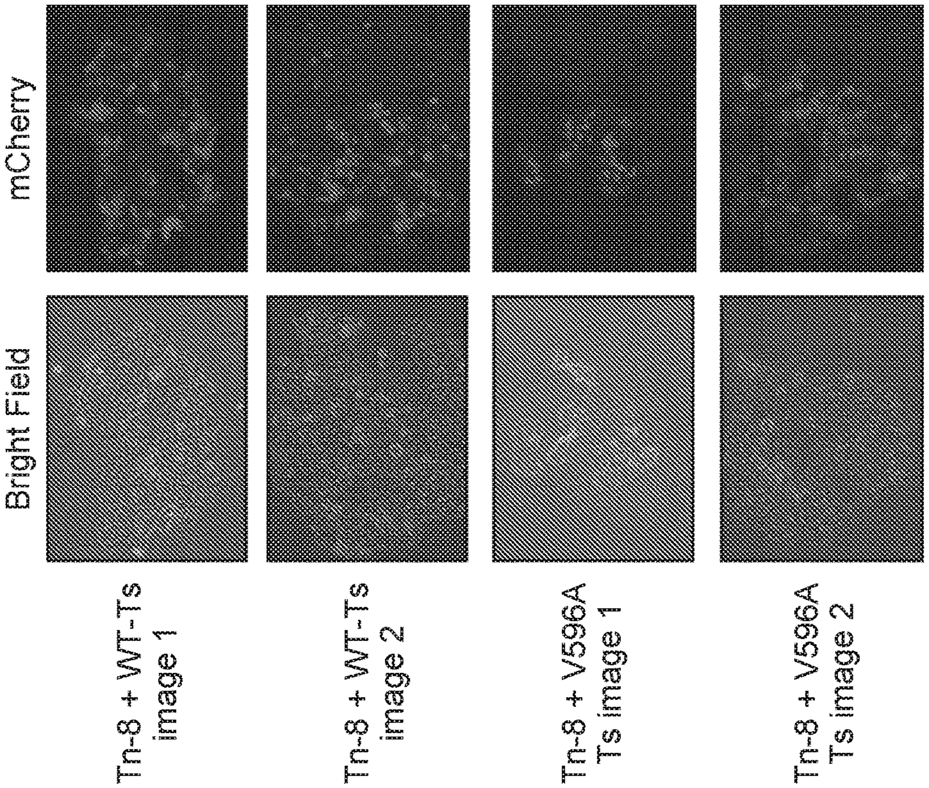
FIG. 3A shows representative bright-field and fluorescent images of HEK-293T cells 2 weeks after transfection with exemplary TcBuster transposon Tn-8 (containing puro-mCherry cassette; illustrated in FIG. 1) and WT TcBuster transposase or V596A mutant transposase (containing V596A substitution). The transfected cells were plated in 6-well plate with 1 μg/mL puromycin 2 days posttransfection, and were fixed and stained 2 weeks posttransfection with crystal violet for colony quantification.

TcB Tn-8 showed the greatest transposition efficiency among the test 10 Tns by flow cytometry. To confirm the transposition efficiency of TcB Tn-8, HEK-293T cells were transfected with TcB Tn-8 with WT transposase or V596A mutant transposase. Two days post-transfection, cells were re-plated with puromycin (1 ug/mL) at a density of 3,000 cells/well of a 6 well plate in triplicate in DMEM complete media. After selection for two weeks, each cell that survived drug selection formed a colony, which was assessed for mCherry expression (FIG. 3A) and counted to confirm stable integration of the transgene (FIGS. 3B-C). Transposition efficiency of TcB-Tn 8 was confirmed by expression of mCherry and puromycin resistant colonies in HEK-293T cells.

Example 3. Exemplary Transposase Mutants

The aim of this study was to generate TcBuster transposase mutants and examine their transposition efficiency.

To this end, inventors have generated a consensus sequence by comparing cDNA and amino acid sequences of wild-type TcB transposase to other similar transposases. For the comparison, sleeping beauty was resurrected by the alignment of 13 similar transposases and SPIN by the alignment of SPIN like transposases from 8 separate organisms. SPIN and TcBuster are a part of the abundant hAT family of transposases.

Figure 5:
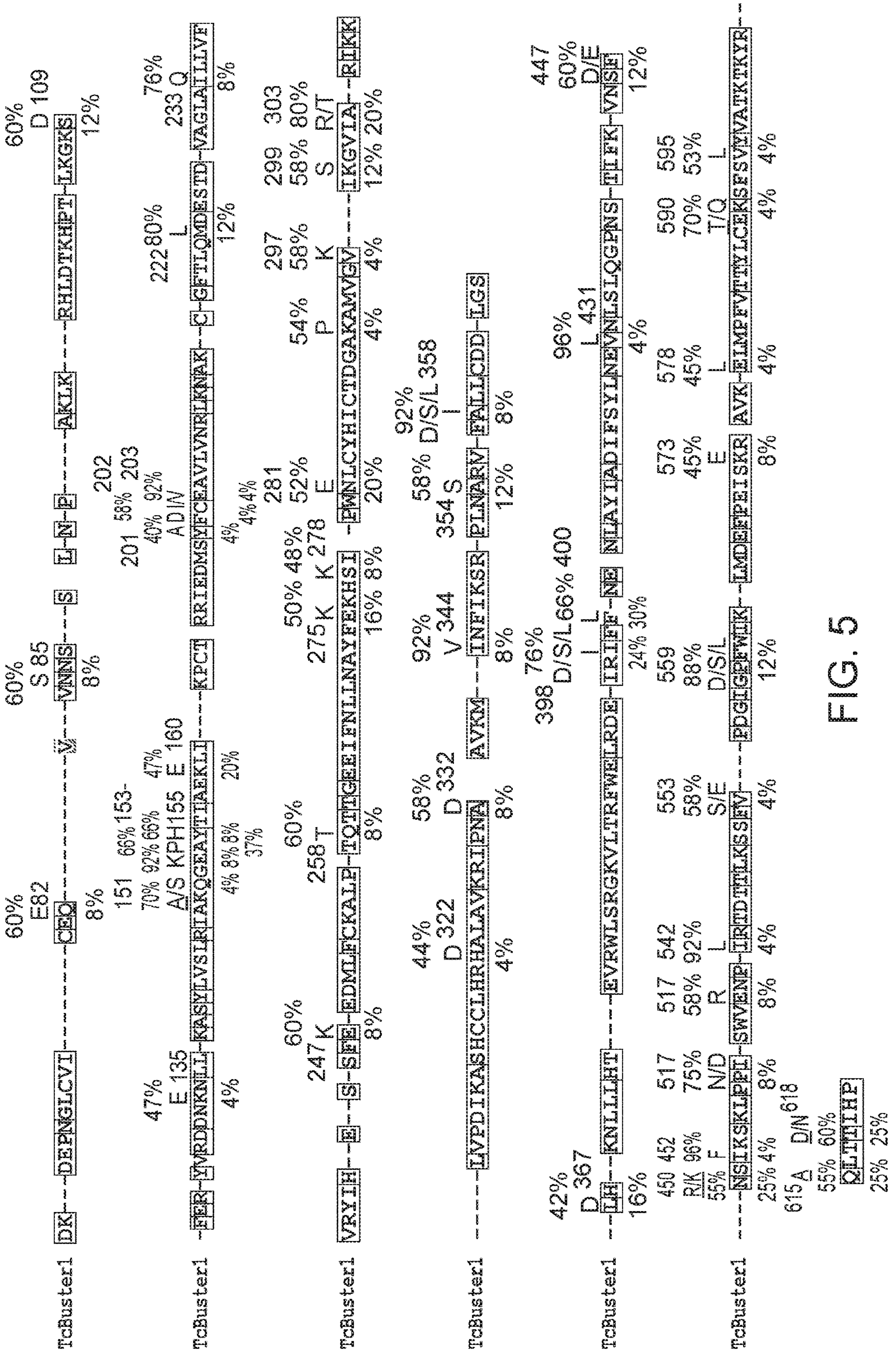
FIG. 5 depicts the amino acid sequence alignment of TcBuster transposase versus a number of other transposase members in Buster subfamily (SEQ ID NOS 195-203, respectively in order of appearance). Certain exemplary amino acid substitutions are indicated above the protein sequences, along with the percentage shown on top of the alignment is the percentage of other Buster subfamily members that contain the amino acid that is contemplated being substituted into the TcBuster sequence, and the percentage shown below is the percentage of other Buster subfamily members that contain the canonical TcBuster amino acid at that position.
Figure 6:
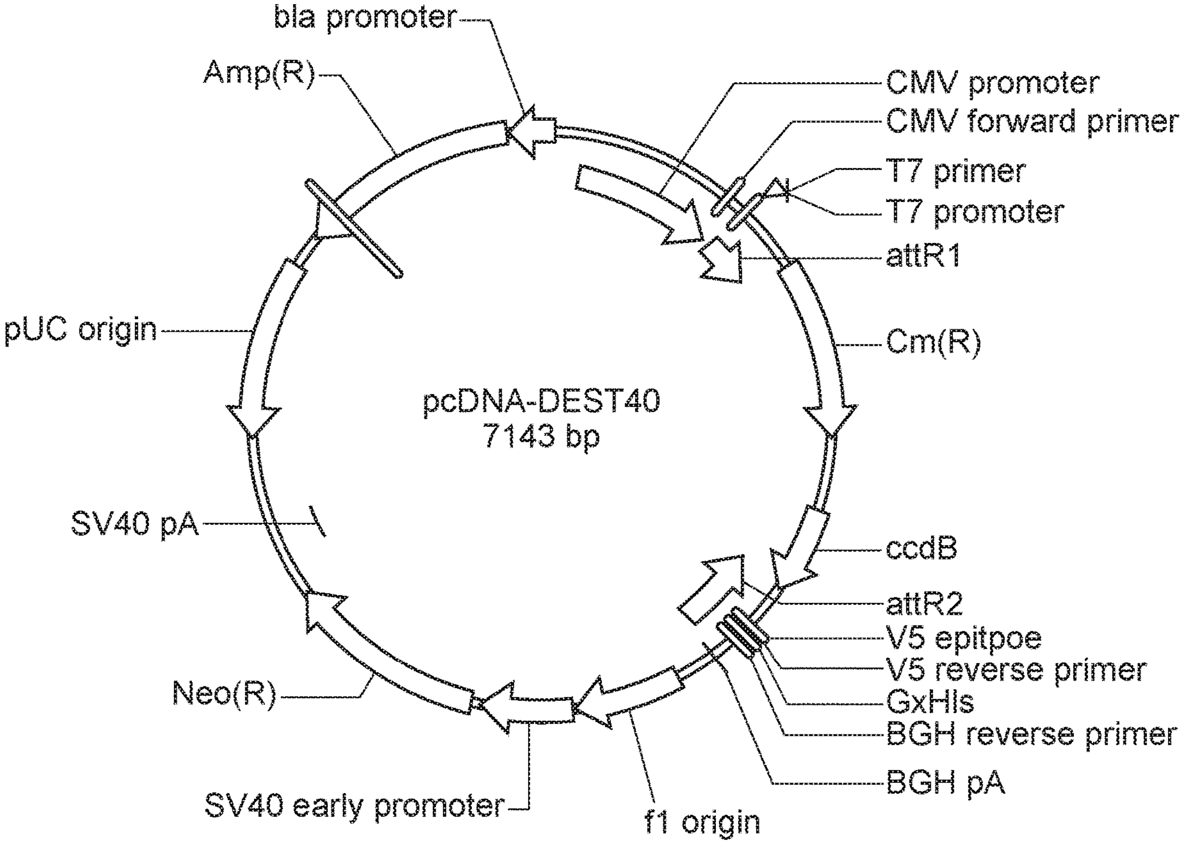
FIG. 6 shows a vector map of an exemplary expression vector pcDNA-DEST40 that was used to test TcBuster transposase mutants.

The hAT transposon family consists of two subfamilies: AC, such as has hobo, hermes, and Tol2, and the Buster subfamily, such as SPIN and TcBuster. Amino acid sequence of TcBuster was aligned to amino acid sequences of both AC and Buster subfamily members to identify key amino acids that are not conserved in TcBuster that may be targets of hyperactive substitutions. Alignment of TcBuster to the AC subfamily members Hermes, Hobo, Tag2, Tam3, Herves, Restless, and Tol2 allowed us to identify amino acids within areas of high conservation that could be substituted in TcBuster (FIG. 4). Further, sequence alignment of TcBuster to the Buster subfamily led to a larger number of candidate amino acids that may be substituted (FIG. 5). Candidate TcB transposase mutants were generated using oligonucleotides comprising site mutations as listed in Table 9. The mutants were then sequence verified, cloned into pCDNA-DEST40 expression vector (FIG. 6) and mini-prepped prior to transfection.

TABLE 9

| Amino Acid Substitutions | Oligo Name | Oligonucleotide Sequence (5'-3') | SEQ ID NO |
|---|---|---|---|
| Q82E | TCB Q82E FWD | GATTTGCGAGgAGGTAGTCAAC | 14 |
| Q82E | TCB Q82E REV | ACACAAAGTCCGTTGGGC | 15 |
| A358E | TCBA358E FWD | CGCGTCTTCGaaTTGCTGTGTGAC | 16 |
| A358E | TCBA358E REV | CGCATTCAACGGCCGAGA | 17 |
| A358S | TCBA358S FWD | GCGCGTCTTCagTTTGCTGTGTGACG | 18 |
| A358S | TCBA358S REV | GCATTCAACGGCCGAGAC | 19 |
| A358K | TCBA358K FWD | GCGCGTCTTCaagTTGCTGTGTGACG | 20 |
| A358K | TCBA358K REV | GCATTCAACGGCCGAGAC | 21 |
| S447E | TCBS447E FWD | CAAGGTAAATgagCGCATTAACAGTATTAAATC | 22 |
| S447E | TCBS447E REV | AAGATTGTGCTATTCGGC | 23 |

TABLE 9-continued

| Amino Acid Substitutions | Oligo Name | Oligonucleotide Sequence (5'-3') | SEQ ID NO |
|---|---|---|---|
| I452F | TCBI452F FWD | CATTAACAGTtTTAAATCAAAGTTGAAG | 24 |
| I452F | TCBI452F REV | CGGCTATTTACCTTGAAG | 25 |
| N281E | TCBN281E FWD | CATCCCATGGgaaCTGTGTTACC | 26 |
| N281E | TCBN281E REV | GAGTGCTTTTCGAAATAGG | 27 |
| I233Q | TCBI233Q FWD | CGGTCTTGCAcagCTGCTTGTGTTTG | 28 |
| I233Q | TCBI233Q REV | GCAACATCTGTTGACTCG | 29 |
| P510D | TCBP510D FWD | GTATTTTCCAgatACGTGTAATAATATCTCCTG | 30 |
| P510D | TCBP510D REV | TCCAGAAAGGTGTTCTTAAG | 31 |
| P510N | TCBP510N FWD | GTATTTTCCAaatACGTGTAATAATATCTCC | 32 |
| P510N | TCBP510N REV | TCCAGAAAGGTGTTCTTAAG | 33 |
| E519R | TCBE519R FWD | CTCCTGGGTGcggAATCCTTTCAATG | 34 |
| E519R | TCBE519R REV | ATATTATTACACGTAGGTGG | 35 |
| K590T | TCBK590T FWD | GAAATTAGCACACGAGCTGTC | 36 |
| K590T | TCBK590T REV | TGGAAATTCGTCCATCAG | 37 |
| N85S | TCBN85S FWD | GCAGGTAGTCagcAATTCCTCAC | 38 |
| N85S | TCBN85S REV | TCGCAAATCACACAAAGTC | 39 |
| S109D | TCBS109D FOR | TAAAGGCAAGgacGAATACTTCAAAAGAAAATGTAAC | 40 |
| S109D | TCBS109D REV | TAAAGGCAAGgacGAATACTTCAAAAGAAAATGTAAC | 41 |
| K135E | TCBK135E FWD | GGACGATAACgagAACCTCCTGA | 42 |
| K135E | TCBK135E REV | CTTACGTATCGCTCAAAAGTATG | 43 |
| D99A | TcB-D99A F | ACGCCATTTGgCaACAAAGCATC | 44 |
| D99A | TcB-D99A R | TTCAGTTTGGCCGGGTTA | 45 |
| D132A | TcB-D132A-F | ATACGTAAGGgcaGATAACAAGAACC | 46 |
| D132A | TcB-D132A-R | CGCTCAAAAGTATGCTTC | 47 |
| E159A | TcB-E159A-F | TACCATAGCGgCgAAGTTGATCAAG | 48 |
| E159A | TcB-E159A-R | TATGCCTCGCCCTGTTTA | 49 |
| D189A | TcB-D189A-F | CCCCCTGTCCgcaACGACTATTTC | 50 |
| D189A | TcB-D189A-R | ACGAGATCAACTTTGCTC | 51 |
| D227A | TcB-D227A-F | CGAGTCAACAgcaGTTGCCGGTC | 52 |

TABLE 9-continued

| Amino Acid Substitutions | Oligo Name | Oligonucleotide Sequence (5'-3') | SEQ ID NO |
|---|---|---|---|
| D227A | TcB-D227A-R | TCCATCTGCAGCGTAAAC | 53 |
| E243A | TcB-E243A-F | GTACATACATgcaAGCTCTTTTG | 54 |
| E243A | TcB-E243A-R | CTAACAAACACAAGCAGG | 55 |
| V377T | TcB-V377T-F | TCATACCGAAacgAGGTGGCTGTC | 56 |
| V377T | TcB-V377T-R | AGAAGAAGATTTTTATGCAGG | 57 |
| S225W | TcB-S225W-F | GATGGACGAGtggACAGATGTTGC | 58 |
| S225W | TcB-S225W-R | TGCAGCGTAAACCCACAT | 59 |
| Y155F | TcB-Y155F-F | GGGCGAGGCAtttACCATAGCGG | 60 |
| Y155F | TcB-Y155F-R | TGTTTAGCTATTCTCAAACTGACGAGATAAG | 61 |
| D132A | TcB-D132A-F | ATACGTAAGGgcaGATAACAAGAACC | 62 |
| D132A | TcB-D132A-R | CGCTCAAAAGTATGCTTC | 63 |
| E159A | TcB-E159A-F | TACCATAGCGgCgAAGTTGATCAAG | 64 |
| E159A | TcB-E159A-R | TATGCCTCGCCCTGTTTA | 65 |
| D189A | TcB-D189A-F | CCCCCTGTCCgcaACGACTATTTC | 66 |
| D189A | TcB-D189A-R | ACGAGATCAACTTTGCTC | 67 |
| D227A | TcB-D227A-F | CGAGTCAACAgcaGTTGCCGGTC | 68 |
| D227A | TcB-D227A-R | TCCATCTGCAGCGTAAAC | 69 |
| E243A | TcB-E243A-F | GTACATACATgcaAGCTCTTTTG | 70 |
| E243A | TcB-E243A-R | CTAACAAACACAAGCAGG | 71 |
| V377T | TcB-V377T-F | TCATACCGAAacgAGGTGGCTGTC | 72 |
| V377T | TcB-V377T-R | AGAAGAAGATTTTTATGCAGG | 73 |
| S224W | TcB-S224W-F | GATGGACGAGtggACAGATGTTGC | 74 |
| S224W | TcB-S224W-R | TGCAGCGTAAACCCACAT | 75 |
| Y155F | TcB-Y155F-F | GGGCGAGGCAtttACCATAGCGG | 76 |
| Y155F | TcB-Y155F-R | TGTTTAGCTATTCTCAAACTGACGAGATAAG | 77 |

Figure 7:
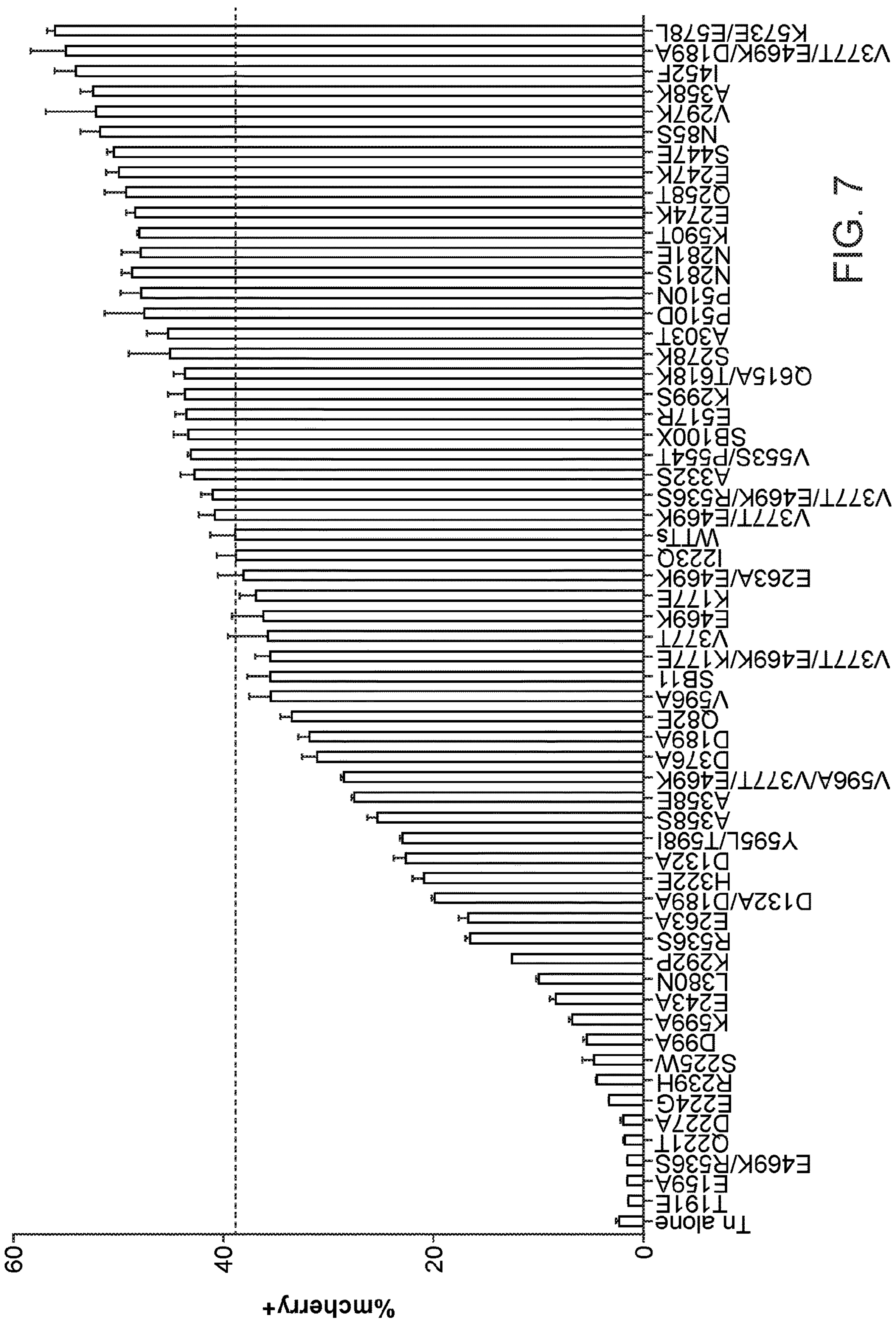
FIG. 7 is a graph quantifying the transposition efficiency of exemplary TcBuster transposase mutants, as measured by percent of mCherry positive cells in HEK-293T cells that were transfected with TcBuster transposon Tn-8 (illustrated in FIG. 1) with the exemplary transposase mutants.

To examine the transposition efficiency of the TcB transposase mutants, HEK-293T cells were transfected with TcB Tn-8 (mCherry-puromycin cassette) with WT transposase or V596A mutant transposase, or the candidate transposase mutants in duplicate. Cells were grown in DMEM complete (without drug selection) and mCherry expression was assessed by flow cytometry on Day 14 post-transfection. Over 20 TcB transposase mutants were identified that had transposition efficiency greater than the wild-type transposase (FIG. 7). It was discovered that among these examined mutants, one mutant transposase containing a combination of three amino acid substitutions, D189A, V377T, and E469K, led to a substantial increase in transposition activity, as compared to mutants containing respective single substitutions. Mutants with high transposition activity also included, among others, K573E/E578L, I452F, A358K, V297K, N85S, S447E, E247K, and Q258T.

Among these examined mutants, it was discovered that most of substitutions to a positively charged amino acid, such as Lysine (K) or Arginine (R), in proximity to one of the catalytic triad amino acids (D234, D289, and E589) increased transposition. In addition, removal of a positive charge, or addition of a negative charge decreased transposition. These data suggests that amino acids close to the catalytic domain may help promote the transposition activity of TcB, in particular, when these amino acids are mutated to positively charged amino acids.

The amino acid sequence of the hyperactive TcBuster mutant D189A/V377T/E469K (SEQ ID NO: 78) is illustrated in FIG. 12. Further mutational analysis of this mutant will be performed. As illustrated in FIG. 13, the TcBuster mutant D189A/V377T/E469K/I452F (SEQ ID NO: 79) will be constructed. As illustrated in FIG. 14, the TcBuster mutant D189A/V377T/E469K/N85S (SEQ ID NO: 80) will be constructed. As illustrated in FIG. 15, the Tc Buster mutant D189A/V377T/E469K/S358K (SEQ ID NO: 81) will be constructed. As illustrated in FIG. 16, the Tc Buster mutant D189A/V377T/E469K/K573E/E578L (SEQ ID NO:

13) will be constructed. In each of FIGS. 12-16, the domains of TcBuster are indicated as follows: ZnF-BED (lowercase lettering), DNA Binding/oligomization domain (bold lettering), catalytic domain (underlined lettering), and insertion domain (italicized lettering); the core D189A/V377T/E469K substitutions are indicated in larger, bold, italicized, and underlined letters; and the additional substitutions are indicated in large, bold letters. Each of these constructs will be tested as already described and are anticipated to show hyperactivity in comparison to the wild type TcBuster.

Example 4. Exemplary Fusion Transposase Containing Tag

Figure 9:
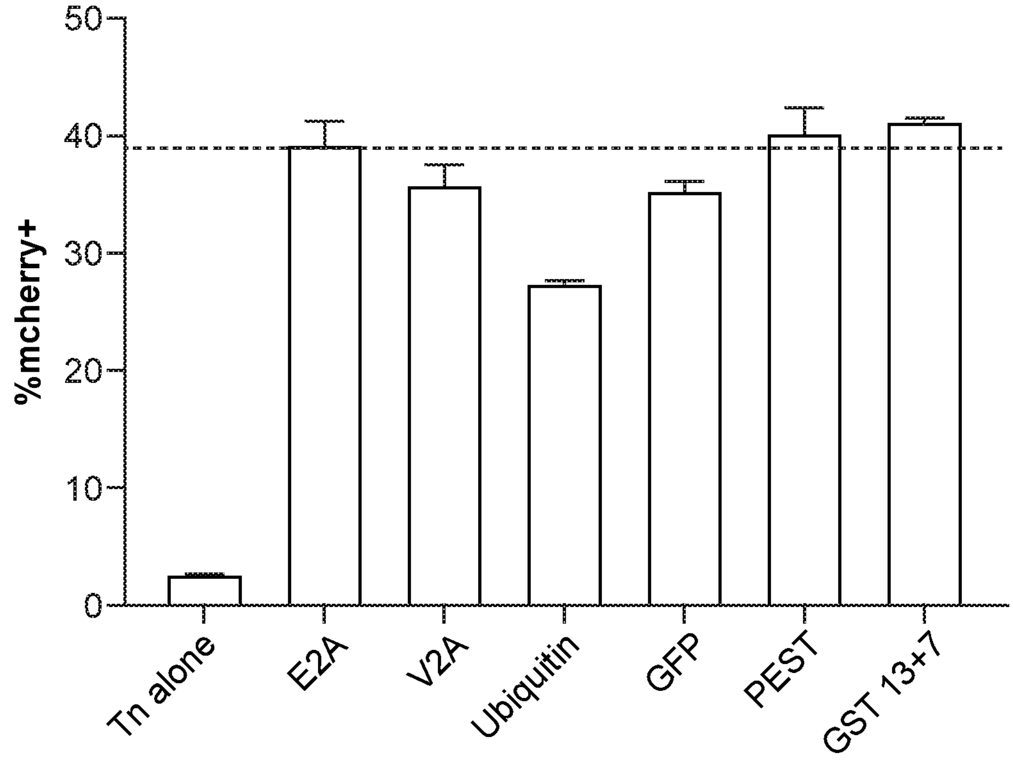
FIG. 9 is a graph quantifying the transposition efficiency of exemplary TcBuster transposases containing different tags as measured by percent of mCherry positive cells in HEK-293T cells that were transfected with TcBuster transposon Tn-8 (illustrated in FIG. 1) with the exemplary transposases containing the tags.

The aim of this study was to generate and examine the transposition efficiency of fusion TcBuster transposases. As an example, protein tag, GST or PEST domain, was fused to N-terminus of TcBuster transposase to generate fusion TcBuster transposases. A flexible linker GGSGGSGGSGGSGTS (SEQ ID NO: 9), which was encoded by SEQ ID NO: 10, was used to separate the GST domain/PEST domain from TcBuster transposase. The presence of this flexibility linker may minimize non-specific interaction in the fusion protein, thus increasing its activity. The exemplary fusion transposases were transfected with TcB Tn-8 as described above and transposition efficiency was measured by mCherry expression on Day 14 by flow cytometry. Transposition efficiency was not affected by tagging of GFP or PEST domain (FIG. 9), suggesting that fusing the transposase DNA binding domains to direct integration of TcBuster cargo to select genomic sites, such as safe harbor sites, could be a viable option for TcBuster allowing for a safer integration profile.

Example 5. Exemplary Fusion Transposase Comprising Tale Domain

The aim of this study is to generate a fusion TcBuster transposase comprising a TALE domain and to examine the transposition activity of the fusion transposase. A TALE sequence (SEQ ID NO: 11) is designed to target human AAVS1 (hAAVS1) site of human genome. The TALE sequence is thus fused to N-terminus of a wild-type TcBuster transposase (SEQ ID NO: 1) to generate a fusion transposase. A flexible linker Gly4Ser2 (SEQ ID NO: 88), which is encoded by SEQ ID NO: 12, is used to separate the TALE domain and the TcBuster transposase sequence. The exemplary fusion transposase has an amino acid sequence SEQ ID NO: 8.

The exemplary fusion transposase will be transfected with a TcB Tn-8 as described above into Hela cells with the aid of electroporation. The TcB Tn-8 comprises a reporter gene mCherry. The transfection efficiency can be examined by flow cytometry 2 days post-transfection that counts mCherry-positive cells. Furthermore, next-generation sequencing will be performed to assess the mCherry gene insertion site in the genome. It is expected that the designed TALE sequence can mediate the target insertion of the mCherry gene at a genomic site near hAAVS1 site.

Example 6. Transposition Efficiency in Primary Human T-Cells

The aim of this study was to develop TcBuster transposon system to engineer primary CD3+ T cells. To this end, inventors incorporated an exemplary TcBuster transposon carrying a GFP transgene into a mini-circle plasmid. Activated CD3+ T cells were electroporated with TcB mini-circle transposon and RNA transposases, such as WT TcBuster transposase, and select exemplary mutants as described in Example 2. The transgene expression was monitored for 21 days post-electroporation by flow cytometry.

Figure 10B:
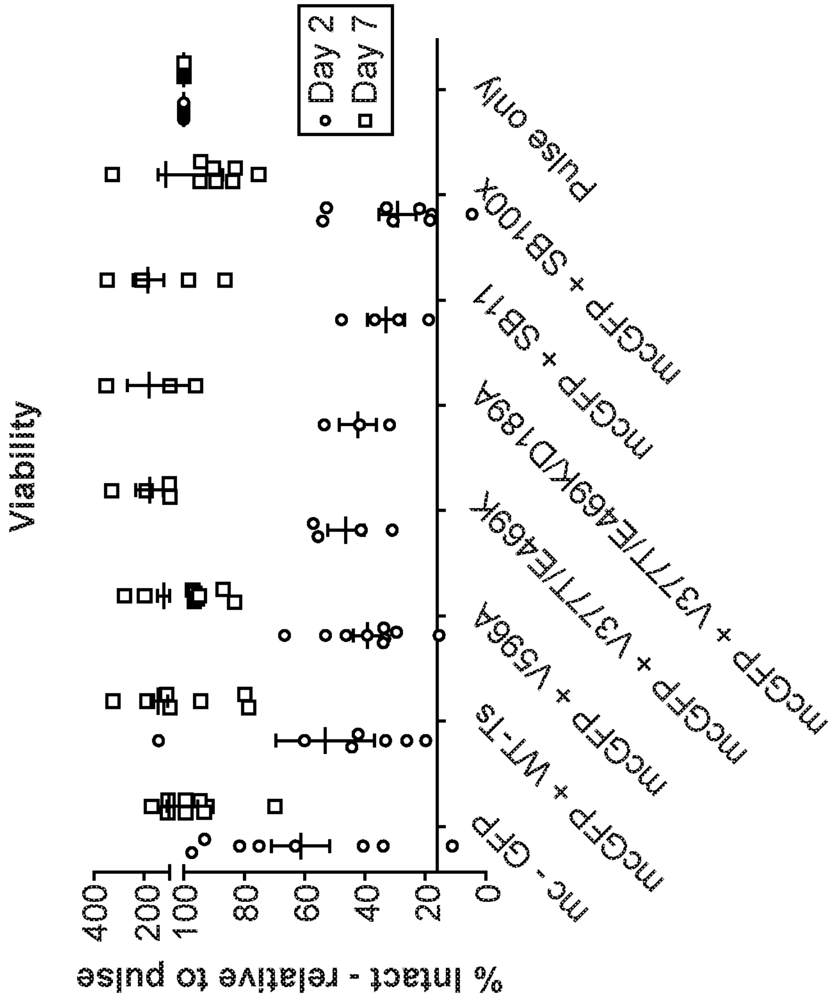
FIG. 10B is a graph quantifying viability of the transfected T cells 2 and 7 days post-transfection by flow cytometry. Data is relative to pulse control.
Figure 10A:
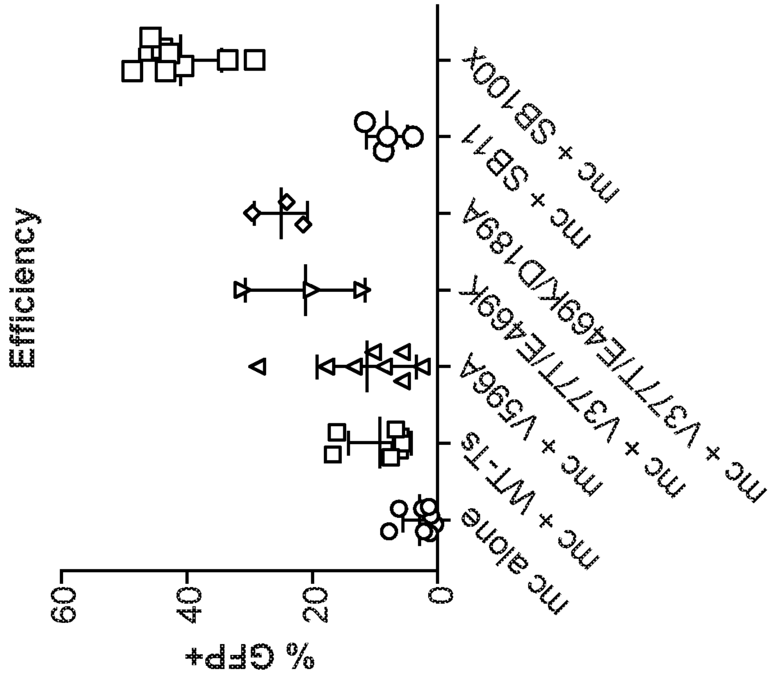
FIG. 10A is a graph quantifying the transposition efficiency of exemplary TcBuster transposition systems in human CD3+ T cells as measured by percent of GFP positive cells.

It was found that transposition of the TcB transposon was improved nearly two folds using the exemplary mutants, V377T/E469K and V377T/E469K/D189A, 14 days post-transfection compared to the WT TcBuster transposase and V596A mutant transposase (FIG. 10A). Further, mean transposition efficiency with the hyperactive mutants V377T/E469K and V377T/E469K/D189A was two (mean=20.2) and three (mean=24.1) times more efficient compared to SB11 (mean=8.4), respectively.

Next, the viability of CD3+ T cells was assessed two days post-electroporation with the mini-circle TcB transposon and RNA transposase. It was found that viability was moderately decreased when CD3+ T-cells were transfected with TcB mini-circle and RNA transposase; however, the cells quickly recovered viability by Day 7 (FIG. 10B). These experiments demonstrate the competency of the TcBuster transposon system, according to some embodiments of the present disclosure, in cellular engineering of primary T cells.

Example 7. Generation of Chimeric Antigen Receptor-Modified T Cells for Treatment of Cancer Patient A mini-circle plasmid containing aforementioned TcB Tn-8 construct can be designed to harbor a chimeric antigen receptor (CAR) gene between the inverted repeats of the transposon. The CAR can be designed to have specificity for the B-cell antigen CD19, coupled with CD137 (a costimulatory receptor in T cells [4-1BB]) and CD3-zeta (a signal-transduction component of the T-cell antigen receptor) signaling domains.

Autologous T cells will be obtained from peripheral blood of a patient with cancer, for example, leukemia. The T cells can be isolated by lysing the red blood cells and depleting the monocytes by centrifugation through a PERCOLL™ gradient. CD3+ T cells can be isolated by flow cytometry using anti-CD3/anti-CD28-conjugated beads, such as DYNABEAD M-450 CD3/CD28T. The isolated T cells will be cultured under standard conditions according to GMP guidance.

Genetic modification of the primary T cells will be conducted using a mutant TcBuster transposase (SEQ ID NO: 13) comprising amino acid substitutions V377T, E469K, D189A, K573E and E578L and the TcBuster Tn-8 transposase comprising the CAR, as described above. The T cells will be electroporated in the presence of the mutant TcBuster transposase and the CAR-containing Tn-8 transposase. Following transfection, T cells will be treated with immunostimulatory reagents (such as anti-CD3 antibody and IL-2, IL-7, and IL-15) for activation and expansion. Validation of the transfection will be performed by next-generation sequencing 2 weeks post-transfection. The transfection efficiency and transgene load in the transfected T cells can be determined to assist the design of treatment regimen. Certain measure will also be taken to eliminate any safety concern if risky transgene insertion site is uncovered by the sequencing results.

Infusion of the chimeric antigen receptor modified T cells (CAR-T cells) back to the cancer patient will start after validation of transgene insertion and in vitro expansion of the CAR-T cells to a clinically desirable level.

The infusion dose will be determined by a number of factors, including, but not limited to, the stage of the cancer, the treatment history of the patient, and the CBC (complete blood cell count) and vital signs of the patient on the day of treatment. Infusion dose may be escalated or deescalated depending on the progression of the disease, the repulsion reaction of the patient, and many other medical factors. In the meantime, during the treatment regimen, quantitative polymerase-chain-reaction (qPCR) analysis will be performed to detect chimeric antigen receptor T cells in blood and bone marrow. The qPCR analysis can be utilized to make medical decision regarding the dosing strategy and other treatment plans.

TABLE 10

Amino Acid and Nucleotide Sequences

| Sequence Description | Amino Acid Sequence Or Nucleotide Sequence (SEQ ID NO) |
|---|---|
| Wild-type TcBuster transposase | (accession number: ABF20545)<br>MMLNWLKSGKLESQSQEQSSCYLENSNCLPPTLDSTDIIGEENKAGTTSRKKR<br>KYDEDYLNFGFTWTGDKDEPNGLCVICEQVVNNSSLNPAKLKRHLDTKHPTLK<br>GKSEYFKRKCNELNQKKHTFERYVRDDNKNLLKASYLVSLRIAKQGEAYTIAE<br>KLIKPCTKDLTTCVFGEKFASKVDLVPLSDTTISRRIEDMSYFCEAVLVNRLK<br>NAKCGFTLQMDESTDVAGLAILLVFVRYIHESSFEEDMLFCKALPTQTTGEEI<br>FNLLNAYFEKHSIPWNLCYHICTDGAKAMVGVIKGVIARIKKLVPDIKASHCC<br>LHRHALAVKRIPNALHEVLNDAVKMINFIKSRPLNARVFALLCDDLGSLHKNL<br>LLHTEVRWLSRGKVLTRFWELRDEIRIFFNEREFAGKLNDTSWLQNLAYIADI<br>FSYLNEVNLSLQGPNSTIFKVNSRINSIKSKLKLWEECITKNNTECFANLNDF<br>LETSNTALDPNLKSNILEHLNGLKNTFLEYFPPTCNNISWVENPFNECGNVDT<br>LPIKEREQLIDIRTDTTLKSSFVPDGIGPFWIKLMDEFPEISKRAVKELMPFV<br>TTYLCEKSFSVYVATKTKYRNRLDAEDDMRLQLTTIHPDIDNLCNNKQAQKSH<br>(SEQ ID NO: 1) |
| Wild-type TcBuster transposase | atgatgttgaattggctgaaaagtggaaagcttgaaagtcaatcacaggaaca<br>gagttcctgctaccttgagaactctaactgcctgccaccaacgctcgattcta<br>cagatattatcggtgaagagaacaaagctggtaccacctctcgcaagaagcgg<br>aaatatgacgaggactatctgaacttcggttttacatggactggcgacaagga<br>tgagcccaacggactttgtgtgatttgcgagcaggtagtcaacaattcctcac<br>ttaacccggccaaactgaaacgccatttggacacaaagcatccgacgcttaaa<br>ggcaagagcgaatacttcaaaagaaaatgtaacgagctcaatcaaaagaagca<br>tacttttgagcgatacgtaagggacgataacaagaacctcctgaaagcttctt<br>atctcgtcagtttgagaatagctaaacagggcgaggcatataccatagcggag<br>aagttgatcaagccttgcaccaaggatctgacaacttgcgtatttggagaaaa<br>attcgcgagcaaagttgatctcgtccccctgtccgacacgactatttcaaggc<br>gaatcgaagacatgagttacttctgtgaagccgtgctggtgaacaggttgaaa<br>aatgctaaatgtgggtttacgctgcagatggacgagtcaacagatgttgccgg<br>tcttgcaatcctgcttgtgtttgttaggtacatacatgaaagctcttttgagg<br>aggatatgttgttctgcaaagcacttcccactcagacgacaggggaggagatt<br>ttcaatcttctcaatgcctatttcgaaaagcactccatcccatggaatctgtg<br>ttaccacatttgcacagacggtgccaaggcaatggtaggagttattaaaggag<br>tcatagcgagaataaaaaaactcgtccctgatataaaagctagccactgttgc<br>ctgcatcgccacgctttggctgtaaagcgaataccgaatgcattgcacgaggt<br>gctcaatgacgctgttaaaatgatcaacttcatcaagtctcggccgttgaatg<br>cgcgcgtcttcgctttgctgtgtgacgatttggggagcctgcataaaaatctt<br>cttcttcataccgaagtgaggtggctgtctagaggaaaggtgctgacccgatt<br>ttgggaactgagagatgaaattagaattttcttcaacgaaagggaatttgccg<br>ggaaattgaacgacaccagttggttgcaaaatttggcatatatagctgacata<br>ttcagttatctgaatgaagttaatctttccctgcaagggccgaatagcacaat<br>cttcaaggtaaatagccgcattaacagtattaaatcaaagttgaagttgtggg<br>aagagtgtataacgaaaaataacactgagtgttttgcgaacctcaacgatttt<br>ttggaaacttcaaacactgcgttggatccaaacctgaagtctaatattttgga<br>acatctcaacggtcttaagaacacctttctggagtattttccacctacgtgta<br>ataatatctcctgggtggagaatcctttcaatgaatgcggtaacgtcgataca<br>ctcccaataaaagagagggaacaattgattgacatacggactgatacgacatt<br>gaaatcttcattcgtgcctgatggtataggaccattctggatcaaactgatgg<br>acgaatttccagaaattagcaaacgagctgtcaaagagctcatgccatttgta<br>accacttacctctgtgagaaatcattttccgtctatgtagccacaaaaacaaa<br>atatcgaaatagacttgatgctgaagacgatatgcgactccaacttactacta<br>tccatccagacattgacaacctttgtaacaacaagcaggctcagaaatcccac<br>tga<br>(SEQ ID NO: 2) |
| Wild-type TcBuster transposase Codon Optimized DNA sequence | ATGATGCTGAATTGGCTGAAGAGCGGCAAGCTGGAGTCACAGTCACAGGAACA<br>GTCCTCATGTTATCTGGAGAACAGTAATTGTCTGCCCCCTACCCTGGACTCTA<br>CAGATATCATCGGCGAGGAGAATAAGGCCGGCACCACAAGCCGGAAGAAGAGA<br>AAGTACGACGAGGATTATCTGAATTTCGGCTTTACCTGGACAGGCGACAAGGA<br>TGAGCCAAACGGCCTGTGCGTGATCTGTGAGCAGGTGGTGAACAATAGCTCCC<br>TGAACCCAGCCAAGCTGAAGCGGCACCTGGACACCAAGCACCCCACACTGAAG<br>GGCAAGAGCGAGTACTTTAAGAGAAAGTGCAACGAGCTGAATCAGAAGAAGCA<br>CACCTTCGAGAGGTACGTGCGCGACGATAACAAGAATCTGCTGAAGGCCTCCT<br>ATCTGGTGTCTCTGAGAATCGCCAAGCAGGGCGAGGCCTACACCATCGCCGAG<br>AAGCTGATCAAGCCATGCACAAAGGACCTGACCACATGCGTGTTCGGCGAGAA<br>GTTTGCCAGCAAGGTGGACCTGGTGCCCCTGAGCGATACCACAATCTCCCGGA<br>GAATCGAGGATATGTCCTATTTTTGCGAGGCCGTGCTGGTGAACAGGCTGAAG |

TABLE 10-continued

Amino Acid and Nucleotide Sequences

| Sequence Description | Amino Acid Sequence Or Nucleotide Sequence (SEQ ID NO) |
|---|---|
| | AATGCCAAGTGTGGCTTCACCCTGCAGATGGACGAGTCCACAGATGTGGCCGG<br>CCTGGCCATCCTGCTGGTGTTTGTGCGCTACATCCACGAGTCTAGCTTCGAGG<br>AGGACATGCTGTTTTGCAAGGCCCTGCCTACCCAGACCACAGGCGAGGAGATC<br>TTCAACCTGCTGAATGCCTACTTTGAGAAGCACTCTATCCCATGGAACCTGTG<br>CTATCACATCTGTACCGACGGAGCAAAGGCAATGGTGGGCGTGATCAAGGGCG<br>TGATCGCCAGGATCAAGAAGCTGGTGCCCGATATCAAGGCCTCTCACTGCTGT<br>CTGCACAGGCACGCACTGGCAGTGAAGAGGATCCCTAACGCCCTGCACGAGGT<br>GCTGAATGACGCCGTGAAGATGATCAACTTTATCAAGAGCCGGCCTCTGAATG<br>CCAGAGTGTTCGCCCTGCTGTGCGACGATCTGGGCTCCCTGCACAAGAACCTG<br>CTGCTGCACACCGAGGTTCGGTGGCTGTCTAGAGGCAAGGTGCTGACCAGGTT<br>TTGGGAGCTGAGGGATGAGATCCGCATCTTCTTTAATGAGCGCGAGTTCGCCG<br>GCAAGCTGAATGACACAAGCTGGCTGCAGAACCTGGCCTACATCGCCGATATC<br>TTTTCCTATCTGAACGAAGTGAATCTGTCTCTGCAGGGCCCCAACAGCACCAT<br>CTTCAAGGTGAACTCCCGCATCAATTCTATCAAGAGCAAGCTGAAGCTGTGGG<br>AGGAGTGCATCACCAAGAACAATACAGAGTGTTTCGCCAACCTGAATGACTTC<br>CTGGAGACAAGCAATACAGCCCTGGATCCTAACCTGAAGTCTAATATCCTGGA<br>GCACCTGAACGGCCTGAAGAATACCTTCCTGGAGTATTTTCCACCCACATGCA<br>ACAATATCAGCTGGGTGGAGAACCCCTTCAATGAGTGTGGCAACGTGGACACC<br>CTGCCTATCAAGGAGCGGGAGCAGCTGATCGACATCAGAACAGATACCACACT<br>GAAGTCCTCTTTCGTGCCTGACGGCATCGGCCCATTTTGGATCAAGCTGATGG<br>ATGAGTTCCCTGAGATCTCCAAGCGGGCCGTGAAGGAGCTGATGCCATTTGTG<br>ACCACATACCTGTGCGAGAAGAGCTTCTCCGTGTACGTGGCCACCAAGACAAA<br>GTATAGGAACCGCCTGGATGCCGAGGACGATATGAGACTGCAGCTGACCACTA<br>TCCATCCCGACATTGACAACCTGTGCAACAACAAACAGGCCCAGAAATCCCAT<br>TGA (SEQ ID NO: 204) |
| Wild-type TcBuster transposase Codon Optimized mRNA sequence | AUGAUGCUGAAUUGGCUGAAGAGCGGCAAGCUGGAGUCACAGUCACAGGAACA<br>GUCCUCAUGUUAUCUGGAGAACAGUAAUUGUCUGCCCCCUACCCUGGACUCUA<br>CAGAUAUCAUCGGCGAGGAGAAUAAGGCCGGCACCACAAGCCGGAAGAAGAGA<br>AAGUACGACGAGGAUUAUCUGAAUUUCGGCUUUACCUGGACAGGCGACAAGGA<br>UGAGCCAAACGGCCUGUGCGUGAUCUGUGAGCAGGUGGUGAACAAUAGCUCCC<br>UGAACCCAGCCAAGCUGAAGCGGCACCUGGACACCAAGCACCCCACACUGAAG<br>GGCAAGAGCGAGUACUUUAAGAGAAAGUGCAACGAGCUGAAUCAGAAGAAGCA<br>CACCUUCGAGAGGUACGUGCGCGACGAUAACAAGAAUCUGCUGAAGGCCUCCU<br>AUCUGGUGUCUCUGAGAAUCGCCAAGCAGGGCGAGGCCUACACCAUCGCCGAG<br>AAGCUGAUCAAGCCAUGCACAAAGGACCUGACCACAUGCGUGUUCGGCGAGAA<br>GUUUGCCAGCAAGGUGGACCUGGUGCCCCUGAGCGAUACCACAAUCUCCCGGA<br>GAAUCGAGGAUAUGUCCUAUUUUUGCGAGGCCGUGCUGGUGAACAGGCUGAAG<br>AAUGCCAAGUGUGGCUUCACCCUGCAGAUGGACGAGUCCACAGAUGUGGCCGG<br>CCUGGCCAUCCUGCUGGUGUUUGUGCGCUACAUCCACGAGUCUAGCUUCGAGG<br>AGGACAUGCUGUUUUGCAAGGCCCUGCCUACCCAGACCACAGGCGAGGAGAUC<br>UUCAACCUGCUGAAUGCCUACUUUGAGAAGCACUCUAUCCCAUGGAACCUGUG<br>CUAUCACAUCUGUACCGACGGAGCAAAGGCAAUGGUGGGCGUGAUCAAGGGCG<br>UGAUCGCCAGGAUCAAGAAGCUGGUGCCCGAUAUCAAGGCCUCUCACUGCUGU<br>CUGCACAGGCACGCACUGGCAGUGAAGAGGAUCCCUAACGCCCUGCACGAGGU<br>GCUGAAUGACGCCGUGAAGAUGAUCAACUUUAUCAAGAGCCGGCCUCUGAAUG<br>CCAGAGUGUUCGCCCUGCUGUGCGACGAUCUGGGCUCCCUGCACAAGAACCUG<br>CUGCUGCACACCGAGGUUCGGUGGCUGUCUAGAGGCAAGGUGCUGACCAGGUU<br>UUGGGAGCUGAGGGAUGAGAUCCGCAUCUUCUUUAAUGAGCGCGAGUUCGCCG<br>GCAAGCUGAAUGACACAAGCUGGCUGCAGAACCUGGCCUACAUCGCCGAUAUC<br>UUUUCCUAUCUGAACGAAGUGAAUCUGUCUCUGCAGGGCCCCAACAGCACCAU<br>CUUCAAGGUGAACUCCCGCAUCAAUUCUAUCAAGAGCAAGCUGAAGCUGUGGG<br>AGGAGUGCAUCACCAAGAACAAUACAGAGUGUUUCGCCAACCUGAAUGACUUC<br>CUGGAGACAAGCAAUACAGCCCUGGAUCCUAACCUGAAGUCUAAUAUCCUGGA<br>GCACCUGAACGGCCUGAAGAAUACCUUCCUGGAGUAUUUUCCACCCACAUGCA<br>ACAAUAUCAGCUGGGUGGAGAACCCCUUCAAUGAGUGUGGCAACGUGGACACC<br>CUGCCUAUCAAGGAGCGGGAGCAGCUGAUCGACAUCAGAACAGAUACCACACU<br>GAAGUCCUCUUUCGUGCCUGACGGCAUCGGCCCAUUUUGGAUCAAGCUGAUGG<br>AUGAGUUCCCUGAGAUCUCCAAGCGGGCCGUGAAGGAGCUGAUGCCAUUUGUG<br>ACCACAUACCUGUGCGAGAAGAGCUUCUCCGUGUACGUGGCCACCAAGACAAA<br>GUAUAGGAACCGCCUGGAUGCCGAGGACGAUAUGAGACUGCAGCUGACCACUA<br>UCCAUCCCGACAUUGACAACCUGUGCAACAACAAACAGGCCCAGAAAUCCCAU<br>UGA (SEQ ID NO: 207) |
| IRDR-L-Seq1 | Cagtgttcttcaacctttgccatccggcggaaccctttgtcgagatatttttt<br>tttatggaacccttcatttagtaatacacccagatgagattttagggacagct<br>gcgttgacttgttacgaacaaggtgagcccgtgctttggtctagccaagggca<br>tggtaaagactatattcgcggcgttgtgacaatttaccgaacaactccgcggc<br>cgggaagccgatctcggcttgaacgaattgttaggtggcggtacttgggtcga<br>tatcaaagtgcatcacttcttcccgtatgcccaactttgtatagagagccact<br>gcgggatcgtcaccgtaatctgcttgcacgtagatcacataagcaccaagcgc<br>gttggcctcatgcttgaggagattgatgagcgcggtggcaatgccctgcctcc<br>ggtgctcgccggagactgcgagatcatagatata<br>(SEQ ID NO: 3) |

TABLE 10-continued

| Amino Acid and Nucleotide Sequences | |
|---|---|
| Sequence Description | Amino Acid Sequence Or Nucleotide Sequence (SEQ ID NO) |
| IRDR-R-Seq1 | >gatatcaagcttatcgataccgtcgacctcgagatttctgaacgattctagg<br>ttaggatcaaacaaaatacaatttattttaaaactgtaagttaacttaccttt<br>gcttgtctaaaccaaaaacaacaacaaaactacgaccacaagtacagttacat<br>atttttgaaaattaaggttaagtgcagtgtaagtcaactatgcgaatggataa<br>catgtttcaacatgaaactccgattgacgcatgtgcattctgaagagcggcgc<br>ggccgacgtctctcgaattgaagcaatgactcgcggaaccccgaaagcctttg<br>ggtggaaccctagggttccgcggaacacaggttgaagaacactg<br>(SEQ ID NO: 4) |
| IRDR-L-Seq2 | Cctgcaggagtgttcttcaacctttgccatccggcggaaccctttgtcgagat<br>atttttttttatggaacccttcatttagtaatacacccagatgagattttagg<br>gacagctgcgttgacttgttacgaacaaggtgagcccgtgctttggtaataaa<br>aactctaaataagatttaaatttgcatttatttaaacaaactttaaacaaaaa<br>gataaatattccaaataaaataatatataaaataaaaaataaaaattaatgac<br>tttttgcgcttgcttattattgcacaaattatcaatatcgggatggatcgtt<br>gtttttt<br>(SEQ ID NO: 5) |
| IRDR-R-Seq2 | Gagccaattcagcatcatatttctgaacgattctaggttaggatcaaacaaaa<br>tacaatttattttaaaactgtaagttaacttacctttgcttgtctaaacctaa<br>aacaacaacaaaactacgaccacaagtacagttacatatttttgaaaattaag<br>gttaagtgcagtgtaagtcaactatgcgaatggataacatgtttcaacatgaa<br>actccgattgacgcatgtgcattctgaagagcggcgcggccgacgtctctcga<br>attgaagcaatgactcgcggaaccccgaaagcctttgggtggaaccctagggt<br>tccgcggaacacaggttgaagaacactg<br>(SEQ ID NO: 6) |
| IRDR-L-Seq3 | cagtgttcttcaacctttgccatccggcggaaccctttgtcgagatattttt<br>tttatggaacccttcatttagtaatacacccagatgagattttagggacagct<br>gcgttgacttgttacgaacaaggtgagcccgtgctttggtaataaaaactcta<br>aataagatttaaatttgcatttatttaaacaaactttaaacaaaaagataaat<br>attccaaataaaataatatataaaataaaaaataaaaatta<br>(SEQ ID NO: 205) |
| IRDR-R-Seq3 | atttctgaacgattctaggttaggatcaaacaaaatacaatttattttaaaac<br>tgtaagttaacttacctttgcttgtctaaacctaaaacaacaacaaaactacg<br>accacaagtacagttacatatttttgaaaattaaggttaagtgcagtgtaagt<br>caactatgcgaatggataacatgtttcaacatgaaactccgattgacgcatgt<br>gcattctgaagagcggcgcggccgacgtctctcgaattgaagcaatgactcgc<br>ggaaccccgaaagcctttgggtggaaccctagggttccgcggaacacaggttg<br>aagaacactg<br>(SEQ ID NO: 206) |
| pcDNA-DEST 40 | gacggatcgggagatctcccgatcccctatggtgcactctcagtacaatctgc<br>tctgatgccgcatagttaagccagtatctgctccctgcttgtgtgttggaggt<br>cgctgagtagtgcgcgagcaaaatttaagctacaacaaggcaaggcttgaccg<br>acaattgcatgaagaatctgcttagggttaggcgttttgcgctgcttcgcgat<br>gtacgggccagatatacgcgttgacattgattattgactagttattaatagta<br>atcaattacggggtcattagttcatagcccatatatggagttccgcgttacat<br>aacttacggtaaatggcccgcctggctgaccgcccaacgacccccgcccattg<br>acgtcaataatgacgtatgttcccatagtaacgccaatagggactttccattg<br>acgtcaatgggtggagtatttacggtaaactgcccacttggcagtacatcaag<br>tgtatcatatgccaagtacgccccctattgacgtcaatgacggtaaatggccc<br>gcctggcattatgcccagtacatgaccttatgggactttcctacttggcagta<br>catctacgtattagtcatcgctattaccatggtgatgcggttttggcagtaca<br>tcaatgggcgtggatagcggtttgactcacggggatttccaagtctccacccc<br>attgacgtcaatgggagtttgttttggcaccaaaatcaacgggactttccaaa<br>atgtcgtaacaactccgccccattgacgcaaatgggcggtaggcgtgtacggt<br>gggaggtctatataagcagagctctctggctaactagagaacccactgcttac<br>tggcttatcgaaattaatacgactcactatagggagacccaagctggctagtt<br>aagctatcaacaagtttgtacaaaaaagctgaacgagaaacgtaaaatgatat<br>aaatatcaatatattaaattagattttgcataaaaaacagactacataatact<br>gtaaaacacaacatatccagtcactatggcggccgcattaggcaccccaggct<br>ttacactttatgcttccggctcgtataatgtgtggattttgagttaggatccg<br>gcgagattttcaggagctaaggaagctaaaatggagaaaaaaatcactggata<br>taccaccgttgatatatcccaatggcatcgtaaagaacattttgaggcatttc<br>agtcagttgctcaatgtacctataaccagaccgttcagctggatattacggcc<br>tttttaaagaccgtaaagaaaaataagcacaagttttatccggcctttattca<br>cattcttgcccgcctgatgaatgctcatccggaattccgtatggcaatgaaag<br>acggtgagctggtgatatgggatagtgttcacccttgttacaccgttttccat<br>gagcaaactgaaacgttttcatcgctctggagtgaataccacgacgatttccg<br>gcagtttctacacatatattcgcaagatgtggcgtgttacggtgaaaacctgg<br>cctatttccctaaagggtttattgagaatatgtttttcgtctcagccaatccc<br>tgggtgagtttcaccagttttgatttaaacgtggccaatatggacaacttctt<br>cgcccccgttttcaccatgggcaaatattatacgcaaggcgacaaggtgctga |

TABLE 10-continued

Amino Acid and Nucleotide Sequences

| Sequence Description | Amino Acid Sequence Or Nucleotide Sequence (SEQ ID NO) |
|---|---|
| | tgccgctggcgattcaggttcatcatgccgtctgtgatggcttccatgtcggc |
| | agaatgcttaatgaattacaacagtactgcgatgagtggcagggcggggcgta |
| | aagatctggatccggcttactaaaagccagataacagtatgcgtatttgcgcg |
| | ctgatttttgcggtataagaatatatactgatatgtatacccgaagtatgtca |
| | aaaagaggtgtgctatgaagcagcgtattacagtgacagttgacagcgacagc |
| | tatcagttgctcaaggcatatatgatgtcaatatctccggtctggtaagcaca |
| | accatgcagaatgaagcccgtcgtctgcgtgccgaacgctggaaagcggaaaa |
| | tcaggaagggatggctgaggtcgcccggtttattgaaatgaacggctcttttg |
| | ctgacgagaacagggactggtgaaatgcagtttaaggtttacacctataaaag |
| | agagagccgttatcgtctgtttgtggatgtacagagtgatattattgacacgc |
| | ccgggcgacggatggtgatccccctggccagtgcacgtctgctgtcagataaa |
| | gtctcccgtgaactttacccggtggtgcatatcggggatgaaagctggcgcat |
| | gatgaccaccgatatggccagtgtgccggtctccgttatcggggaagaagtgg |
| | ctgatctcagccaccgcgaaaatgacatcaaaaacgccattaacctgatgttc |
| | tggggaatataaatgtcaggctccgttatacacagccagtctgcaggtcgacc |
| | atagtgactggatatgttgtgttttacagtattatgtagtctgtttttttatgc |
| | aaaatctaatttaatatattgatatttatatcattttacgtttctcgttcagc |
| | tttcttgtacaaagtggttgatctagagggcccgcggttcgaaggtaagccta |
| | tccctaaccctctcctcggtctcgattctacgcgtaccggtcatcatcaccat |
| | caccattgagtttaaacccgctgatcagcctcgactgtgccttctagttgcca |
| | gccatctgttgtttgcccctcccccgtgccttccttgaccctggaaggtgcca |
| | ctcccactgtcctttcctaataaaatgaggaaattgcatcgcattgtctgagt |
| | aggtgtcattctattctggggggtggggtggggcaggacagcaagggggagga |
| | ttgggaagacaatagcaggcatgctggggatgcggtgggctctatggcttctg |
| | aggcggaaagaaccagctggggctctagggggtatccccacgcgccctgtagc |
| | ggcgcattaagcgcggcgggtgtggtggttacgcgcagcgtgaccgctacact |
| | tgccagcgccctagcgcccgctcctttcgctttcttcccttcctttctcgcca |
| | cgttcgccggctttccccgtcaagctctaaatcgggggctccctttagggttc |
| | cgatttagtgctttacggcacctcgaccccaaaaaacttgattagggtgatgg |
| | ttcacgtagtgggccatcgccctgatagacggtttttcgccctttgacgttgg |
| | agtccacgttctttaatagtggactcttgttccaaactggaacaacactcaac |
| | cctatctcggtctattcttttgatttataagggattttgccgatttcggccta |
| | ttggttaaaaaatgagctgatttaacaaaaatttaacgcgaattaattctgtg |
| | gaatgtgtgtcagttagggtgtggaaagtccccaggctccccagcaggcagaa |
| | gtatgcaaagcatgcatctcaattagtcagcaaccaggtgtggaaagtcccca |
| | ggctccccagcaggcagaagtatgcaaagcatgcatctcaattagtcagcaac |
| | catagtcccgcccctaactccgcccatcccgcccctaactccgcccagttccg |
| | cccattctccgccccatggctgactaattttttttatttatgcagaggccgag |
| | gccgcctctgcctctgagctattccagaagtagtgaggaggcttttttggagg |
| | cctaggcttttgcaaaaagctcccgggagcttgtatatccattttcggatctg |
| | atcaagagacaggatgaggatcgtttcgcatgattgaacaagatggattgcac |
| | gcaggttctccggccgcttgggtggagaggctattcggctatgactgggcaca |
| | acagacaatcggctgctctgatgccgccgtgttccggctgtcagcgcaggggc |
| | gcccggttctttttgtcaagaccgacctgtccggtgccctgaatgaactgcag |
| | gacgaggcagcgcggctatcgtggctggccacgacgggcgttccttgcgcagc |
| | tgtgctcgacgttgtcactgaagcgggaagggactggctgctattgggcgaag |
| | tgccggggcaggatctcctgtcatctcaccttgctcctgccgagaaagtatcc |
| | atcatggctgatgcaatgcggcggctgcatacgcttgatccggctacctgccc |
| | attcgaccaccaagcgaaacatcgcatcgagcgagcacgtactcggatggaag |
| | ccggtcttgtcgatcaggatgatctggacgaagagcatcaggggctcgcgcca |
| | gccgaactgttcgccaggctcaaggcgcgcatgcccgacggcgaggatctcgt |
| | cgtgacccatggcgatgcctgcttgccgaatatcatggtggaaaatggccgct |
| | tttctggattcatcgactgtggccggctgggtgtggcggaccgctatcaggac |
| | atagcgttggctacccgtgatattgctgaagagcttggcggcgaatgggctga |
| | ccgcttcctcgtgctttacggtatcgccgctcccgattcgcagcgcatcgcct |
| | tctatcgccttcttgacgagttcttctgagcgggactctggggttcgcgaaat |
| | gaccgaccaagcgacgcccaacctgccatcacgagatttcgattccaccgccg |
| | ccttctatgaaaggttgggcttcggaatcgttttccgggacgccggctggatg |
| | atcctccagcgcggggatctcatgctggagttcttcgcccaccccaacttgtt |
| | tattgcagcttataatggttacaaataaagcaatagcatcacaaatttcacaa |
| | ataaagcatttttttcactgcattctagttgtggtttgtccaaactcatcaat |
| | gtatcttatcatgtctgtataccgtcgacctctagctagagcttggcgtaatc |
| | atggtcatagctgtttcctgtgtgaaattgttatccgctcacaattccacaca |
| | acatacgagccggaagcataaagtgtaaagcctggggtgcctaatgagtgagc |
| | taactcacattaattgcgttgcgctcactgcccgctttccagtcgggaaacct |
| | gtcgtgccagctgcattaatgaatcggccaacgcgcggggagaggcggtttgc |
| | gtattgggcgctcttccgcttcctcgctcactgactcgctgcgctcggtcgtt |
| | cggctgcggcgagcggtatcagctcactcaaaggcggtaatacggttatccac |
| | agaatcaggggataacgcaggaaagaacatgtgagcaaaaggccagcaaaagg |
| | ccaggaaccgtaaaaaggccgcgttgctggcgtttttccataggctccgcccc |
| | cctgacgagcatcacaaaaatcgacgctcaagtcagaggtggcgaaacccgac |
| | aggactataaagataccaggcgtttccccctggaagctccctcgtgcgctctc |
| | ctgttccgaccctgccgcttaccggatacctgtccgcctttctcccttcggga |
| | agcgtggcgctttctcatagctcacgctgtaggtatctcagttcggtgtaggt |
| | cgttcgctccaagctgggctgtgtgcacgaacccccgttcagcccgaccgct |

TABLE 10-continued

| Amino Acid and Nucleotide Sequences | |
|---|---|
| Sequence Description | Amino Acid Sequence Or Nucleotide Sequence (SEQ ID NO) |
| | gcgccttatccggtaactatcgtcttgagtccaacccggtaagacacgactta tcgccactggcagcagccactggtaacaggattagcagagcgaggtatgtagg cggtgctacagagttcttgaagtggtggcctaactacggctacactagaagaa cagtatttggtatctgcgctctgctgaagccagttaccttcggaaaaagagtt ggtagctcttgatccggcaaacaaaccaccgctggtagcggtggtttttttgt ttgcaagcagcagattacgcgcagaaaaaaaggatctcaagaagatcctttga tcttttctacggggtctgacgctcagtggaacgaaaactcacgttaagggatt ttggtcatgagattatcaaaaaggatcttcacctagatccttttaaattaaaa atgaagttttaaatcaatctaaagtatatatgagtaaacttggtctgacagtt accaatgcttaatcagtgaggcacctatctcagcgatctgtctatttcgttca tccatagttgcctgactccccgtcgtgtagataactacgatacgggagggctt accatctggccccagtgctgcaatgataccgcgagacccacgctcaccggctc cagatttatcagcaataaaccagccagccggaagggccgagcgcagaagtggt cctgcaactttatccgcctccatccagtctattaattgttgccgggaagctag agtaagtagttcgccagttaatagtttgcgcaacgttgttgccattgctacag gcatcgtggtgtcacgctcgtcgtttggtatggcttcattcagctccggttcc caacgatcaaggcgagttacatgatcccccatgttgtgcaaaaaagcggttag ctccttcggtcctccgatcgttgtcagaagtaagttggccgcagtgttatcac tcatggttatggcagcactgcataattctcttactgtcatgccatccgtaaga tgcttttctgtgactggtgagtactcaaccaagtcattctgagaatagtgtat gcggcgaccgagttgctcttgcccggcgtcaatacgggataataccgcgccac atagcagaactttaaaagtgctcatcattggaaaacgttcttcggggcgaaaa ctctcaaggatcttaccgctgttgagatccagttcgatgtaacccactcgtgc acccaactgatcttcagcatcttttactttcaccagcgtttctgggtgagcaa aaacaggaaggcaaaatgccgcaaaaaagggaataagggcgacacggaaatgt tgaatactcatactcttcctttttcaatattattgaagcatttatcagggtta ttgtctcatgagcggatacatatttgaatgtatttagaaaaataaacaaatag gggttccgcgcacatttccccgaaaagtgccacctgacgtc (SEQ ID NO: 7) |
| Fusion Transposase containing wild-type TcBuster sequence and TALE DNA-binding domain targeting human AAVS1 | atgctcgagatggatccctccgacgcttcgccggccgcgcaggtggatctacg cacgctcggctacagtcagcagcagcaagagaagatcaaaccgaaggtgcgtt cgacagtggcgcagcaccacgaggcactggtgggccatgggtttacacacgcg cacatcgttgcgctcagccaacacccggcagcgttagggaccgtcgctgtcac gtatcagcacataatcacggcgttgccagaggcgacacacgaagacatcgttg gcgtcggcaaacagtggtccggcgcacgcgccctggaggccttgttgactgat gctggtgagcttagaggacctcctttgcaacttgatacaggccagcttctgaa aatcgccaagaggggtggggtcaccgcggtcgaggccgtacacgcctggagaa atgcactgaccggggctcctcttaacCTGACCCCAGACCAGGTAGTCGCAATC GCGTCAAACGGAGGGGGAAAGCAAGCCCTGGAAACCGTGCAAAGGTTGTTGCC GGTCCTTTGTCAAGACCACGGCCTTACACCGGAGCAAGTCGTGGCCATTGCAT CCCACGACGGTGGCAAACAGGCTCTTGAGACGGTTCAGAGACTTCTCCCAGTT CTCTGTCAAGCCCACGGGCTGACTCCCGATCAAGTTGTAGCGATTGCGTCGCA TGACGGAGGGAAACAAGCATTGGAGACTGTCCAACGGCTCCTTCCCGTGTTGT GTCAAGCCCACGGTTTGACGCCTGCACAAGTGGTCGCCATCGCCTCCAATATT GGCGGTAAGCAGGCGCTGGAAACAGTACAGCGCCTGCTGCCTGTACTGTGCCA GGATCATGGACTGACGGCCAAGCTGGCCGGGGGCGCCCCCGCCGTGGGCGGGG GCCCCAAGGCCGCCGATAAATTCGCCGCCACCatgatgttgaattggctgaaa agtggaaagcttgaaagtcaatcacaggaacagagttcctgctaccttgagaa ctctaactgcctgccaccaacgctcgattctacagatattatcggtgaagaga acaaagctggtaccacctctcgcaagaagcggaaatatgacgaggactatctg aacttcggttttacatggactggcgacaaggatgagcccaacggactttgtgt gatttgcgagcaggtagtcaacaattcctcacttaacccggccaaactgaaac gccatttggacacaaagcatccgacgcttaaaggcaagagcgaatacttcaaa agaaaatgtaacgagctcaatcaaaagaagcatacttttgagcgatacgtaag ggacgataacaagaacctcctgaaagcttcttatctcgtcagtttgagaatag ctaaacagggcgaggcatataccatagcggagaagttgatcaagccttgcacc aaggatctgacaacttgcgtatttggagaaaaattcgcgagcaaagttgatct cgtcccccctgtccgacacgactatttcaaggcgaatcgaagacatgagttact tctgtgaagccgtgctggtgaacaggttgaaaaatgctaaatgtgggtttacg ctgcagatggacgagtcaacagatgttgccggtcttgcaatcctgcttgtgtt tgttaggtacatacatgaaagctcttttgaggaggatatgttgttctgcaaag cacttcccactcagacgacaggggaggagattttcaatcttctcaatgcctat ttcgaaaagcactccatcccatggaatctgtgttaccacatttgcacagacgg tgccaaggcaatggtaggagttattaaaggagtcatagcgagaataaaaaaac tcgtccctgatataaaagctagccactgttgcctgcatcgccacgctttggct gtaaagcgaataccgaatgcattgcacgaggtgctcaatgacgctgttaaaat gatcaacttcatcaagtctcggccgttgaatgcgcgcgtcttcgctttgctgt gtgacgatttggggagcctgcataaaaatcttcttcttcataccgaagtgagg tggctgtctagaggaaaggtgctgacccgattttgggaactgagagatgaaat tagaattttcttcaacgaaagggaatttgccgggaaattgaacgacaccagtt ggttgcaaaatttggcatatatagctgacatattcagttatctgaatgaagtt aatctttccctgcaagggccgaatagcacaatcttcaaggtaaatagccgcat taacagtattaaatcaaagttgaagttgtgggaagagtgtataacgaaaaata acactgagtgttttgcgaacctcaacgatttttggaaacttcaaacactgcg |

TABLE 10-continued

| Amino Acid and Nucleotide Sequences | |
|---|---|
| Sequence Description | Amino Acid Sequence Or Nucleotide Sequence (SEQ ID NO) |
| | ttggatccaaacctgaagtctaatattttggaacatctcaacggtcttaagaa<br>cacctttctggagtattttccacctacgtgtaataatatctcctgggtggaga<br>atcctttcaatgaatgcggtaacgtcgatacactcccaataaaagagagggaa<br>caattgattgacatacggactgatacgacattgaaatcttcattcgtgcctga<br>tggtataggaccattctggatcaaactgatggacgaatttccagaaattagca<br>aacgagctgtcaaagagctcatgccatttgtaaccacttacctctgtgagaaa<br>tcattttccgtctatgtagccacaaaaacaaaatatcgaaatagacttgatgc<br>tgaagacgatatgcgactccaacttactactatccatccagacattgacaacc<br>tttgtaacaacaagcaggctcagaaatcccactga<br>(SEQ ID NO: 8) |
| Flexible linker (Example 4) | GGSGGSGGSGGSGTS<br>(SEQ ID NO: 9) |
| Flexible linker (Example 4) | GGAGGTAGTGGCGGTAGTGGGGGCTCCGGTGGGAGCGGCACCTCA<br>(SEQ ID NO: 10) |
| TALE domain targeting hAAVS1 site (Example 5) | atgctcgagatggatccctccgacgcttcgccggccgcgcaggtggatctacg<br>cacgctcggctacagtcagcagcagcaagagaagatcaaaccgaaggtgcgtt<br>cgacagtggcgcagcaccacgaggcactggtgggccatgggtttacacacgcg<br>cacatcgttgcgctcagccaacacccggcagcgttagggaccgtcgctgtcac<br>gtatcagcacataatcacggcgttgccagaggcgacacacgaagacatcgttg<br>gcgtcggcaaacagtggtccggcgcacgcgccctggaggccttgttgactgat<br>gctggtgagcttagaggacctcctttgcaacttgatacaggccagcttctgaa<br>aatcgccaagaggggtggggtcaccgcggtcgaggccgtacacgcctggagaa<br>atgcactgaccggggctcctcttaacCTGACCCCAGACCAGGTAGTCGCAATC<br>GCGTCAAACGGAGGGGGAAAGCAAGCCCTGGAAACCGTGCAAAGGTTGTTGCC<br>GGTCCTTTGTCAAGACCACGGCCTTACACCGGAGCAAGTCGTGGCCATTGCAT<br>CCCACGACGGTGGCAAACAGGCTCTTGAGACGGTTCAGAGACTTCTCCCAGTT<br>CTCTGTCAAGCCCACGGGCTGACTCCCGATCAAGTTGTAGCGATTGCGTCGCA<br>TGACGGAGGGAAACAAGCATTGGAGACTGTCCAACGGCTCCTTCCCGTGTTGT<br>GTCAAGCCCACGGTTTGACGCCTGCACAAGTGGTCGCCATCGCCTCCAATATT<br>GGCGGTAAGCAGGCGCTGGAAACAGTACAGCGCCTGCTGCCTGTACTGTGCCA<br>GGATCATGGACTGAC<br>(SEQ ID NO: 11) |
| Flexible linker (Example 5) | GGCCAAGCTGGCCGGGGGCGCCCCCGCCGTGGGCGGGGGCCCCAAGGCCGCCG<br>ATAAATTCGCCGCCACC<br>(SEQ ID NO: 12) |
| Mutant TcBuster transposase containing V377T, E469K, D189A, K573E and E578L | MMLNWLKSGKLESQSQEQSSCYLENSNCLPPTLDSTDIIGEENKAGTTSRKKR<br>KYDEDYLNFGFTWTGDKDEPNGLCVICEQVVNNSSLNPAKLKRHLDTKHPTLK<br>GKSEYFKRKCNELNQKKHTFERYVRDDNKNLLKASYLVSLRIAKQGEAYTIAE<br>KLIKPCTKDLTTCVFGEKFASKVDLVPLSATTISRRIEDMSYFCEAVLVNRLK<br>NAKCGFTLQMDESTDVAGLAILLVFVRYIHESSFEEDMLFCKALPTQTTGEEI<br>FNLLNAYFEKHSIPWNLCYHICTDGAKAMVGVIKGVIARIKKLVPDIKASHCC<br>LHRHALAVKRIPNALHEVLNDAVKMINFIKSRPLNARVFALLCDDLGSLHKNL<br>LLHTETRWLSRGKVLTRFWELRDEIRIFFNEREFAGKLNDTSWLQNLAYIADI<br>FSYLNEVNLSLQGPNSTIFKVNSRINSIKSKLKLWEECITKNNTKCFANLNDF<br>LETSNTALDPNLKSNILEHLNGLKNTFLEYFPPTCNNISWVENPFNECGNVDT<br>LPIKEREQLIDIRTDTTLKSSFVPDGIGPFWIKLMDEFPEISERAVKLLMPFV<br>TTYLCEKSFSVYVATKTKYRNRLDAEDDMRLQLTTIHPDIDNLCNNKQAQKSH<br>(SEQ ID NO: 13) |

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the subject matter described herein may be employed in practicing the subject matter disclosed herein. It is intended that the following claims define the scope of the invention and that methods and structures within the scope of these claims and their equivalents be covered thereby.

What is claimed is:

1. A mutant TcBuster transposase comprising an amino acid sequence at least 70% identical to full-length SEQ ID NO: 1 and having the amino acid substitutions E247K, L268T, and Y284I when numbered in accordance with SEQ ID NO: 1.

2. The mutant TcBuster transposase of claim 1, wherein the mutant TcBuster transposase has increased transposition efficiency in comparison to a wild-type TcBuster transposase having amino acid sequence SEQ ID NO: 1.

3. The mutant TcBuster transposase of claim 1, further comprising an amino acid substitution of N85S, D99A, N209E, T219S, V356L, V377T, E469K, C470M, A472P, K490I, C512E, or any combination thereof, when numbered in accordance with SEQ ID NO: 1.

4. The mutant TcBuster transposase of claim 1, further comprising an amino acid substitution of D189A, V377T, E469K, K573E, E578L, or any combination thereof, when numbered in accordance with SEQ ID NO: 1.

5. The mutant TcBuster transposase of claim 1, wherein the amino acid sequence of the mutant TcBuster transposase is at least 80%, at least 90%, at least 95%, at least 98%, or at least 99% identical to full-length SEQ ID NO: 1.

6. A fusion transposase comprising a TcBuster transposase sequence and one or more of a DNA sequence specific binding domain and an additional Nuclear Localization Signal sequence, wherein the TcBuster transposase sequence has at least 70% identity to full-length SEQ ID NO: 1 and comprises the amino acid substitutions E247K, L268T, and Y284I when numbered in accordance with SEQ ID NO: 1.

7. The fusion transposase of claim 6, wherein the DNA sequence specific binding domain comprises a TALE domain, zinc finger domain, an AAV Rep DNA-binding domain, or any combination thereof.

8. The fusion transposase of claim 6, wherein the mutant TcBuster transposase sequence has increased transposition efficiency in comparison to a wild-type TcBuster transposase having amino acid sequence SEQ ID NO: 1.

9. The fusion transposase of claim 6, wherein the TcBuster transposase sequence and the one or more DNA sequence specific binding domains and/or additional Nuclear Localization Signal sequences are separated by one or more linkers.

10. The fusion transposase of claim 9, wherein the one or more linkers
a) are the same or different;
b) comprise 3 to 50 amino acids; and/or
c) comprise SEQ ID NO: 9.

11. A polynucleotide encoding the fusion transposase of claim 6.

12. A polynucleotide encoding the mutant TcBuster transposase of claim 1, which comprises one or more of:
a) DNA, unmodified messenger RNA (mRNA) or chemically modified mRNA that encodes the mutant TcBuster transposase or the fusion transposase;
b) a nucleic acid sequence at least about 80% identical to or complementary with full length SEQ ID NOs: 204 or 207;
c) a DNA vector;
d) a minicircle plasmid; and/or
e) a nucleic acid sequence encoding a transposon recognizable by the mutant TcBuster transposase or the fusion transposase.

13. The polynucleotide of claim 12, which is codon-optimized for expression in human cells.

14. A cell comprising the polynucleotide of claim 12.

15. A method of genome editing, which comprises introducing into a cell a mutant TcBuster transposase or a polynucleotide encoding the mutant TcBuster transposase, and a transposon recognizable by the mutant TcBuster transposase, wherein the mutant TcBuster transposase comprises an amino acid sequence at least 70% identical to full-length SEQ ID NO: 1 and comprises the amino acid substitutions E247K, L268T, and Y284I when numbered in accordance with SEQ ID NO: 1.

16. The method of claim 15, wherein the introducing comprises transfecting the cell with the aid of electroporation, microinjection, calcium phosphate precipitation, cationic polymers, dendrimers, liposome, microprojectile bombardment, fugene, direct sonic loading, cell squeezing, optical transfection, protoplast fusion, impalefection, magnetofection, nucleofection, or any combination thereof.

17. The method of claim 15, wherein the cell comprises a primary cell obtained from a subject.

18. The method of claim 17, wherein the primary cell is an immune cell.

19. A system for genome editing comprising the mutant TcBuster transposase of claim 1 and a transposon recognizable by the mutant TcBuster transposase.

20. The system of claim 19, wherein the transposon comprises a cargo cassette positioned between two inverted repeats.

21. The system of claim 20, wherein a left inverted repeat of the two inverted repeats comprises a nucleic acid sequence having at least 80% identity to SEQ ID NO: 3.

22. The system of claim 20, wherein a right inverted repeat of the two inverted repeats comprises a nucleic acid sequence having at least 80% identity to SEQ ID NO: 4.

23. The system of claim 20, wherein the cargo cassette is in a reverse direction.

* * * * *